US010363383B2

(12) United States Patent
Alizoti et al.

(10) Patent No.: US 10,363,383 B2
(45) Date of Patent: Jul. 30, 2019

(54) PRESSURE INDICATOR FOR AN OSCILLATING POSITIVE EXPIRATORY PRESSURE DEVICE

(71) Applicant: Trudell Medical International, London (CA)

(72) Inventors: Neritan Alizoti, London (CA); Chris Dobson, Sebringville (CA); James Schmidt, London (CA)

(73) Assignee: Trudell Medical International, London, Ontario (CA)

( * ) Notice: Subject to any disclaimer, the term of this patent is extended or adjusted under 35 U.S.C. 154(b) by 888 days.

(21) Appl. No.: 14/615,248

(22) Filed: Feb. 5, 2015

(65) Prior Publication Data
US 2015/0224269 A1 Aug. 13, 2015

Related U.S. Application Data

(60) Provisional application No. 61/937,433, filed on Feb. 7, 2014.

(51) Int. Cl.
*A61M 16/00* (2006.01)
*A61M 16/04* (2006.01)
*A61M 16/20* (2006.01)
*A61M 16/08* (2006.01)

(52) U.S. Cl.
CPC .... *A61M 16/0006* (2014.02); *A61M 16/0003* (2014.02); *A61M 16/049* (2014.02); *A61M 16/0866* (2014.02); *A61M 16/208* (2013.01); *A61M 2016/0027* (2013.01); *A61M 2205/3331* (2013.01); *A61M 2205/3341* (2013.01); *A61M 2205/3348* (2013.01); *A61M 2205/581* (2013.01); *A61M 2205/583* (2013.01); *A61M 2205/584* (2013.01)

(58) Field of Classification Search
CPC .............. A61M 16/00; A61M 16/0003; A61M 16/0866; A61M 16/08; A61M 16/20; A61M 16/0488; A61M 16/049; A61M 16/0006; A61M 2016/0027; A61M 2205/581; A61M 2205/583; A61M 2205/3331; A61M 2205/3341; A61M 2205/3348
USPC ....................... 128/205.23, 202.22
See application file for complete search history.

(56) References Cited

U.S. PATENT DOCUMENTS

| 393,869 | A | 12/1888 | Warren |
| 938,808 | A | 11/1909 | Yount |
| 2,670,739 | A | 3/1954 | NcNeill |

(Continued)

FOREIGN PATENT DOCUMENTS

| EP | 0 372 148 A1 | 6/1990 |
| EP | 0 678 306 A2 | 10/1995 |

(Continued)

OTHER PUBLICATIONS

U.S. Appl. No. 14/674,494, filed Mar. 31, 2015, Meyer et al.

(Continued)

*Primary Examiner* — Colin W Stuart
(74) *Attorney, Agent, or Firm* — Brinks Gilson & Lione

(57) ABSTRACT

A pressure indicator for a respiratory treatment device, the pressure indicator including an instrument for measuring pressures, a conduit configured to transmit a pressure within the respiratory treatment device to the instrument, and a pressure stabilizer orifice positioned within the conduit.

22 Claims, 71 Drawing Sheets

(56) References Cited

U.S. PATENT DOCUMENTS

| | | | |
|---|---|---|---|
| 2,918,917 A | 12/1959 | Emerson | |
| 3,710,780 A | 1/1973 | Milch | |
| 3,908,987 A | 9/1975 | Boehringer | |
| 4,054,134 A | 10/1977 | Kritzer | |
| 4,062,358 A | 12/1977 | Kritzer | |
| 4,164,219 A * | 8/1979 | Bird | A61M 16/00 128/204.19 |
| 4,182,366 A | 1/1980 | Boehringer | |
| 4,198,969 A | 4/1980 | Virag | |
| 4,221,381 A | 9/1980 | Ericson | |
| 4,226,233 A | 10/1980 | Kritzer | |
| 4,231,375 A | 11/1980 | Boehringer et al. | |
| 4,267,832 A | 5/1981 | Hakkinen | |
| 4,275,722 A | 6/1981 | Sorensen | |
| 4,298,023 A | 11/1981 | McGinnis | |
| 4,327,740 A | 5/1982 | Shuman | |
| 4,403,616 A | 9/1983 | King | |
| 4,436,090 A | 3/1984 | Darling | |
| 4,470,412 A | 9/1984 | Nowacki et al. | |
| 4,601,465 A | 7/1986 | Roy | |
| 4,611,591 A | 9/1986 | Inui et al. | |
| 4,635,631 A | 1/1987 | Izumi | |
| 4,651,731 A | 3/1987 | Vicenzi et al. | |
| 4,739,987 A | 4/1988 | Nicholson | |
| 4,770,413 A | 9/1988 | Green | |
| 4,973,047 A | 11/1990 | Norell | |
| 4,981,295 A | 1/1991 | Belman et al. | |
| 5,018,517 A | 5/1991 | Liardet | |
| 5,042,467 A | 8/1991 | Foley | |
| 5,065,746 A | 11/1991 | Steen | |
| 5,193,529 A | 3/1993 | Labaere | |
| 5,345,930 A | 9/1994 | Cardinal et al. | |
| 5,381,789 A | 1/1995 | Marquardt | |
| 5,451,190 A | 9/1995 | Liardet | |
| 5,479,920 A | 1/1996 | Piper et al. | |
| 5,540,220 A | 7/1996 | Gropper et al. | |
| 5,569,122 A | 10/1996 | Cegla | |
| 5,570,682 A | 11/1996 | Johnson | |
| 5,598,839 A | 2/1997 | Niles et al. | |
| 5,613,489 A | 3/1997 | Miller | |
| 5,645,049 A | 7/1997 | Foley et al. | |
| 5,647,345 A | 7/1997 | Saul | |
| 5,655,520 A | 8/1997 | Howe | |
| 5,658,221 A | 8/1997 | Hougen | |
| 5,791,339 A | 8/1998 | Winter | |
| 5,829,429 A | 11/1998 | Hughes | |
| 5,848,588 A | 12/1998 | Foley et al. | |
| 5,862,802 A | 1/1999 | Bird | |
| 5,890,998 A | 4/1999 | Hougen | |
| 5,893,361 A | 4/1999 | Hughes | |
| 5,899,832 A | 5/1999 | Hougen | |
| 5,910,071 A | 6/1999 | Hougen | |
| 5,925,831 A | 7/1999 | Storsved | |
| 6,013,020 A | 1/2000 | Meloul et al. | |
| 6,026,807 A | 2/2000 | Puderbaugh et al. | |
| 6,044,841 A | 4/2000 | Verdun et al. | |
| 6,058,932 A | 5/2000 | Hughes | |
| 6,066,101 A | 5/2000 | Johnson | |
| 6,067,984 A | 5/2000 | Piper | |
| 6,083,141 A | 7/2000 | Hougen | |
| 6,089,105 A | 7/2000 | Ricciardelli | |
| 6,102,038 A | 8/2000 | DeVries | |
| 6,167,881 B1 | 1/2001 | Hughes | |
| 6,176,235 B1 | 1/2001 | Benarrouch et al. | |
| D440,651 S | 4/2001 | Foran | |
| 6,240,917 B1 | 6/2001 | Andrade | |
| 6,253,766 B1 | 7/2001 | Niles | |
| 6,293,279 B1 | 9/2001 | Schmidt et al. | |
| 6,340,025 B1 | 1/2002 | Van Brunt | |
| 6,345,617 B1 | 2/2002 | Engelbreth et al. | |
| 6,412,481 B1 | 7/2002 | Bienvenu et al. | |
| 6,500,095 B1 | 12/2002 | Hougen | |
| 6,557,549 B2 | 5/2003 | Schmidt et al. | |
| 6,581,595 B1 | 6/2003 | Murdock et al. | |
| 6,581,596 B1 | 6/2003 | Truitt | |
| 6,581,598 B1 | 6/2003 | Foran et al. | |
| 6,581,600 B2 | 6/2003 | Bird | |
| 6,595,203 B1 | 7/2003 | Bird | |
| 6,606,989 B1 | 8/2003 | Brand | |
| 6,615,831 B1 | 9/2003 | Truitt | |
| 6,631,721 B1 | 10/2003 | Salter et al. | |
| 6,659,100 B2 | 12/2003 | O'Rourke | |
| 6,702,769 B1 | 3/2004 | Fowler-Hawkins | |
| 6,708,690 B1 | 3/2004 | Hete et al. | |
| 6,708,691 B1 | 3/2004 | Hayek | |
| 6,726,598 B1 | 4/2004 | Jarvis | |
| D490,519 S | 5/2004 | Pelerossi et al. | |
| 6,776,159 B2 | 8/2004 | Pelerossi et al. | |
| 6,848,443 B2 | 2/2005 | Schmidt et al. | |
| 6,851,425 B2 | 2/2005 | Jaffre | |
| 6,904,906 B2 | 6/2005 | Salter | |
| 6,923,181 B2 | 8/2005 | Tuck | |
| 6,929,007 B2 | 8/2005 | Emerson | |
| 6,984,214 B2 | 1/2006 | Fowler-Hawkins | |
| 7,055,520 B2 * | 6/2006 | Swisa | A61B 5/087 128/200.24 |
| 7,059,324 B2 | 6/2006 | Pelerossi et al. | |
| 7,096,866 B2 | 8/2006 | Be'eri et al. | |
| 7,134,434 B2 | 11/2006 | Truitt et al. | |
| 7,165,547 B2 | 1/2007 | Truitt et al. | |
| 7,188,621 B2 | 3/2007 | DeVries | |
| 7,191,776 B2 | 3/2007 | Niles | |
| 7,191,780 B2 | 3/2007 | Faram | |
| 7,214,170 B2 | 5/2007 | Sumners et al. | |
| 7,617,821 B2 | 11/2009 | Hughes | |
| 7,699,054 B2 | 4/2010 | Pelerossi et al. | |
| 7,717,847 B2 | 5/2010 | Smith | |
| 7,771,472 B2 | 8/2010 | Hendricksen | |
| 7,779,841 B2 | 8/2010 | Dunsmore et al. | |
| 7,798,148 B2 | 9/2010 | Doshi | |
| 7,856,979 B2 | 12/2010 | Doshi | |
| 7,909,033 B2 | 3/2011 | Faram | |
| 8,006,922 B2 | 8/2011 | Katzer | |
| 8,025,051 B2 | 9/2011 | Dagsland | |
| 8,025,054 B2 | 9/2011 | Dunsmore et al. | |
| 8,043,236 B2 | 10/2011 | Abrammerovich et al. | |
| 8,051,854 B2 | 11/2011 | Faram | |
| RE43,174 E | 2/2012 | Schmidt et al. | |
| 8,118,024 B2 | 2/2012 | DeVries et al. | |
| 8,225,785 B2 | 7/2012 | Richards et al. | |
| 8,327,849 B2 | 12/2012 | Grychowski et al. | |
| 8,460,223 B2 | 6/2013 | Huster et al. | |
| 8,469,029 B2 | 6/2013 | Brown et al. | |
| 8,485,179 B1 | 7/2013 | Meyer | |
| 8,539,179 B1 | 9/2013 | Meyer et al. | |
| 8,985,111 B2 | 3/2015 | Grychowski et al. | |
| 9,233,247 B2 | 1/2016 | Jaax | |
| 2007/0259759 A1 | 11/2007 | Sumners et al. | |
| 2008/0053456 A1 | 3/2008 | Brown et al. | |
| 2010/0139655 A1 | 7/2010 | Genosar | |
| 2010/0307487 A1 | 12/2010 | Dunsmore et al. | |
| 2011/0290240 A1 | 12/2011 | Meyer et al. | |
| 2012/0097164 A1 | 4/2012 | Rozario et al. | |
| 2012/0304988 A1 | 12/2012 | Meyer | |
| 2013/0284171 A1 | 10/2013 | Meyer | |
| 2013/0312746 A1 | 11/2013 | Grychowski | |
| 2014/0041657 A1 | 2/2014 | Meyer | |
| 2014/0150790 A1 | 6/2014 | Meyer | |
| 2015/0053209 A1 | 2/2015 | Meyer et al. | |
| 2015/0151060 A1 | 6/2015 | Grychowski et al. | |
| 2015/0297848 A1 | 10/2015 | Meyer et al. | |
| 2015/0374939 A1 | 12/2015 | Meyer et al. | |
| 2016/0136369 A1 | 5/2016 | Meyer et al. | |
| 2016/0310695 A1 | 10/2016 | Meyer et al. | |
| 2017/0028161 A1 | 2/2017 | Meyer et al. | |
| 2017/0049979 A1 | 2/2017 | Meyer et al. | |

FOREIGN PATENT DOCUMENTS

| | | |
|---|---|---|
| EP | 1435251 | 12/2003 |
| EP | 1 464 357 A1 | 10/2004 |

(56) References Cited

FOREIGN PATENT DOCUMENTS

| | | |
|---|---|---|
| EP | 1 435 251 B1 | 6/2006 |
| EP | 1 103 287 B1 | 6/2007 |
| EP | 1 897 576 A1 | 3/2008 |
| EP | 1 908 489 A1 | 4/2008 |
| EP | 2444114 | 4/2012 |
| EP | 2455137 | 5/2012 |
| GB | 2 425 488 A | 11/2006 |
| WO | WO 1989/03707 A1 | 5/1989 |
| WO | WO 1996/40376 | 12/1996 |
| WO | WO 1999/16490 | 4/1999 |
| WO | WO 2000/27455 | 5/2000 |
| WO | WO 2007/061648 A3 | 5/2007 |
| WO | WO 2007/119104 A3 | 10/2007 |
| WO | WO 2008/063966 A1 | 5/2008 |
| WO | WO 2008/122045 A1 | 10/2008 |
| WO | WO 2009/131965 | 10/2009 |
| WO | WO 2011/058470 | 5/2011 |
| WO | WO 2012/038864 A2 | 3/2012 |

OTHER PUBLICATIONS

U.S. Appl. No. 15/415,524, filed Jan. 25, 2017, Meyer et al.
U.S. Appl. No. 15/453,767, filed Mar. 8, 2017, Meyer et al.
U.S. Appl. No. 29/438,878, filed Dec. 4, 2012, Meyer.
U.S. Appl. No. 13/966,759, filed Aug. 14, 2013, Meyer.
U.S. Appl. No. 14/620,921, filed Feb. 12, 2015, Grychowski et al.
Web page entitled Bronchial Hygiene, acapella Vibratory PEP Therapy System accessed from http://www.smiths-medical.com/catalog/bronchial-hygiene/acapella/acapella.html on Jul. 7, 2009.
Web page entitled Thayer Quake accessed from http://www.thayermedical.com/quake.htm on Jul. 7, 2009.
David Sumners; Power Breathing and Strength; http://EzineArticles.com/972576 Published: Feb. 7, 2008.
Good Vibrations blog; http://vibrotraining.blogspot.com, Earliest posting Jan. 17, 2008.
Breathtaking News; More Youbreathe; Aug. 10, 2007.
Written Opinion of the International Searching Authority for related PCT application No. PCT/IB2015/050886 dated May 19, 2015 (6 pgs).

* cited by examiner

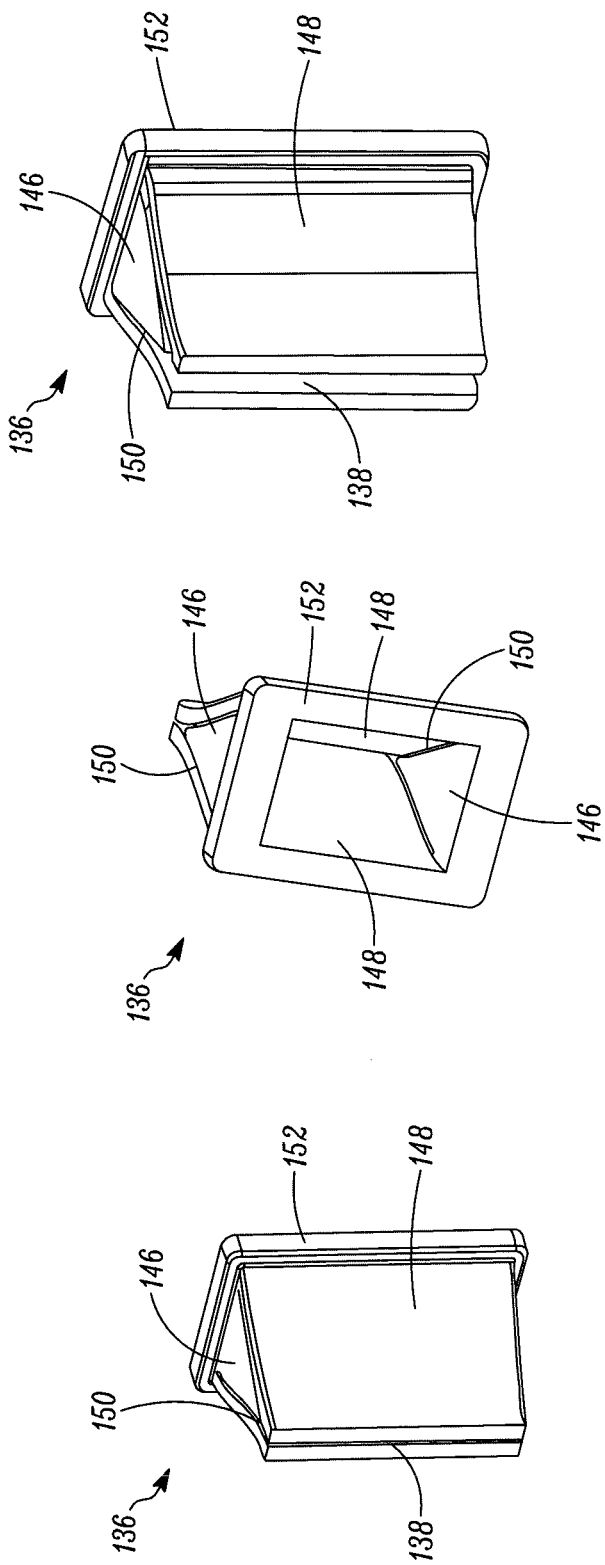

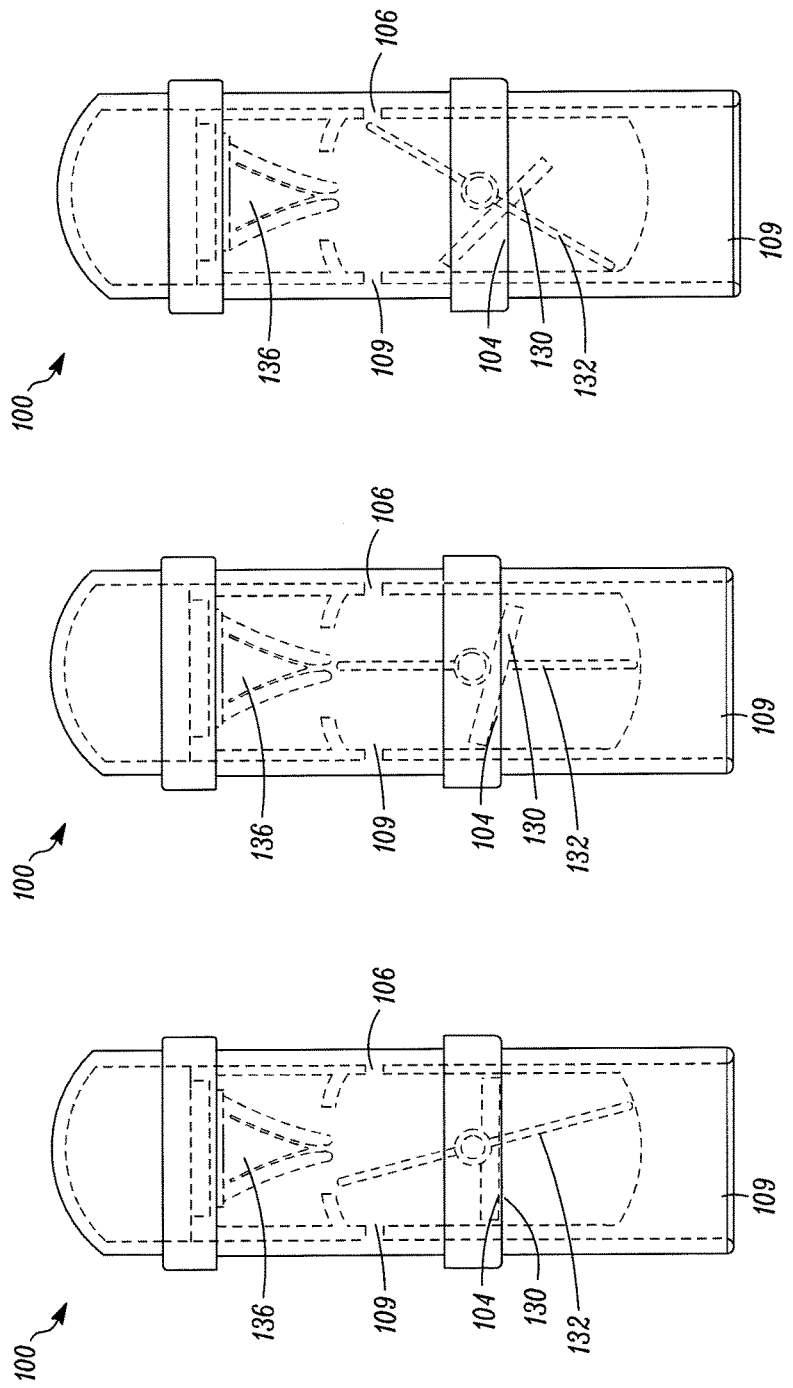

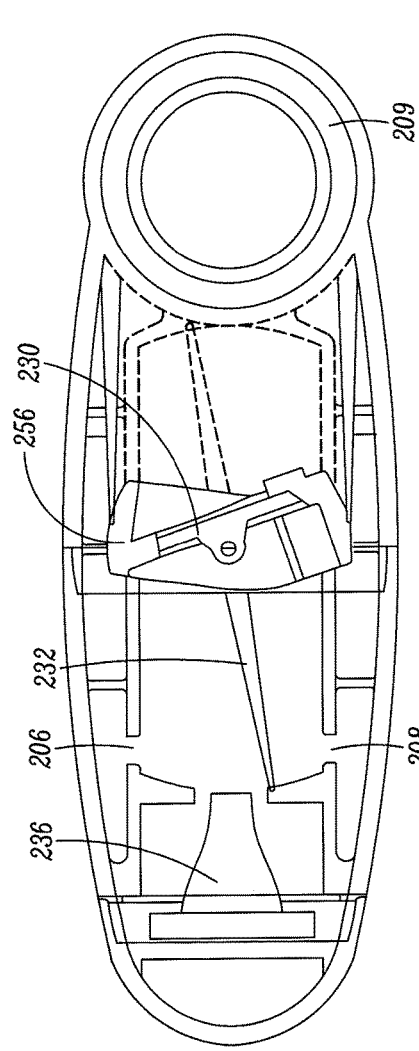
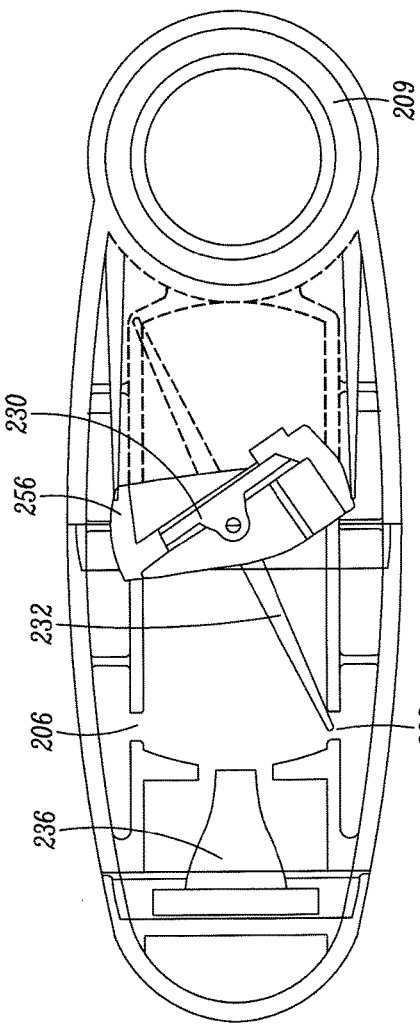
FIG. 34A
FIG. 34B

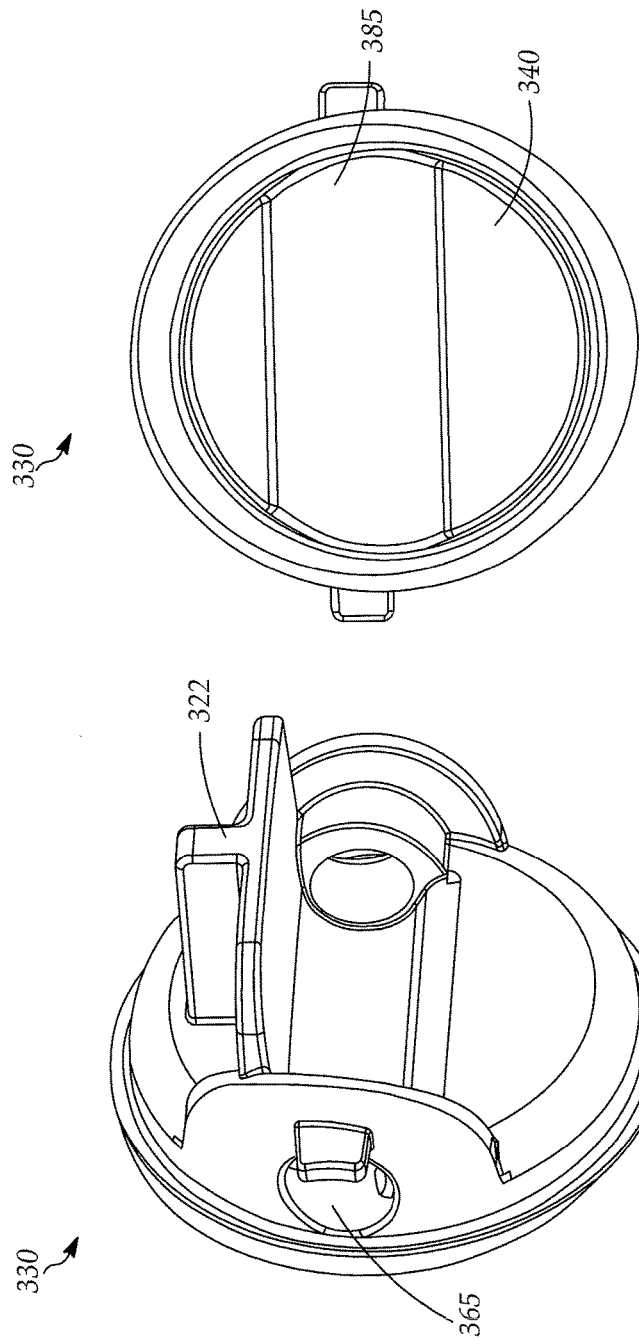

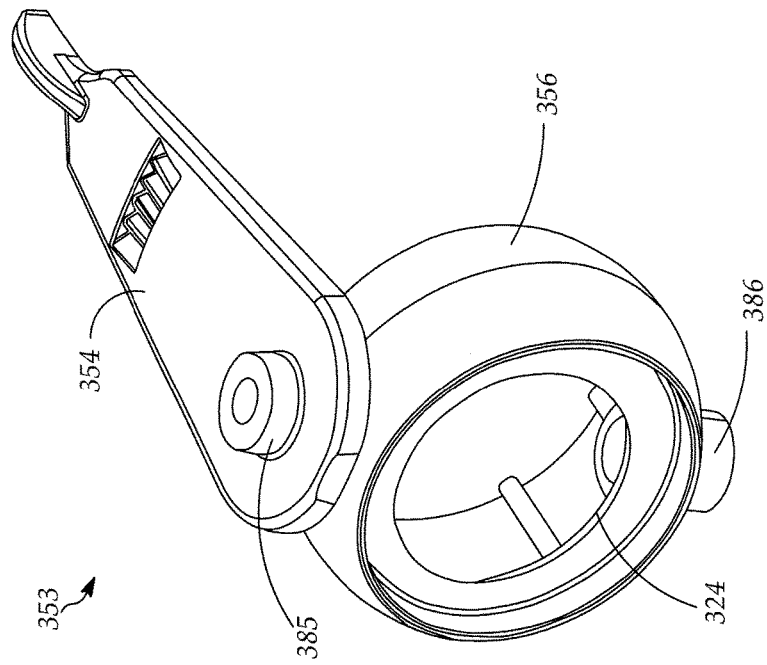

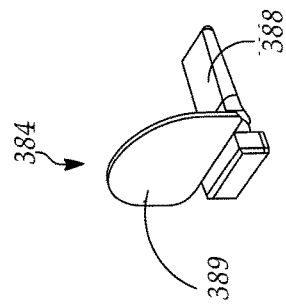
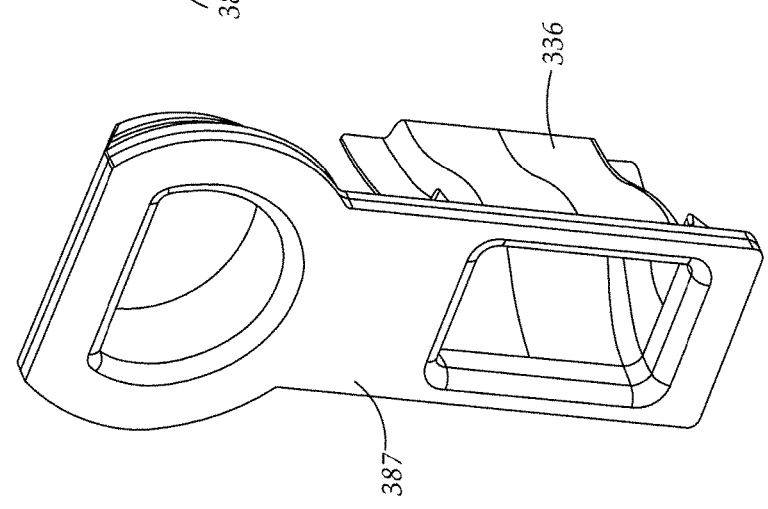
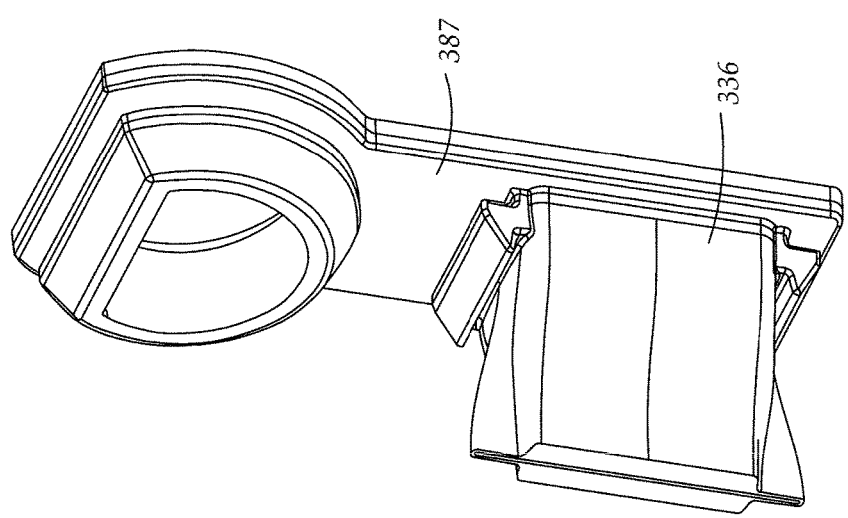

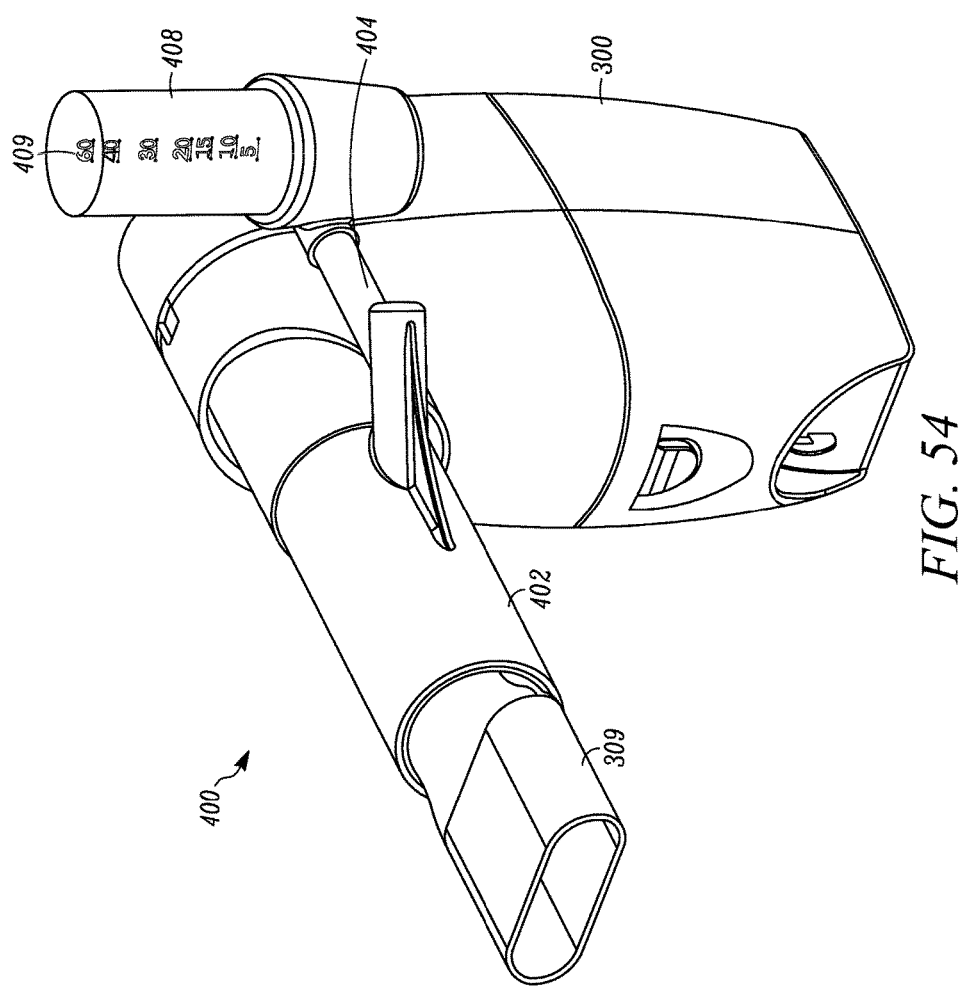

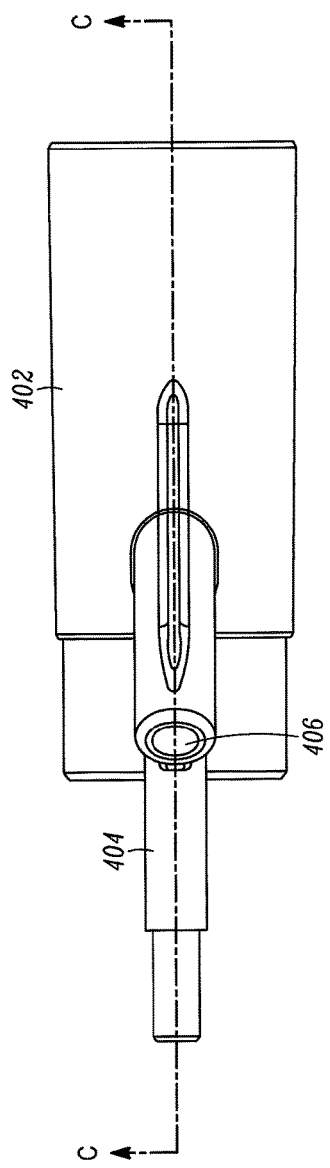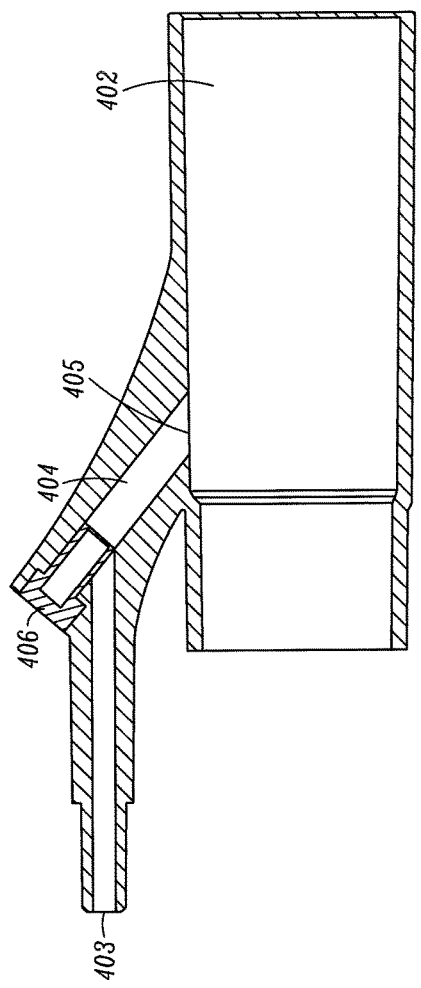
FIG. 55A
FIG. 55B

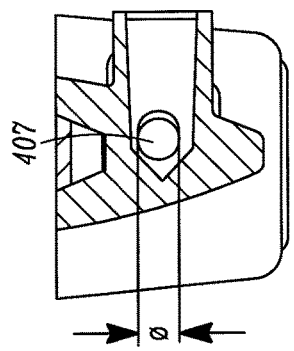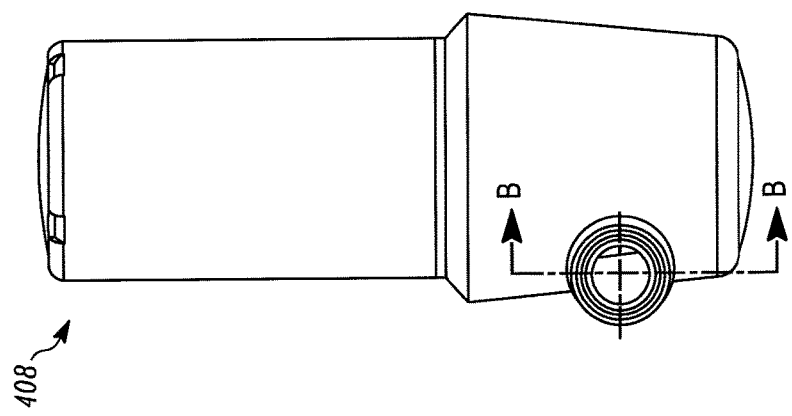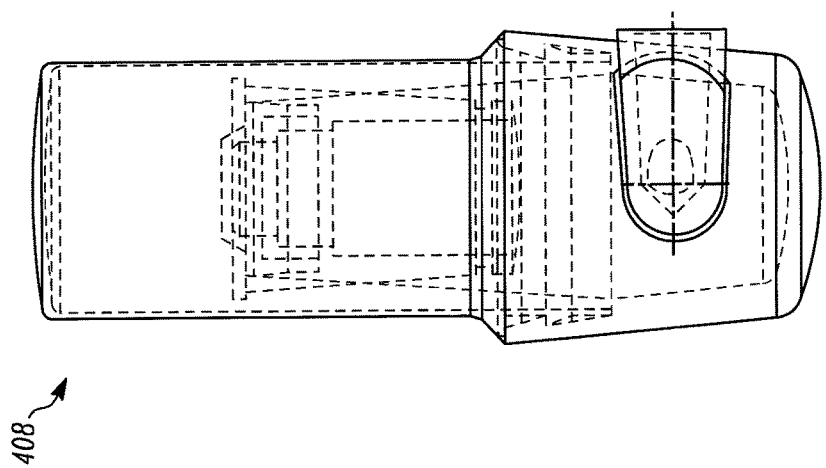
FIG. 56G

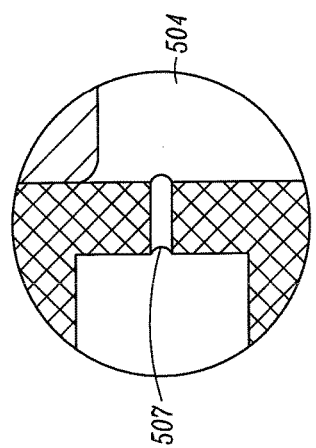
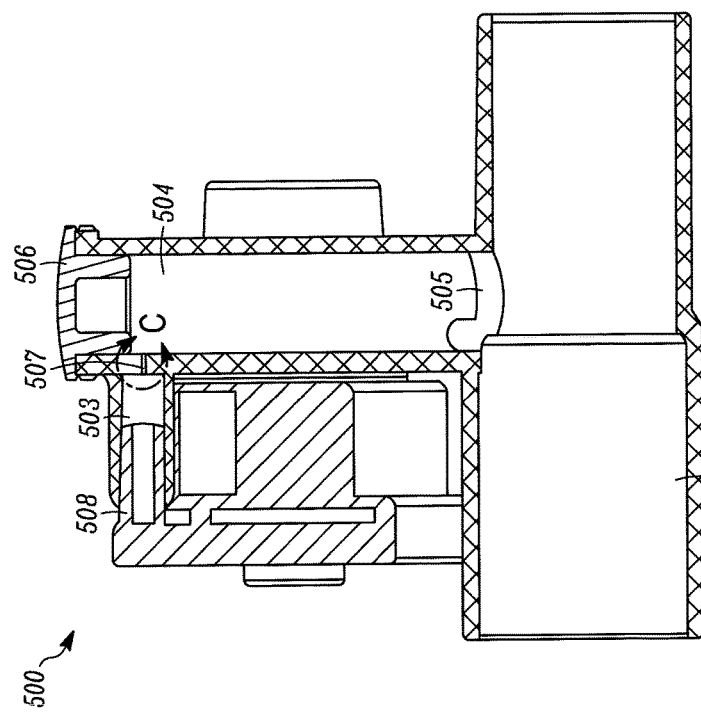
FIG. 59C
FIG. 59B

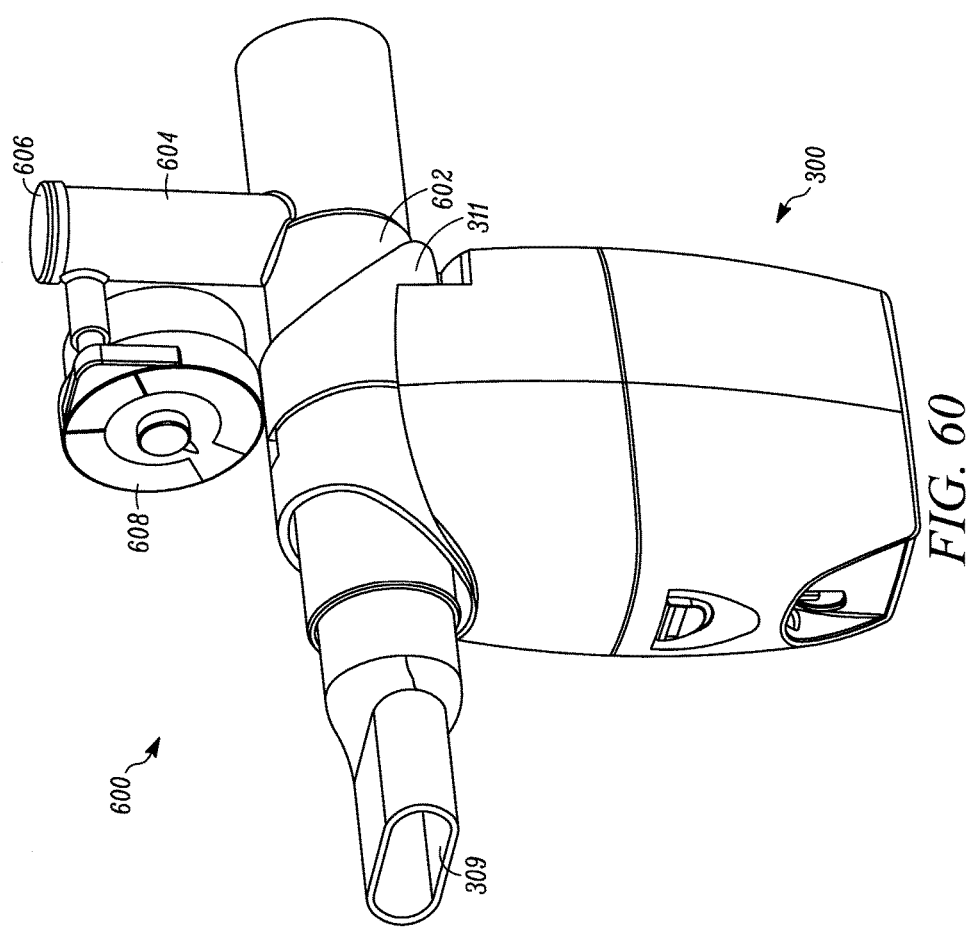

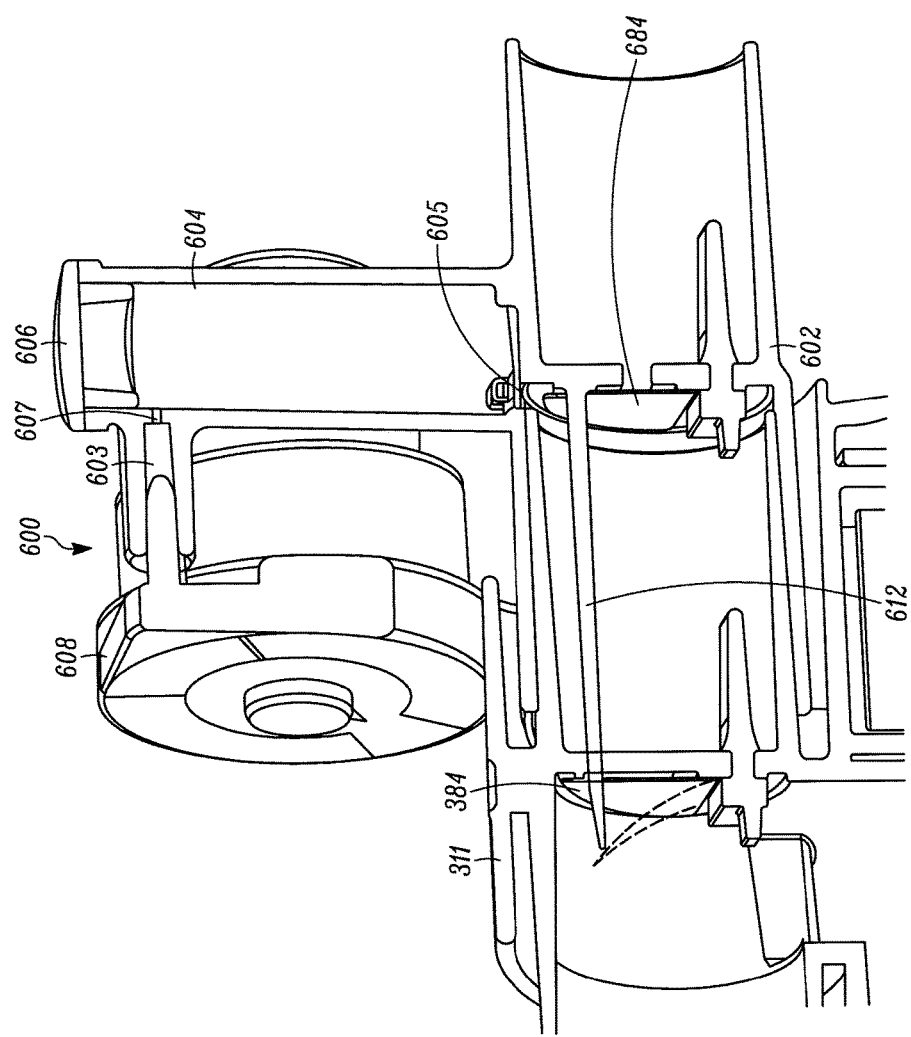

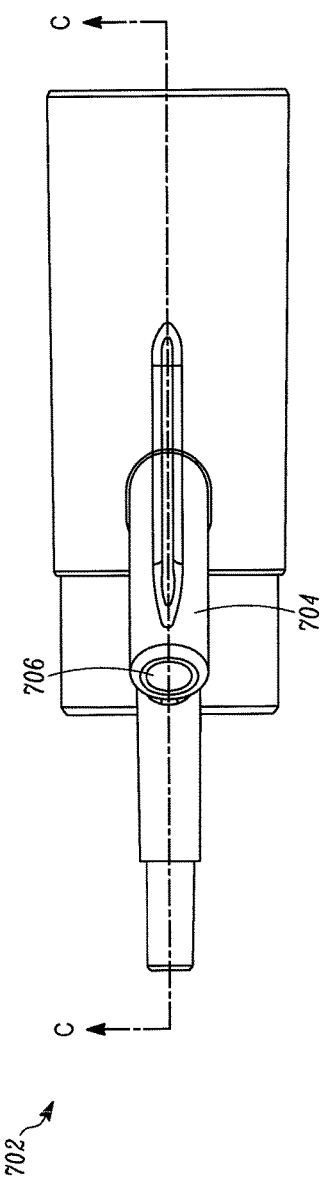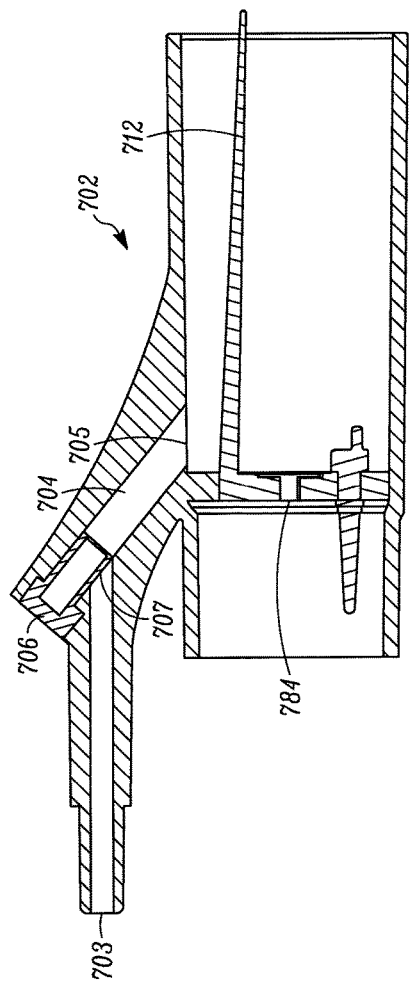
FIG. 63A
FIG. 63B

PRESSURE INDICATOR FOR AN OSCILLATING POSITIVE EXPIRATORY PRESSURE DEVICE

RELATED APPLICATION

This application claims the benefit of U.S. Provisional Application No. 61/937,433, filed Feb. 7, 2014, the entirety of which is incorporated herein by reference.

TECHNICAL FIELD

The present disclosure relates to a pressure indicator for a respiratory treatment device, and in particular, a pressure indicator for an oscillating positive expiratory pressure ("OPEP") device.

BACKGROUND

Each day, humans may produce upwards of 30 milliliters of sputum, which is a type of bronchial secretion. Normally, an effective cough is sufficient to loosen secretions and clear them from the body's airways. However, for individuals suffering from more significant bronchial obstructions, such as collapsed airways, a single cough may be insufficient to clear the obstructions.

OPEP therapy represents an effective bronchial hygiene technique for the removal of bronchial secretions in the human body and is an important aspect in the treatment and continuing care of patients with bronchial obstructions, such as those suffering from chronic obstructive lung disease. It is believed that OPEP therapy, or the oscillation of exhalation pressure at the mouth during exhalation, effectively transmits an oscillating back pressure to the lungs, thereby splitting open obstructed airways and loosening the secretions contributing to bronchial obstructions.

OPEP therapy is an attractive form of treatment because it can be easily taught to most patients, and such patients can assume responsibility for the administration of OPEP therapy throughout a hospitalization and also from home. To that end, a number of portable OPEP devices have been developed.

Providing users of such devices with a visual indication of the pressures achieved during OPEP therapy may assist the user and his or her clinician in administering OPEP therapy within a comfortable or a preferred range of pressures, thereby improving treatment results and decreasing the overall length of treatment. A portable pressure indicator for use with such OPEP devices is disclosed herein.

BRIEF SUMMARY

A pressure indicator for a respiratory treatment device includes an instrument for measuring pressures, a conduit configured to transmit a pressure within the respiratory treatment device to the instrument; and a pressure stabilizer orifice positioned within the conduit. The respiratory treatment device may be an oscillating positive expiratory pressure device. The instrument may be a manometer.

In another aspect, the instrument may have a passageway that is in fluid communication with the conduit. A portion of the conduit may extend into the passageway. The pressure stabilizer orifice may be positioned within the passageway. The pressure stabilizer orifice may be configured to dampen oscillations in the pressure transmitted from the respiratory treatment device to the instrument.

In another aspect, the pressure stabilizer orifice may have a cross-sectional area between 0.196 mm$^2$ and 1.767 mm$^2$. The pressure stabilizer office may have a cross-sectional area between 0.283 mm$^2$ and 0.636 mm$^2$. A cross-sectional area of the pressure stabilizer orifice may be less than a cross-sectional area of the conduit along an entire length of the conduit. A portion of the conduit may extend into the instrument or may form part of a passageway in the instrument which is in fluid communication with the conduit. The pressure stabilizer orifice may be positioned within the portion of the conduit extending into the instrument or may form part of the passageway in the instrument which is in fluid communication with the conduit. The pressure stabilizer orifice may be configured to dampen oscillations in the pressure transmitted from the respiratory treatment device to the instrument.

In another aspect, the instrument may include an indicator for providing visual or auditory feedback to a user of the respiratory treatment device during or after treatment.

In another aspect, the pressure indicator may be permanently or removably connectable to a mouthpiece of the respiratory treatment device. The pressure indicator may be connectable to the respiratory treatment device in a position where the flow of air from a user of the respiratory treatment device to an inlet of the conduit is substantially unobstructed.

In another aspect, the manometer may include a piston-type gauge. Alternatively, the manometer may include a dial-type gauge.

In another aspect, the instrument may be permanently or removably connectable to the respiratory treatment device in a position such that the indicator is viewable by a user of the respiratory treatment device during treatment.

In yet another aspect, a method of providing visual feedback during administration of oscillating positive expiratory pressure therapy includes receiving a flow of exhaled air at an inlet of a conduit connected to an oscillating positive expiratory pressure device, dampening oscillations in a pressure of the exhaled air in the conduit by restricting the flow of exhaled air through a pressure stabilizing orifice within the conduit, measuring the pressure at an outlet of the conduit, and providing an indication of the pressure measured at the outlet of the conduit In another aspect, a manometer measures the pressure at an outlet of the conduit. The manometer may include a passageway that is in fluid communication with the conduit. A portion of the conduit may extend into the passageway. The pressure stabilizer orifice may be position within the passageway.

In another aspect, the pressure stabilizer orifice may have a cross-sectional area between 0.196 mm$^2$ and 1.767 mm$^2$. The pressure stabilizer orifice may have a cross-sectional area between 0.283 mm$^2$ and 0.636 mm$^2$. A cross-sectional area of the pressure stabilizer orifice may be less than a cross-sectional area of the conduit along an entire length of the conduit. A portion of the conduit may extend into the manometer. The pressure stabilizer orifice may be positioned within the portion of the conduit extending into the manometer.

In another aspect, the indication may include auditory or visual feedback.

In another aspect, the conduit may be connectable to a mouthpiece of the oscillating positive expiratory pressure device. The conduit may be connectable to the oscillating positive expiratory pressure device in a position where the flow of air from a user of the oscillating positive expiratory pressure device to the inlet of the conduit is substantially unobstructed.

In another aspect, the manometer may include a piston-type gauge. Alternatively, the manometer may include a dial-type gauge.

In another aspect, the conduit is connectable to the oscillating positive expiratory pressure device in a position such that the manometer is viewable by a user of the oscillating positive expiratory pressure device during treatment.

In yet another aspect, a pressure indicator for a respiratory treatment device includes an instrument for measuring pressures, the instrument comprising a chamber, a chamber inlet configured to receive a flow of air from the respiratory treatment device, and a chamber vent in fluid communication with an atmosphere surrounding the respiratory treatment device. A pressure stabilizer orifice is positioned within at least one of the chamber inlet or the chamber vent. The pressure stabilizer orifice has a cross-sectional area smaller than the cross-sectional area of the inlet or the vent within which the pressure stabilizer orifice is positioned. The instrument may be a manometer.

In another aspect, the pressure indicator includes a membrane positioned in the chamber. The membrane is configured to divide the chamber such that the flow of air through the chamber inlet from the respiratory treatment device is blocked from passing through the chamber vent.

In another aspect, the chamber vent may include a plurality of openings. The pressure stabilizer orifice may include a plurality of orifices positioned within the openings.

In another aspect, the pressure stabilizer orifice may have a cross-sectional area between 0.196 mm$^2$ and 1.767 mm$^2$. The pressure stabilizer orifice may have a cross-sectional area between 0.283 mm$^2$ and 0.636 mm$^2$.

BRIEF DESCRIPTION OF THE DRAWINGS

FIG. 12 is a front perspective view of a variable nozzle shown without the flow of exhaled air therethrough;

FIG. 13 is a rear perspective view of the variable nozzle of FIG. 12 shown without the flow of exhaled air therethrough;

FIG. 14 is a front perspective view of the variable nozzle of FIG. 12 shown with a high flow of exhaled air therethrough;

FIGS. 15A-C are top phantom views of the OPEP device of FIG. 1 showing an exemplary illustration of the operation of the OPEP device of FIG. 1;

FIGS. 34A-B are top phantom views of the OPEP device of FIG. 18, illustrating the adjustability of the OPEP device;

FIG. 45 is a rear perspective view of the restrictor member of the FIG. 44;

FIG. 46 is a front view of the restrictor member of FIG. 44;

FIG. 47 is a front perspective view of an adjustment mechanism of the OPEP device of FIG. 35;

FIG. 50 is a front perspective view of a variable nozzle of the OPEP device of FIG. 35;

FIG. 51 is a rear perspective view of the variable nozzle of FIG. 50;

FIG. 52 is a front perspective view of the one-way valve of the OPEP device of FIG. 35.

FIG. 54 is a perspective view of the pressure indicator of FIG. 53 connected to the OPEP device of FIG. 35;

FIGS. 55A-B are side and cross-sectional views of the pressure indicator of FIG. 53;

FIGS. 56F-G are various side, phantom, and cross-sectional views of an alternative embodiment of the pressure indicator of FIG. 53;

FIGS. 59A-C are side are top and cross-sectional views of the pressure indicator of FIG. 57;

FIG. 60 is a perspective view of a third embodiment of a pressure indicator connected to the OPEP device of FIG. 35;

FIG. 61 is a cross-sectional view of the pressure indicator of FIG. 60 connected to the OPEP device of FIG. 35;

FIGS. 63A-B are side and cross-sectional view of the pressure indicator of FIG. 62;

DETAILED DESCRIPTION

Figure 1:
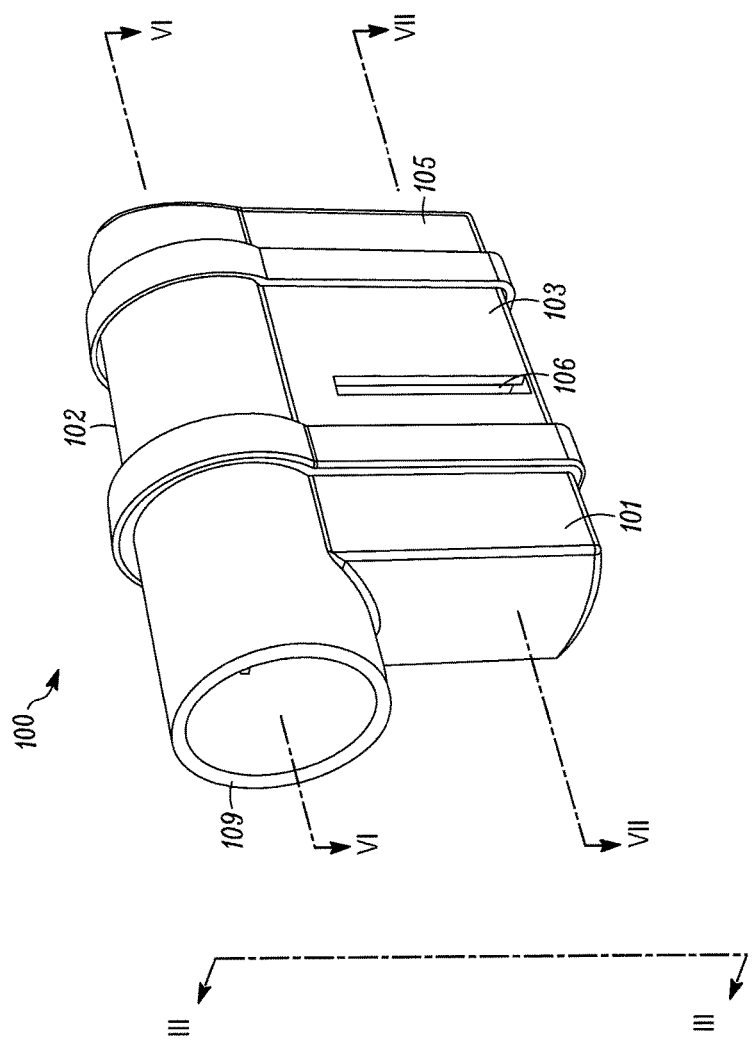
FIG. 1 is a front perspective view of an OPEP device.
Figure 2:
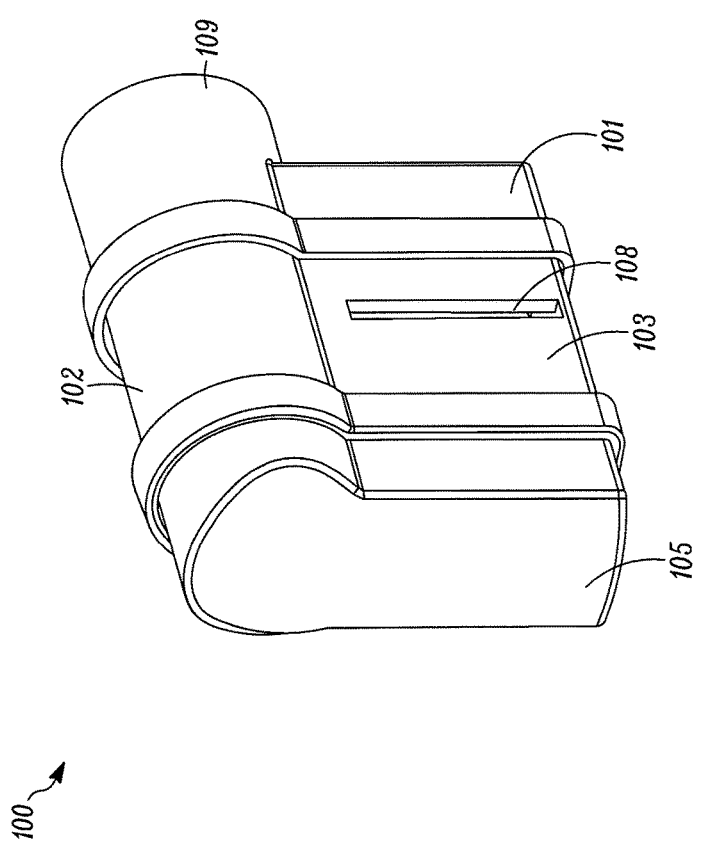
FIG. 2 is a rear perspective view of the OPEP device of FIG. 1.

OPEP therapy is effective within a range of operating conditions. For example, an adult human may have an exhalation flow rate ranging from 10 to 60 liters per minute, and may maintain a static exhalation pressure in the range of 8 to 18 cm $H_2O$. Within these parameters, OPEP therapy is believed to be most effective when changes in the exhalation pressure (i.e., the amplitude) range from 5 to 20 cm $H_2O$ oscillating at a frequency of 10 to 40 Hz. In contrast, an adolescent may have a much lower exhalation flow rate, and may maintain a lower static exhalation pressure, thereby altering the operating conditions most effective for the administration of OPEP therapy. Likewise, the ideal operating conditions for someone suffering from a respiratory illness, or in contrast, a healthy athlete, may differ from those of an average adult. As described below, the components of the disclosed OPEP devices are selectable and/or adjustable so that ideal operating conditions (e.g., amplitude and frequency of oscillating pressure) may be identified and maintained. Each of the various embodiments described herein achieve frequency and amplitude ranges that fall within the desired ranges set forth above. Each of the various embodiments described herein may also be configured to achieve frequencies and amplitudes that fall outside the ranges set forth above.

First OPEP Embodiment

Referring first to FIGS. 1-4, a front perspective view, a rear perspective view, a cross-sectional front perspective view, and an exploded view of an OPEP device 100 are shown. For purposes of illustration, the internal components of the OPEP device 100 are omitted in FIG. 3. The OPEP device 100 generally comprises a housing 102, a chamber inlet 104, a first chamber outlet 106, a second chamber outlet 108 (best seen in FIGS. 2 and 7), and a mouthpiece 109 in fluid communication with the chamber inlet 104. While the mouthpiece 109 is shown in FIGS. 1-4 as being integrally formed with the housing 102, it is envisioned that the mouthpiece 109 may be removable and replaceable with a mouthpiece 109 of a different size or shape, as required to maintain ideal operating conditions. In general, the housing 102 and the mouthpiece 109 may be constructed of any durable material, such as a polymer. One such material is Polypropylene. Alternatively, acrylonitrile butadiene styrene (ABS) may be used.

Alternatively, other or additional interfaces, such as breathing tubes or gas masks (not shown) may be attached in fluid communication with the mouthpiece 109 and/or associated with the housing 102. For example, the housing 102 may include an inhalation port (not shown) having a separate one-way inhalation valve (not shown) in fluid communication with the mouthpiece 109 to permit a user of the OPEP device 100 both to inhale the surrounding air through the one-way valve, and to exhale through the chamber inlet 104 without withdrawing the mouthpiece 109 of the OPEP device 100 between periods of inhalation and exhalation. In addition, any number of aerosol delivery devices may be connected to the OPEP device 100, for example, through the inhalation port mentioned above, for the simultaneous administration of aerosol and OPEP therapies. As such, the inhalation port may include, for example, an elastomeric adapter, or other flexible adapter, capable of accommodating the different mouthpieces or outlets of the particular aerosol delivery device that a user intends to use with the OPEP device 100. As used herein, the term aerosol delivery devices should be understood to include, for example, without limitation, any nebulizer, soft mist inhaler, pressurized metered dose inhaler, dry powder inhaler, combination of a holding chamber a pressurized metered dose inhaler, or the like. Suitable commercially available aerosol delivery devices include, without limitation, the AEROECLIPSE nebulizer, RESPIMAT soft mist inhaler, LC Sprint nebulizer, AEROCHAMBER PLUS holding chambers, MICRO MIST nebulizer, SIDESTREAM nebulizers, Inspiration Elite nebulizers, FLOVENT pMDI, VENTOLIN pMDI, AZMACORT pMDI, BECLOVENT pMDI, QVAR pMDI and AEROBID PMDI, XOPENEX pMDI, PROAIR pMDI, PROVENT pMDI, SYMBICORT pMDI, TURBOHALER DPI, and DISKHALER DPI. Descriptions of suitable aerosol delivery devices may be found in U.S. Pat. Nos. 4,566,452; 5,012,803; 5,012,804; 5,312,046; 5,497,944; 5,622,162; 5,823,179; 6,293,279; 6,435,177; 6,484,717; 6,848,443; 7,360,537; 7,568,480; and 7,905,228, the entireties of which are herein incorporated by reference.

In FIGS. 1-4, the housing 102 is generally box-shaped. However, a housing 102 of any shape may be used. Furthermore, the chamber inlet 104, the first chamber outlet 106, and the second chamber outlet 108 could be any shape or series of shapes, such as a plurality (i.e., more than one) of circular passages or linear slots. More importantly, it should be appreciated that the cross-sectional area of the chamber inlet 104, the first chamber outlet 106, and the second chamber outlet 108 are only a few of the factors influencing the ideal operating conditions described above.

Preferably, the housing 102 is openable so that the components contained therein can be periodically accessed, cleaned, replaced, or reconfigured, as required to maintain the ideal operating conditions. As such, the housing 102 is shown in FIGS. 1-4 as comprising a front section 101, a middle section 103, and a rear section 105. The front section 101, the middle section 103, and the rear section 105 may be removably connected to one another by any suitable means, such as a snap-fit, a compression fit, etc., such that a seal forms between the relative sections sufficient to permit the OPEP device 100 to properly administer OPEP therapy.

Figure 3:
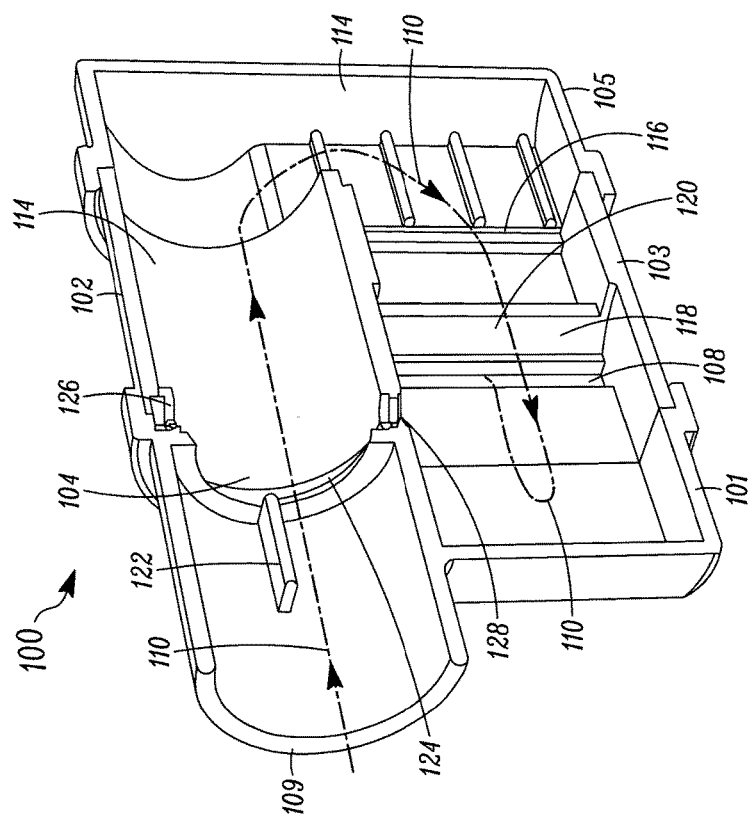
FIG. 3 is a cross-sectional perspective view taken along line III in FIG. 1 of the OPEP device shown without the internal components of the OPEP device.
Figure 7:
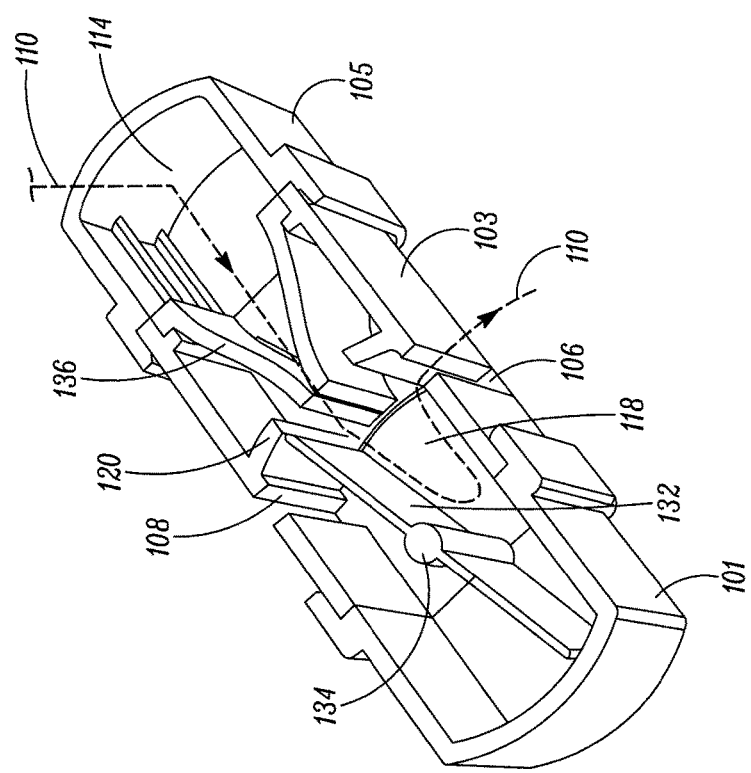
FIG. 7 is a different cross-sectional perspective view taken along line VII in FIG. 1 of the OPEP device shown with the internal components of the OPEP device.

As shown in FIG. 3, an exhalation flow path 110, identified by a dashed line, is defined between the mouthpiece 109 and at least one of the first chamber outlet 106 and the second chamber outlet 108 (best seen in FIG. 7). More specifically, the exhalation flow path 110 begins at the mouthpiece 109, passes through the chamber inlet 104, and enters into a first chamber 114, or an entry chamber. In the first chamber 114, the exhalation flow path makes a 180-degree turn, passes through a chamber passage 116, and enters into a second chamber 118, or an exit chamber. In the second chamber 118, the exhalation flow path 110 may exit the OPEP device 100 through at least one of the first chamber outlet 106 and the second chamber outlet 108. In this way, the exhalation flow path 110 is "folded" upon itself, i.e., it reverses longitudinal directions between the chamber inlet 104 and one of the first chamber outlet 106 or the second chamber outlet 108. However, those skilled in the art will appreciate that the exhalation flow path 110 identified by the dashed line is exemplary, and that air exhaled into the OPEP device 100 may flow in any number of directions or paths as it traverses from the mouthpiece 109 or chamber inlet 104 and the first chamber outlet 106 or the second chamber outlet 108.

FIG. 3 also shows various other features of the OPEP device 100 associated with the housing 102. For example, a stop 122 prevents a restrictor member 130 (see FIG. 5), described below, from opening in a wrong direction; a seat 124 shaped to accommodate the restrictor member 130 is formed about the chamber inlet 104; and, an upper bearing 126 and a lower bearing 128 are formed within the housing 102 and configured to accommodate a shaft rotatably mounted therebetween. One or more guide walls 120 are positioned in the second chamber 118 to direct exhaled air along the exhalation flow path 110.

Figure 5:
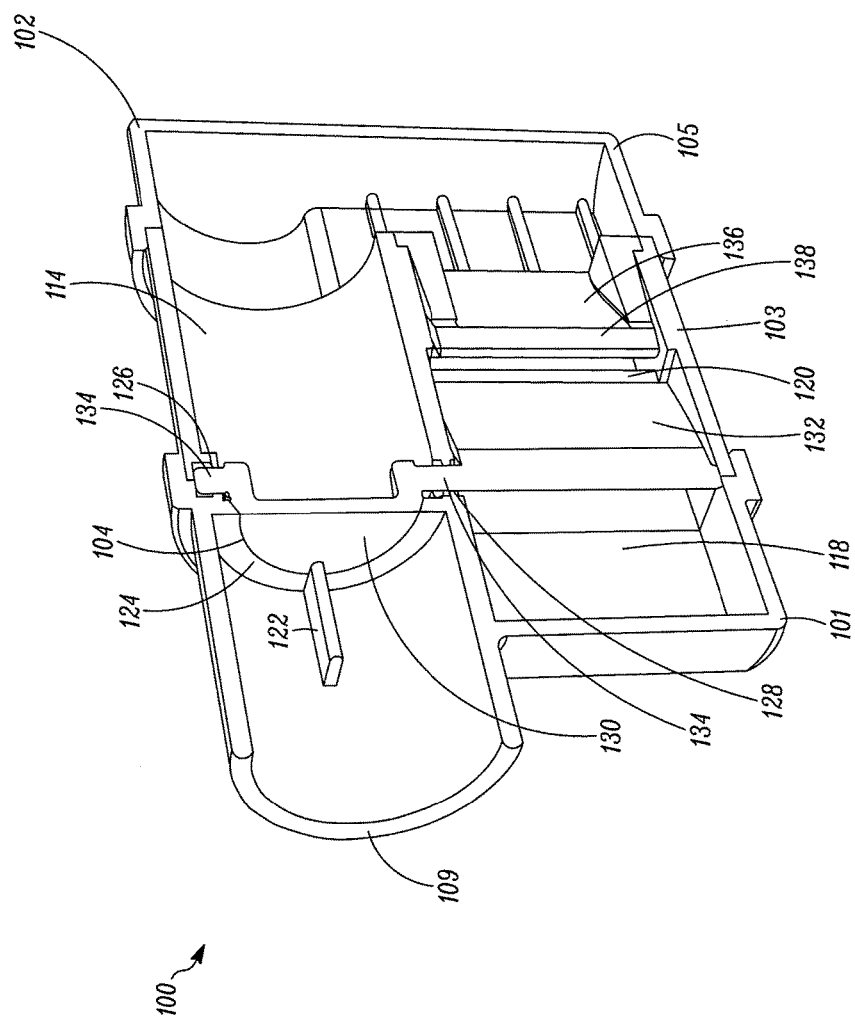
FIG. 5 is a cross-sectional perspective view taken along line III in FIG. 1 of the OPEP device shown with the internal components of the OPEP device.
Figure 6:
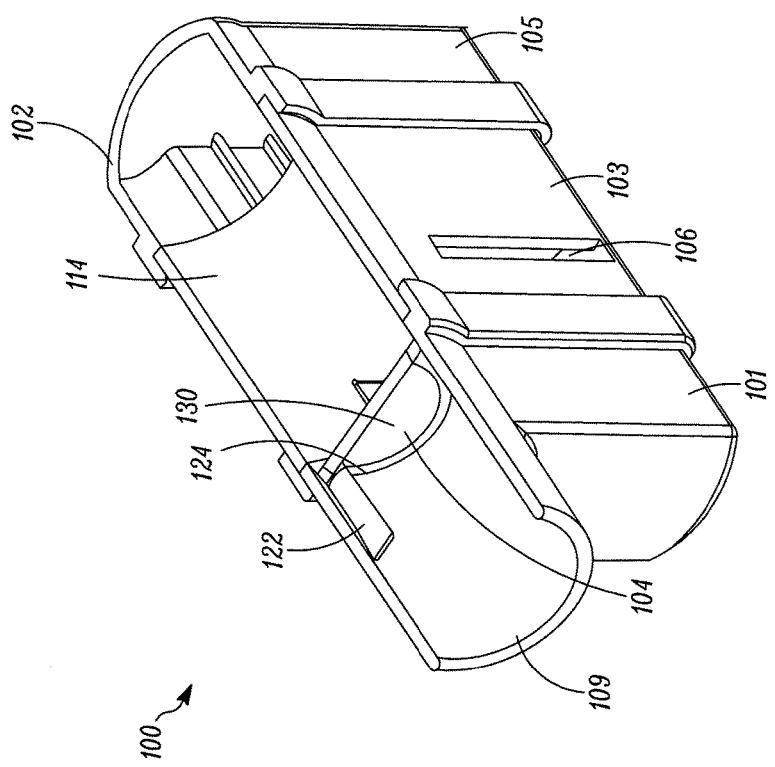
FIG. 6 is a different cross-sectional perspective view taken along line VI in FIG. 1 of the OPEP device shown with the internal components of the OPEP device.

Turning to FIGS. 5-7, various cross-sectional perspective views of the OPEP device 100 are shown with its internal components. The internal components of the OPEP device 100 comprise a restrictor member 130, a vane 132, and an optional variable nozzle 136. As shown, the restrictor member 130 and the vane 132 are operatively connected by means of a shaft 134 rotatably mounted between the upper bearing 126 and the lower bearing 128, such that the restrictor member 130 and the vane 132 are rotatable in unison about the shaft 134. As described below in further detail, the variable nozzle 136 includes an orifice 138 configured to increase in size in response to the flow of exhaled air therethrough.

Figure 4:
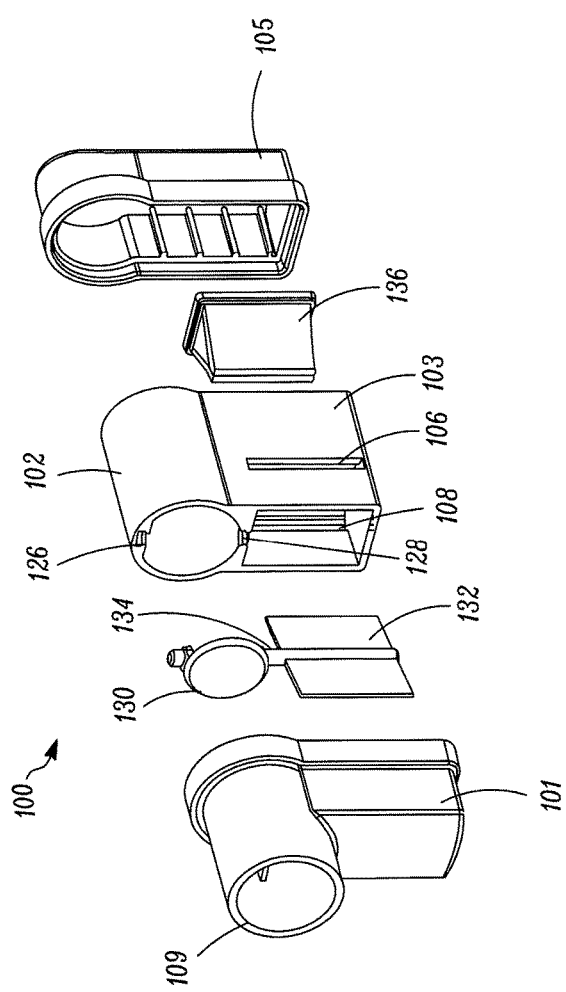
FIG. 4 is an exploded view of the OPEP device of FIG. 1, shown with the internal components of the OPEP device.

FIGS. 4-6 further illustrate the division of the first chamber 114 and the second chamber 118 within the housing 102. As previously described, the chamber inlet 104 defines an entrance to the first chamber 114. The restrictor member 130 is positioned in the first chamber 114 relative to a seat 124 about the chamber inlet 104 such that it is moveable between a closed position, where a flow of exhaled air along the exhalation flow path 110 through the chamber inlet 104 is restricted, and an open position, where the flow of exhaled air through the chamber inlet 104 is less restricted. Likewise, the variable nozzle 136, which is optional, is mounted about or positioned in the chamber passage 116, such that the flow of exhaled air entering the first chamber 114 exits the first chamber 114 through the orifice 138 of the variable nozzle 136. Exhaled air exiting the first chamber 114 through the orifice 138 of the variable nozzle 136 enters the second chamber, which is defined by the space within the housing 102 occupied by the vane 132 and the guide walls 120. Depending on the position of the vane 132, the exhaled air is then able to exit the second chamber 118 through at least one of the first chamber outlet 106 and the second chamber outlet 108.

Figure 8:
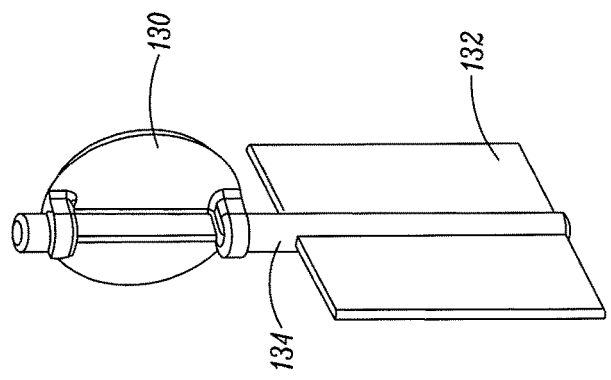
FIG. 8 is a front perspective view of a restrictor member operatively connected to a vane.
Figure 9:
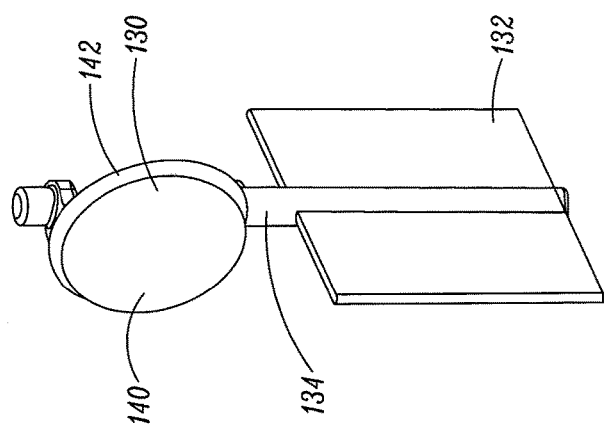
FIG. 9 is a rear perspective view of the restrictor member operatively connected to the vane shown in FIG. 8.

FIGS. 8-14 show the internal components of the OPEP device 100 in greater detail. Turning first to FIGS. 8-9, a front perspective view and a rear perspective view shows the restrictor member 130 operatively connected to the vane 132 by the shaft 134. As such, the restrictor member 130 and the vane 132 are rotatable about the shaft 134 such that rotation of the restrictor member 130 results in a corresponding rotation of the vane 132, and vice-versa. Like the housing 102, the restrictor member 130 and the vane 132 may be made of constructed of any durable material, such as a polymer. Preferably, they are constructed of a low shrink, low friction plastic. One such material is acetal.

As shown, the restrictor member 130, the vane 132, and the shaft 134 are formed as a unitary component. The restrictor member 130 is generally disk-shaped, and the vane 132 is planar. The restrictor member 130 includes a generally circular face 140 axially offset from the shaft 134 and a beveled or chamfered edge 142 shaped to engage the seat 124 formed about the chamber inlet 104. In this way, the restrictor member 130 is adapted to move relative to the chamber inlet 104 about an axis of rotation defined by the shaft 134 such that the restrictor member 130 may engage the seat 124 in a closed position to substantially seal and restrict the flow of exhaled air through the chamber inlet 104. However, it is envisioned that the restrictor member 130 and the vane 132 may be formed as separate components connectable by any suitable means such that they remain independently replaceable with a restrictor member 130 or a vane 132 of a different shape, size, or weight, as selected to maintain ideal operating conditions. For example, the restrictor member 130 and/or the vane 132 may include one or more contoured surfaces. Alternatively, the restrictor member 130 may be configured as a butterfly valve.

Figure 10:
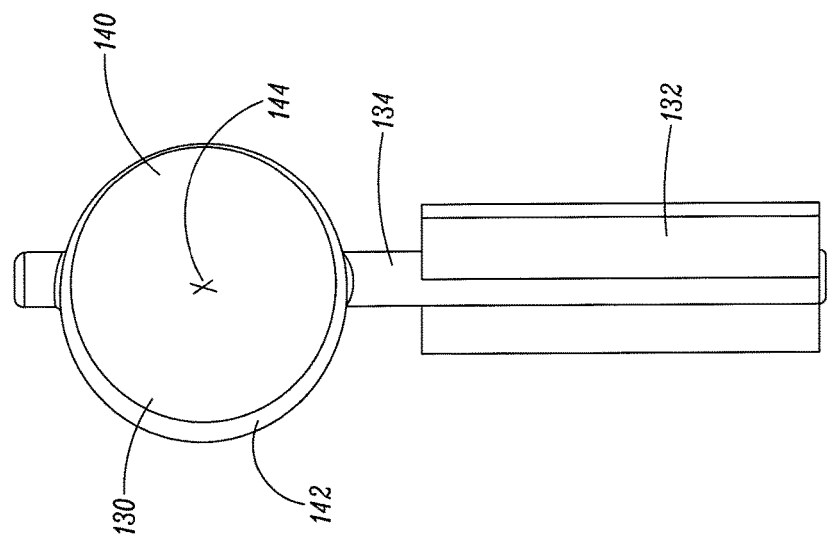
FIG. 10 is a front view of the restrictor member operatively connected to the vane shown in FIG. 8.

Turning to FIG. 10, a front view of the restrictor member 130 and the vane 132 is shown. As previously described, the restrictor member 130 comprises a generally circular face 140 axially offset from the shaft 134. The restrictor member 130 further comprises a second offset designed to facilitate movement of the restrictor member 130 between a closed position and an open position. More specifically, a center 144 of the face 140 of the restrictor member 130 is offset from the plane defined by the radial offset and the shaft 134, or the axis of rotation. In other words, a greater surface area of the face 140 of the restrictor member 130 is positioned on one side of the shaft 134 than on the other side of the shaft 134. Pressure at the chamber inlet 104 derived from exhaled air produces a force acting on the face 140 of the restrictor member 130. Because the center 144 of the face 140 of the restrictor member 130 is offset as described above, a resulting force differential creates a torque about the shaft 134. As further explained below, this torque facilitates movement of the restrictor member 130 between a closed position and an open position.

Figure 11:
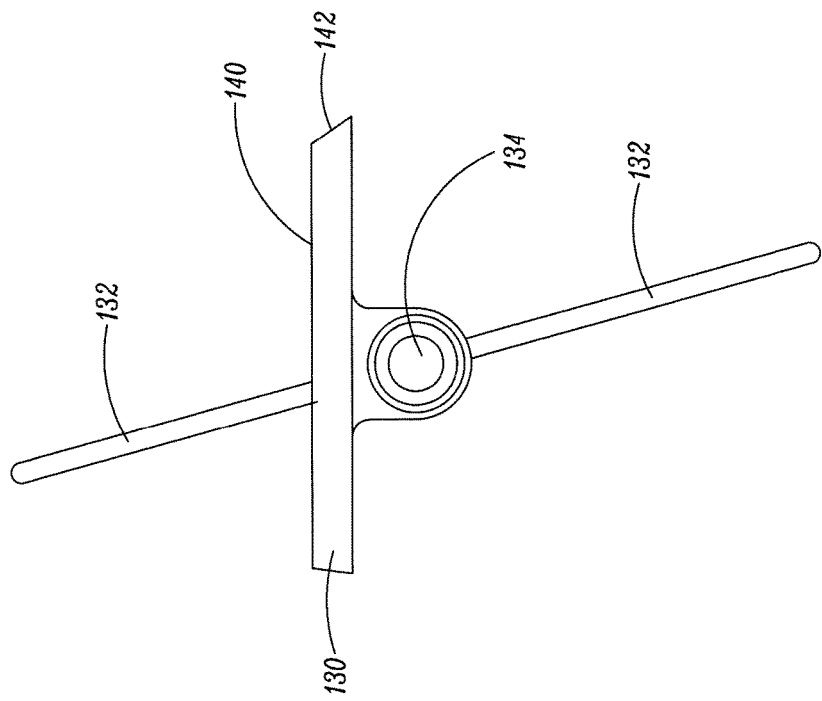
FIG. 11 is a top view of the restrictor member operatively connected to the vane shown in FIG. 8.

Turning to FIG. 11, a top view of the restrictor member 130 and the vane 132 is shown. As illustrated, the vane 132 is connected to the shaft 134 at a 75° angle relative to the face 140 of restrictor member 130. Preferably, the angle will remain between 60° and 80°, although it is envisioned that the angle of the vane 132 may be selectively adjusted to maintain the ideal operating conditions, as previously discussed. It is also preferable that the vane 132 and the restrictor member 130 are configured such that when the OPEP device 100 is fully assembled, the angle between a centerline of the variable nozzle 136 and the vane 132 is between 10° and 25° when the restrictor member 130 is in a closed position. Moreover, regardless of the configuration, it is preferable that the combination of the restrictor member 130 and the vane 132 have a center of gravity aligned with the shaft 134, or the axis of rotation. In full view of the present disclosure, it should be apparent to those skilled in the art that the angle of the vane 132 may be limited by the size or shape of the housing 102, and will generally be less than half the total rotation of the vane 132 and the restrictor member 130.

Turning to FIGS. 12 and 13, a front perspective view and a rear perspective view of the variable nozzle 136 is shown without the flow of exhaled air therethrough. In general, the variable nozzle 136 includes top and bottom walls 146, side walls 148, and V-shaped slits 150 formed therebetween. As shown, the variable nozzle is generally shaped like a duckbill type valve. However, it should be appreciated that nozzles or valves of other shapes and sizes may also be used. The variable nozzle 136 may also include a lip 152 configured to mount the variable nozzle 136 within the housing 102 between the first chamber 114 and the second chamber 118. The variable nozzle 136 may be constructed or molded of any material having a suitable flexibility, such as silicone, and preferably with a wall thickness of between 0.50 and 2.00 millimeters, and an orifice width between 0.25 to 1.00 millimeters or smaller depending on manufacturing capabilities.

As previously described, the variable nozzle 136 is optional in the operation of the OPEP device 100. It should also be appreciated that the OPEP device 100 could alternatively omit both the chamber passage 116 and the variable nozzle 136, and thus comprise a single-chamber embodiment. Although functional without the variable nozzle 136, the performance of the OPEP device 100 over a wider range of exhalation flow rates is improved when the OPEP device 100 is operated with the variable nozzle 136. The chamber passage 116, when used without the variable nozzle 136, or the orifice 138 of the variable nozzle 136, when the variable nozzle 136 is included, serves to create a jet of exhaled air having an increased velocity. As explained in more detail below, the increased velocity of the exhaled air entering the second chamber 118 results in a proportional increase in the force applied by the exhaled air to the vane 132, and in turn, an increased torque about the shaft 134, all of which affect the ideal operating conditions.

Without the variable nozzle 136, the orifice between the first chamber 114 and the second chamber 118 is fixed according to the size, shape, and cross-sectional area of the chamber passage 116, which may be selectively adjusted by any suitable means, such as replacement of the middle section 103 or the rear section 105 of the housing. On the other hand, when the variable nozzle 136 is included in the OPEP device 100, the orifice between the first chamber 114 and the second chamber 118 is defined by the size, shape, and cross-sectional area of the orifice 138 of the variable nozzle 136, which may vary according to the flow rate of exhaled air and/or the pressure in the first chamber 114.

Turning to FIG. 14, a front perspective view of the variable nozzle 136 is shown with a flow of exhaled air therethrough. One aspect of the variable nozzle 136 shown in FIG. 14 is that, as the orifice 138 opens in response to the flow of exhaled air therethrough, the cross-sectional shape of the orifice 138 remains generally rectangular, which during the administration of OPEP therapy results in a lower drop in pressure through the variable nozzle 136 from the first chamber 114 (See FIGS. 3 and 5) to the second chamber 118. The generally consistent rectangular shape of the orifice 138 of the variable nozzle 136 during increased flow rates is achieved by the V-shaped slits 150 formed between the top and bottom walls 146 and the side walls 148, which serve to permit the side walls 148 to flex without restriction. Preferably, the V-shaped slits 150 are as thin as possible to minimize the leakage of exhaled air therethrough. For example, the V-shaped slits 150 may be approximately 0.25 millimeters wide, but depending on manufacturing capabilities, could range between 0.10 and 0.50 millimeters. Exhaled air that does leak through the V-shaped slits 150 is ultimately directed along the exhalation flow path by the guide walls 120 in the second chamber 118 protruding from the housing 102.

It should be appreciated that numerous factors contribute to the impact the variable nozzle 136 has on the performance of the OPEP device 100, including the geometry and material of the variable nozzle 136. By way of example only, in order to attain a target oscillating pressure frequency of between 10 to 13 Hz at an exhalation flow rate of 15 liters per minute, in one embodiment, a 1.0 by 20.0 millimeter passage or orifice may be utilized. However, as the exhalation flow rate increases, the frequency of the oscillating pressure in that embodiment also increases, though at a rate too quickly in comparison to the target frequency. In order to attain a target oscillating pressure frequency of between 18 to 20 Hz at an exhalation flow rate of 45 liters per minute, the same embodiment may utilize a 3.0 by 20.0 millimeter passage or orifice. Such a relationship demonstrates the desirability of a passage or orifice that expands in cross-sectional area as the exhalation flow rate increases in order to limit the drop in pressure across the variable nozzle 136.

Turning to FIGS. 15A-C, top phantom views of the OPEP device 100 show an exemplary illustration of the operation of the OPEP device 100. Specifically, FIG. 15A shows the restrictor member 130 in an initial, or closed position, where the flow of exhaled air through the chamber inlet 104 is restricted, and the vane 132 is in a first position, directing the flow of exhaled air toward the first chamber outlet 106. FIG. 15B shows this restrictor member 130 in a partially open position, where the flow of exhaled air through the chamber inlet 104 is less restricted, and the vane 132 is directly aligned with the jet of exhaled air exiting the variable nozzle 136. FIG. 15C shows the restrictor member 130 in an open position, where the flow of exhaled air through the chamber inlet 104 is even less restricted, and the vane 132 is in a second position, directing the flow of exhaled air toward the second chamber outlet 108. It should be appreciated that the cycle described below is merely exemplary of the operation of the OPEP device 100, and that numerous factors may affect operation of the OPEP device 100 in a manner that results in a deviation from the described cycle. However, during the operation of the OPEP device 100, the restrictor member 130 and the vane 132 will generally reciprocate between the positions shown in FIGS. 15A and 15C.

During the administration of OPEP therapy, the restrictor member 130 and the vane 132 may be initially positioned as shown in FIG. 15A. In this position, the restrictor member 130 is in a closed position, where the flow of exhaled air along the exhalation path through the chamber inlet 104 is substantially restricted. As such, an exhalation pressure at the chamber inlet 104 begins to increase when a user exhales into the mouthpiece 108. As the exhalation pressure at the chamber inlet 104 increases, a corresponding force acting on the face 140 of the restrictor member 130 increases. As previously explained, because the center 144 of the face 140 is offset from the plane defined by the radial offset and the shaft 134, a resulting net force creates a negative or opening torque about the shaft. In turn, the opening torque biases the restrictor member 130 to rotate open, letting exhaled air enter the first chamber 114, and biases the vane 132 away from its first position. As the restrictor member 130 opens and exhaled air is let into the first chamber 114, the pressure at the chamber inlet 104 begins to decrease, the force acting on the face 140 of the restrictor member begins to decrease, and the torque biasing the restrictor member 130 open begins to decrease.

As exhaled air continues to enter the first chamber 114 through the chamber inlet 104, it is directed along the exhalation flow path 110 by the housing 102 until it reaches the chamber passage 116 disposed between the first chamber 114 and the second chamber 118. If the OPEP device 100 is being operated without the variable nozzle 136, the exhaled air accelerates through the chamber passage 116 due to the decrease in cross-sectional area to form a jet of exhaled air. Likewise, if the OPEP device 100 is being operated with the variable nozzle 136, the exhaled air accelerates through the orifice 138 of the variable nozzle 136, where the pressure through the orifice 138 causes the side walls 148 of the variable nozzle 136 to flex outward, thereby increasing the size of the orifice 138, as well as the resulting flow of exhaled air therethrough. To the extent some exhaled air leaks out of the V-shaped slits 150 of the variable nozzle 136, it is directed back toward the jet of exhaled air and along the exhalation flow path by the guide walls 120 protruding into the housing 102.

Then, as the exhaled air exits the first chamber 114 through the variable nozzle 136 and/or chamber passage 116 and enters the second chamber 118, it is directed by the vane 132 toward the front section 101 of the housing 102, where it is forced to reverse directions before exiting the OPEP device 100 through the open first chamber exit 106. As a result of the change in direction of the exhaled air toward the front section 101 of the housing 102, a pressure accumulates in the second chamber 118 near the front section 101 of the housing 102, thereby resulting in a force on the adjacent vane 132, and creating an additional negative or opening torque about the shaft 134. The combined opening torques created about the shaft 134 from the forces acting on the face 140 of the restrictor member 130 and the vane 132 cause the restrictor member 130 and the vane 132 to rotate about the shaft 134 from the position shown in FIG. 15A toward the position shown in FIG. 15B.

When the restrictor member 130 and the vane 132 rotate to the position shown in FIG. 15B, the vane 132 crosses the jet of exhaled air exiting the variable nozzle 136 or the chamber passage 116. Initially, the jet of exhaled air exiting the variable nozzle 136 or chamber passage 116 provides a force on the vane 132 that, along with the momentum of the vane 132, the shaft 134, and the restrictor member 130, propels the vane 132 and the restrictor member 130 to the position shown in FIG. 15C. However, around the position shown in FIG. 15B, the force acting on the vane 132 from the exhaled air exiting the variable nozzle 136 also switches from a negative or opening torque to a positive or closing torque. More specifically, as the exhaled air exits the first chamber 114 through the variable nozzle 136 and enters the second chamber 118, it is directed by the vane 132 toward the front section 101 of the housing 102, where it is forced to reverse directions before exiting the OPEP device 100 through the open second chamber exit 108. As a result of the change in direction of the exhaled air toward the front section 101 of the housing 102, a pressure accumulates in the second chamber 118 near the front section 101 of the housing 102, thereby resulting in a force on the adjacent vane 132, and creating a positive or closing torque about the shaft 134. As the vane 132 and the restrictor member 130 continue to move closer to the position shown in FIG. 15C, the pressure accumulating in the section chamber 118 near the front section 101 of the housing 102, and in turn, the positive or closing torque about the shaft 134, continues to increase, as the flow of exhaled air along the exhalation flow path 110 and through the chamber inlet 104 is even less restricted. Meanwhile, although the torque about the shaft 134 from the force acting on the restrictor member 130 also switches from a negative or opening torque to a positive or closing torque around the position shown in FIG. 15B, its magnitude is essentially negligible as the restrictor member 130 and the vane 132 rotate from the position shown in FIG. 15B to the position shown in FIG. 15C.

After reaching the position shown in FIG. 15C, and due to the increased positive or closing torque about the shaft 134, the vane 132 and the restrictor member 130 reverse directions and begin to rotate back toward the position shown in FIG. 15B. As the vane 132 and the restrictor member 130 approach the position shown in FIG. 15B, and the flow of exhaled through the chamber inlet 104 is increasingly restricted, the positive or closing torque about the shaft 134 begins to decrease. When the restrictor member 130 and the vane 132 reach the position 130 shown in FIG. 15B, the vane 132 crosses the jet of exhaled air exiting the variable nozzle 136 or the chamber passage 116, thereby creating a force on the vane 132 that, along with the momentum of the vane 132, the shaft 134, and the restrictor member 130, propels the vane 132 and the restrictor member 130 back to the position shown in FIG. 15A. After the restrictor member 130 and the vane 132 return to the position shown in FIG. 15A, the flow of exhaled air through the chamber inlet 104 is restricted, and the cycle described above repeats itself.

It should be appreciated that, during a single period of exhalation, the cycle described above will repeat numerous times. Thus, by repeatedly moving the restrictor member 130 between a closed position, where the flow of exhaled air through the chamber inlet 104 is restricted, and an open position, where the flow of exhaled air through the chamber inlet 104 is less restricted, an oscillating back pressure is transmitted to the user of the OPEP device 100 and OPEP therapy is administered.

Figure 17:
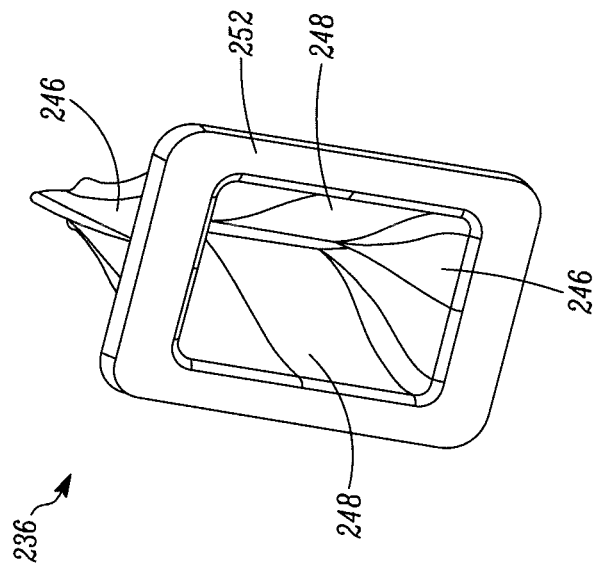
FIG. 17 is a rear perspective view of the variable nozzle of FIG. 16 shown without the flow of exhaled air therethrough.
Figure 16:
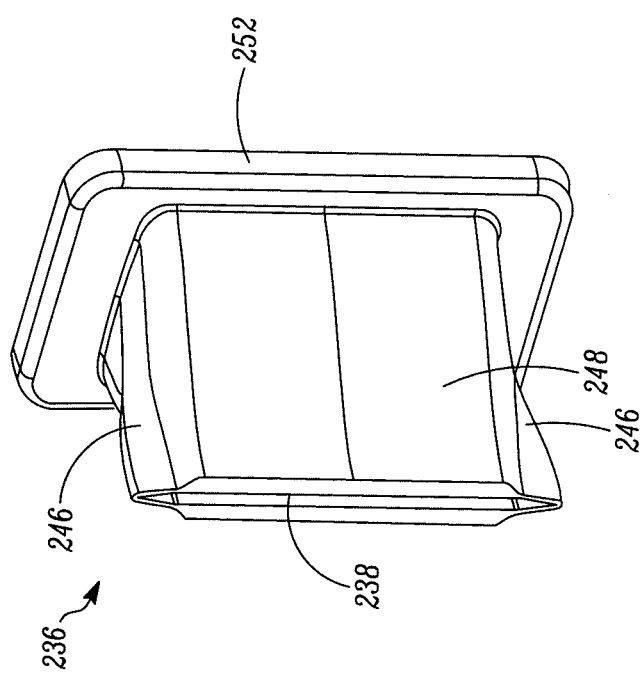
FIG. 16 is a front perspective view of a different embodiment of a variable nozzle shown without the flow of exhaled air therethrough.

Turning now to FIGS. 16-17, an alternative embodiment of a variable nozzle 236 is shown. The variable nozzle 236 may be used in the OPEP device 100 as an alternative to the variable nozzle 136 described above. As shown in FIGS. 16-17, the variable nozzle 236 includes an orifice 238, top and bottom walls 246, side walls 248, and a lip 252 configured to mount the variable nozzle 236 within the housing of the OPEP device 100 between the first chamber 114 and the second chamber 118 in the same manner as the variable nozzle 136. Similar to the variable nozzle 136 shown in FIGS. 12-13, the variable nozzle 236 may be constructed or molded of any material having a suitable flexibility, such as silicone.

During the administration of OPEP therapy, as the orifice 238 of the variable nozzle 236 opens in response to the flow of exhaled air therethrough, the cross-sectional shape of the orifice 238 remains generally rectangular, which results in a lower drop in pressure through the variable nozzle 236 from the first chamber 114 to the second chamber 118. The generally consistent rectangular shape of the orifice 238 of the variable nozzle 236 during increased flow rates is achieved by thin, creased walls formed in the top and bottom walls 246, which allow the side walls 248 to flex easier and with less resistance. A further advantage of this embodiment is that there is no leakage out of the top and bottom walls 246 while exhaled air flows through the orifice 238 of the variable nozzle 236, such as for example, through the V-shaped slits 150 of the variable nozzle 136 shown in FIGS. 12-13.

Those skilled in the art will also appreciate that, in some applications, only positive expiratory pressure (without oscillation) may be desired, in which case the OPEP device 100 may be operated without the restrictor member 130, but with a fixed orifice or manually adjustable orifice instead. The positive expiratory pressure embodiment may also comprise the variable nozzle 136, or the variable nozzle 236, in order to maintain a relatively consistent back pressure within a desired range.

Second OPEP Embodiment

Figure 18:
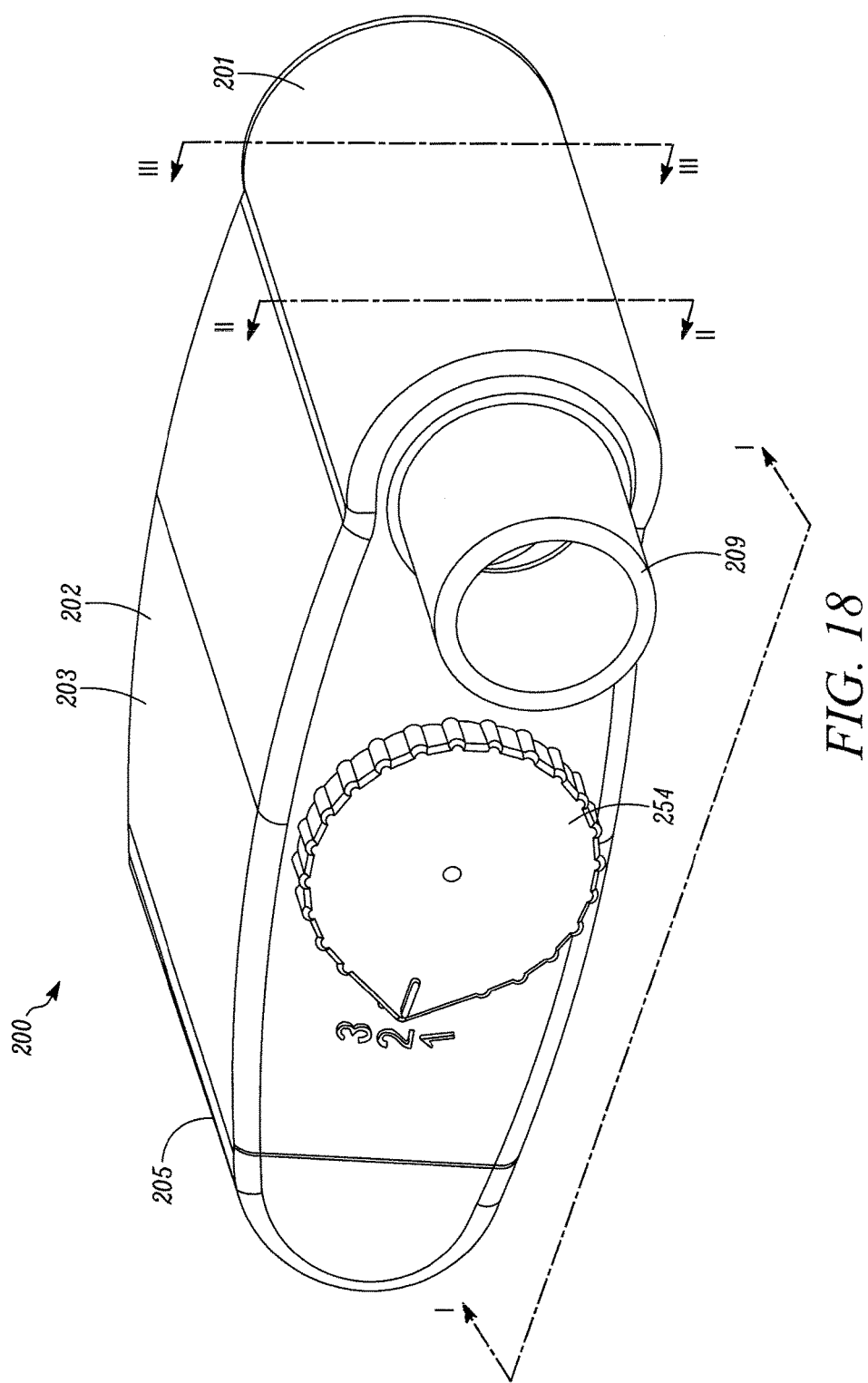
FIG. 18 is a front perspective view of a second embodiment of an OPEP device.
Figure 19:
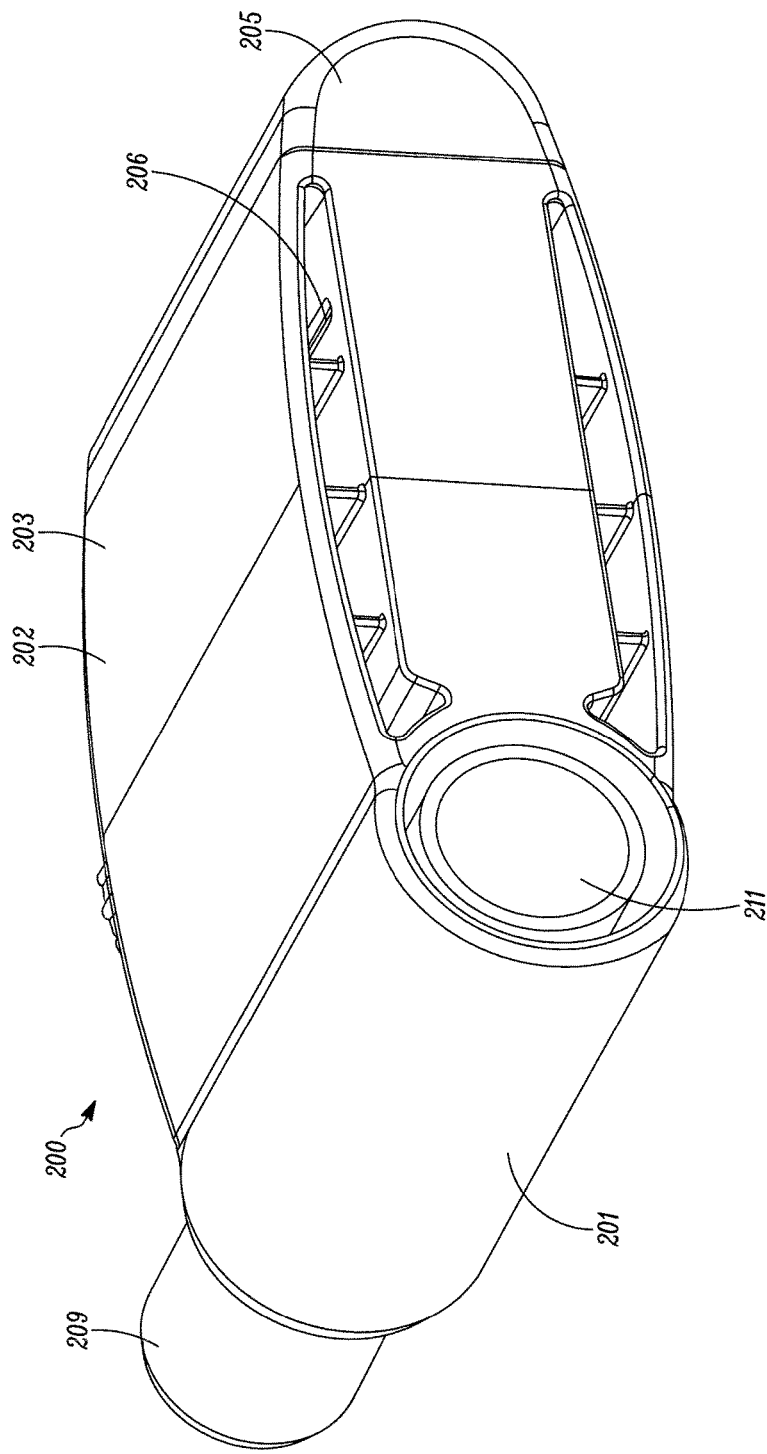
FIG. 19 is a rear perspective view of the OPEP device of FIG. 18.

Turning now to FIGS. 18-19, a front perspective view and a rear perspective view of a second embodiment of an OPEP device 200 is shown. The configuration and operation of the OPEP device 200 is similar to that of the OPEP device 100. However, as best shown in FIGS. 20-24, the OPEP device 200 further includes an adjustment mechanism 253 adapted to change the relative position of the chamber inlet 204 with respect to the housing 202 and the restrictor member 230, which in turn changes the range of rotation of the vane 232 operatively connected thereto. As explained below, a user is therefore able to conveniently adjust both the frequency and the amplitude of the OPEP therapy administered by the OPEP device 200 without opening the housing 202 and disassembling the components of the OPEP device 200.

The OPEP device 200 generally comprises a housing 202, a chamber inlet 204, a first chamber outlet 206 (best seen in FIGS. 23 and 32), a second chamber outlet 208 (best seen in FIGS. 23 and 32), and a mouthpiece 209 in fluid communication with the chamber inlet 204. As with the OPEP device 100, a front section 201, a middle section 203, and a rear section 205 of the housing 202 are separable so that the components contained therein can be periodically accessed, cleaned, replaced, or reconfigured, as required to maintain the ideal operating conditions. The OPEP device also includes an adjustment dial 254, as described below.

As discussed above in relation to the OPEP device 100, the OPEP device 200 may be adapted for use with other or additional interfaces, such as an aerosol delivery device. In this regard, the OPEP device 200 is equipped with an inhalation port 211 (best seen in FIGS. 19, 21, and 23) in fluid communication with the mouthpiece 209 and the chamber inlet 204. As noted above, the inhalation port may include a separate one-way valve (not shown) to permit a user of the OPEP device 200 both to inhale the surrounding air through the one-way valve and to exhale through the chamber inlet 204 without withdrawing the mouthpiece 209 of the OPEP device 200 between periods of inhalation and exhalation. In addition, the aforementioned aerosol delivery devices may be connected to the inhalation port 211 for the simultaneous administration of aerosol and OPEP therapies.

Figure 20:
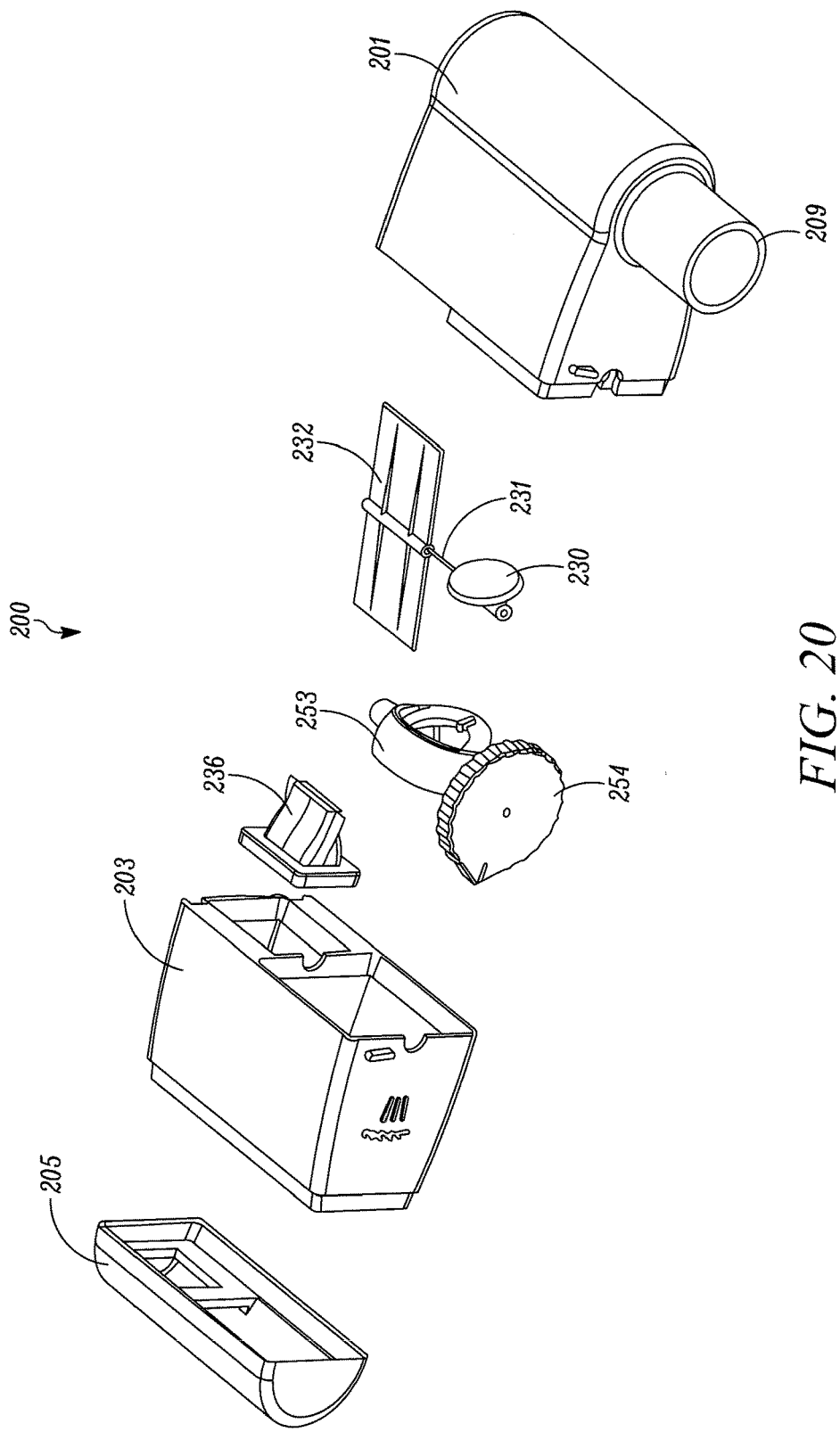
FIG. 20 is an exploded view of the OPEP device of FIG. 18, shown with the internal components of the OPEP device.

An exploded view of the OPEP device 200 is shown in FIG. 20. In addition to the components of the housing described above, the OPEP device 200 includes a restrictor member 230 operatively connected to a vane 232 by a pin 231, an adjustment mechanism 253, and a variable nozzle 236. As shown in the cross-sectional view of FIG. 21, when the OPEP device 200 is in use, the variable nozzle 236 is positioned between the middle section 203 and the rear section 205 of the housing 202, and the adjustment mechanism 253, the restrictor member 230, and the vane 232 form an assembly.

Figure 21:
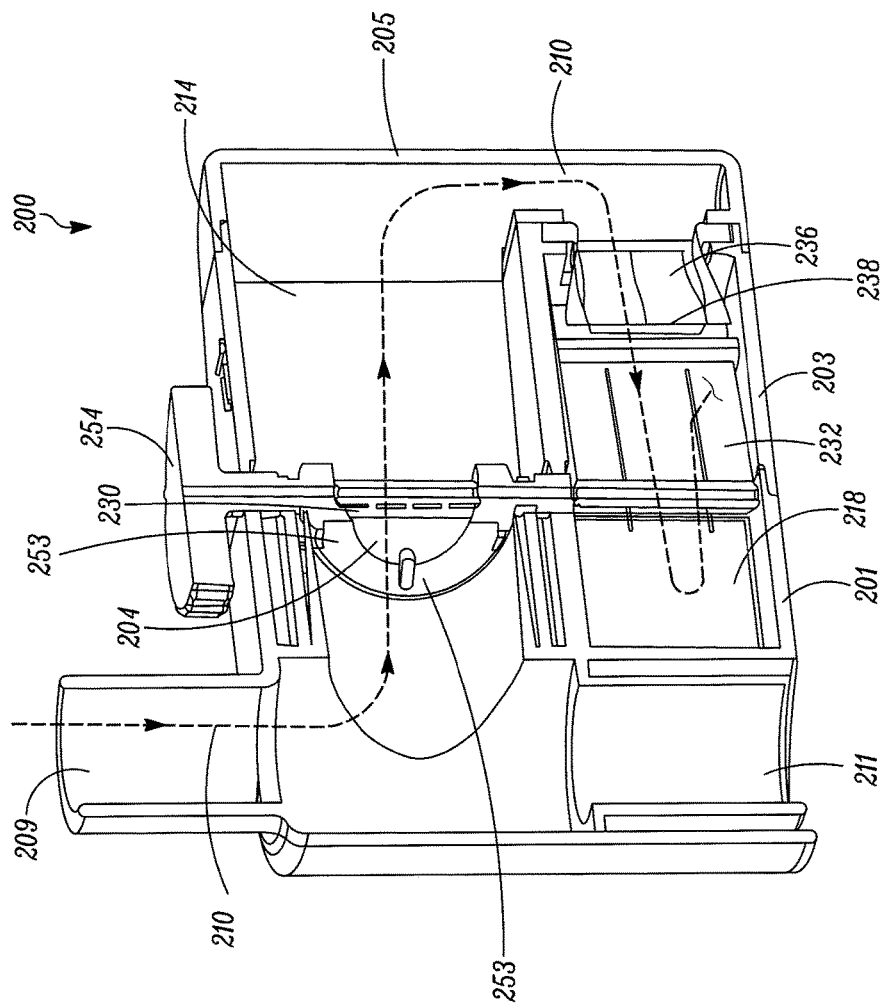
FIG. 21 is a cross-sectional view taken along line I in FIG. 18 of the OPEP device, shown with the internal components of the OPEP device.
Figure 22:
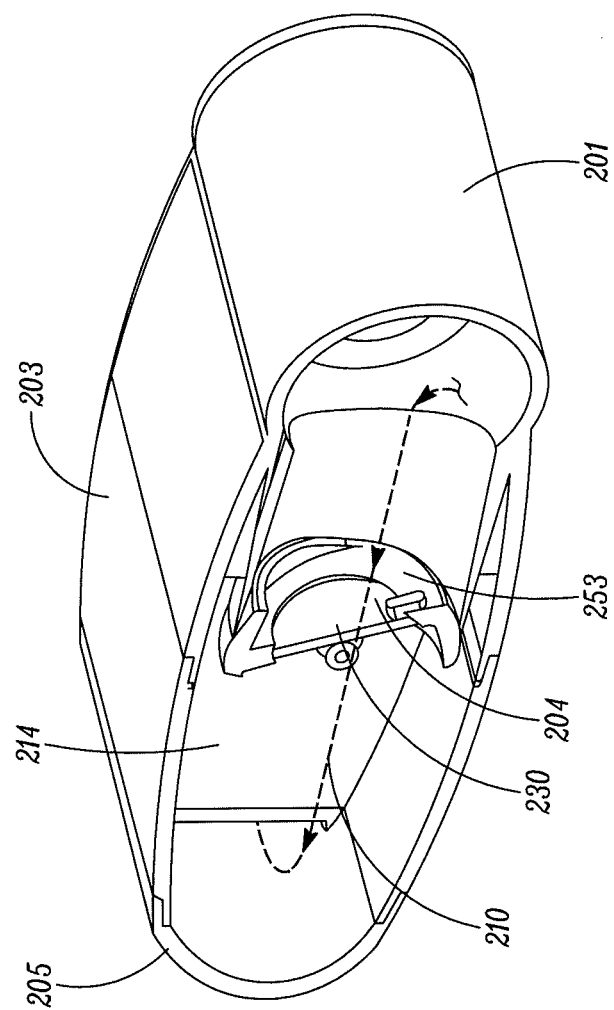
FIG. 22 is a cross-sectional view taken along line II in FIG. 18 of the OPEP device, shown with the internal components of the OPEP device.
Figure 23:
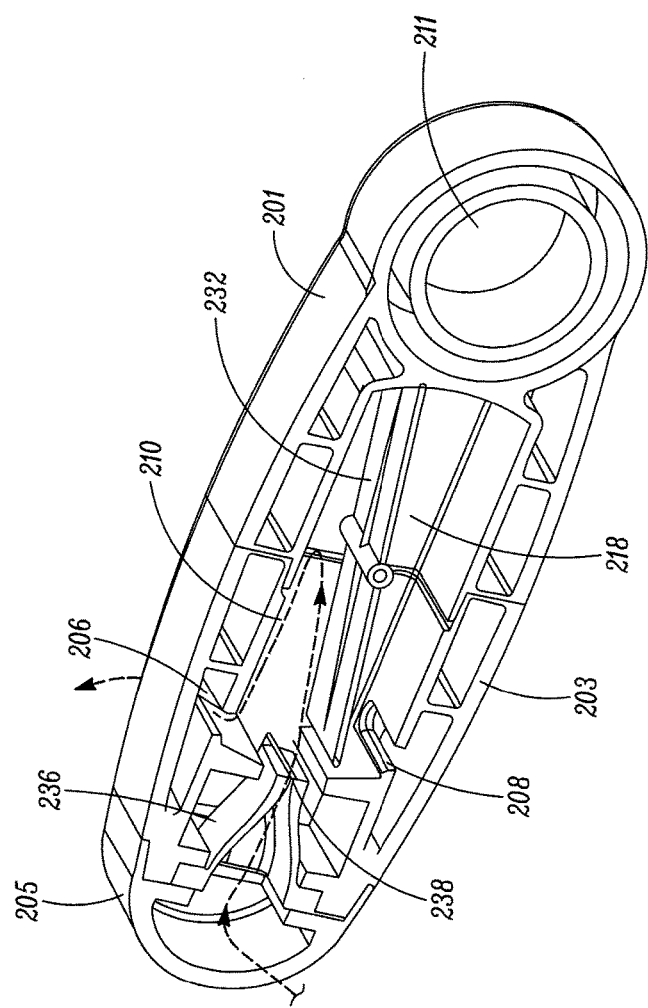
FIG. 23 is a cross-sectional view taken along line III in FIG. 18 of the OPEP device, shown with the internal components of the OPEP device.

Turning to FIGS. 21-23, various cross-sectional perspective views of the OPEP device 200 are shown. As with the OPEP device 100, an exhalation flow path 210, identified by a dashed line, is defined between the mouthpiece 209 and at least one of the first chamber outlet 206 and the second chamber outlet 208 (best seen in FIGS. 23 and 32). As a result of a one-way valve (not-shown) and/or an aerosol delivery device (not shown) attached to the inhalation port 211, the exhalation flow path 210 begins at the mouthpiece 209 and is directed toward the chamber inlet 204, which in operation may or may not be blocked by the restrictor member 230. After passing through the chamber inlet 204, the exhalation flow path 210 enters a first chamber 214 and makes a 180° turn toward the variable nozzle 236. After passing through the orifice 238 of the variable nozzle 236, the exhalation flow path 210 enters a second chamber 218. In the second chamber 218, the exhalation flow path 210 may exit the OPEP device 200 through at least one of the first chamber outlet 206 or the second chamber outlet 208. Those skilled in the art will appreciate that the exhalation flow path 210 identified by the dashed line is exemplary, and that air exhaled into the OPEP device 200 may flow in any number of directions or paths as it traverses from the mouthpiece 209 or chamber inlet 204 to the first chamber outlet 206 or the second chamber outlet 208.

Figure 25:
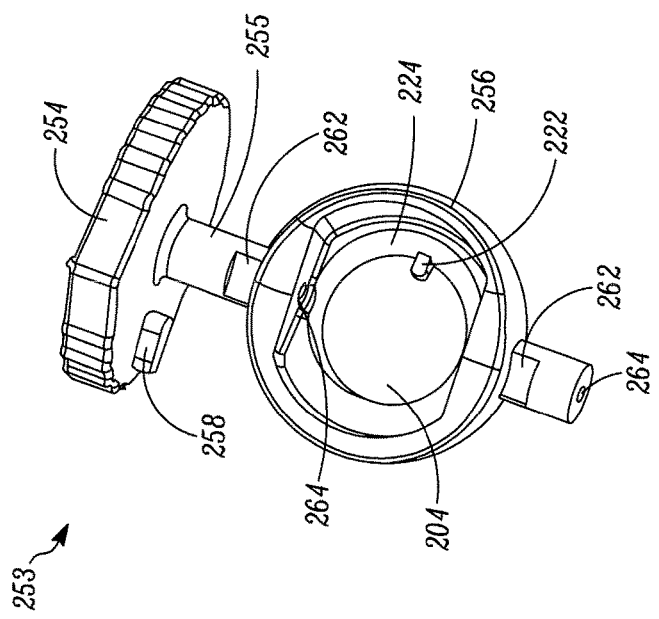
FIG. 25 is a rear perspective view of the adjustment mechanism of FIG. 24.
Figure 24:
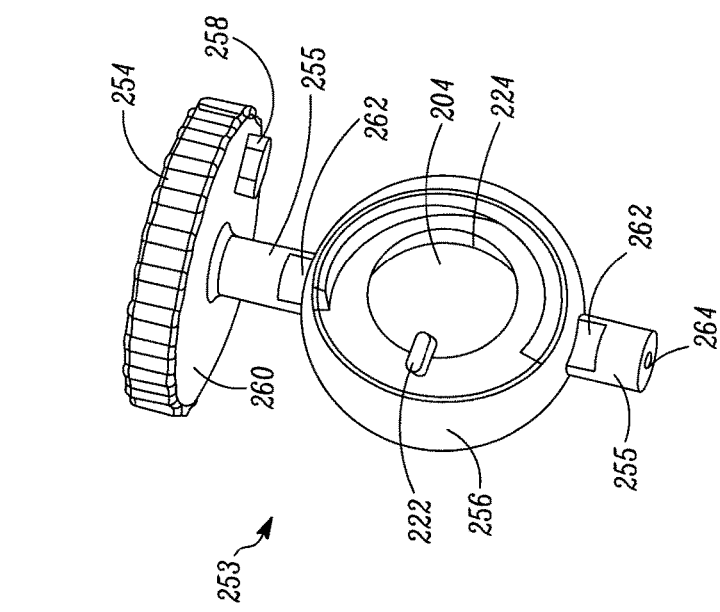
FIG. 24 is a front perspective view of an adjustment mechanism of the OPEP device of FIG. 18.

Referring to FIGS. 24-25, front and rear perspective views of the adjustment mechanism 253 of the OPEP device 200 are shown. In general, the adjustment mechanism 253 includes an adjustment dial 254, a shaft 255, and a frame 256. A protrusion 258 is positioned on a rear face 260 of the adjustment dial, and is adapted to limit the selective rotation of the adjustment mechanism 253 by a user, as further described below. The shaft 255 includes keyed portions 262 adapted to fit within upper and lower bearings 226, 228 formed in the housing 200 (see FIGS. 21 and 28-29). The shaft further includes an axial bore 264 configured to receive the pin 231 operatively connecting the restrictor member 230 and the vane 232. As shown, the frame 256 is spherical, and as explained below, is configured to rotate relative to the housing 202, while forming a seal between the housing 202 and the frame 256 sufficient to permit the administration of OPEP therapy. The frame 256 includes a circular opening defined by a seat 224 adapted to accommodate the restrictor member 230. In use, the circular opening functions as the chamber inlet 204. The frame 256 also includes a stop 222 for preventing the restrictor member 230 from opening in a wrong direction.

Figure 26:
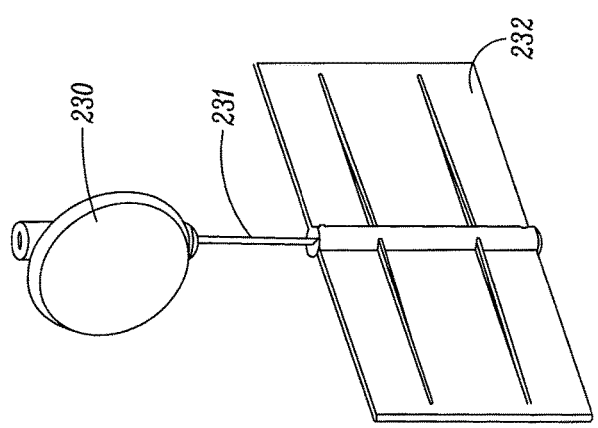
FIG. 26 is a front perspective view of a restrictor member operatively connected to a vane for use in the OPEP device of FIG. 18.

Turning to FIG. 26, a front perspective view of the restrictor member 230 and the vane 232 is shown. The design, materials, and configuration of the restrictor member 230 and the vane 232 may be the same as described above in regards to the OPEP device 100. However, the restrictor member 230 and the vane 232 in the OPEP device 200 are operatively connected by a pin 231 adapted for insertion through the axial bore 264 in the shaft 255 of the adjustment mechanism 253. The pin 231 may be constructed, for example, by stainless steel. In this way, rotation of the restrictor member 230 results in a corresponding rotation of the vane 232, and vice versa.

Figure 27:
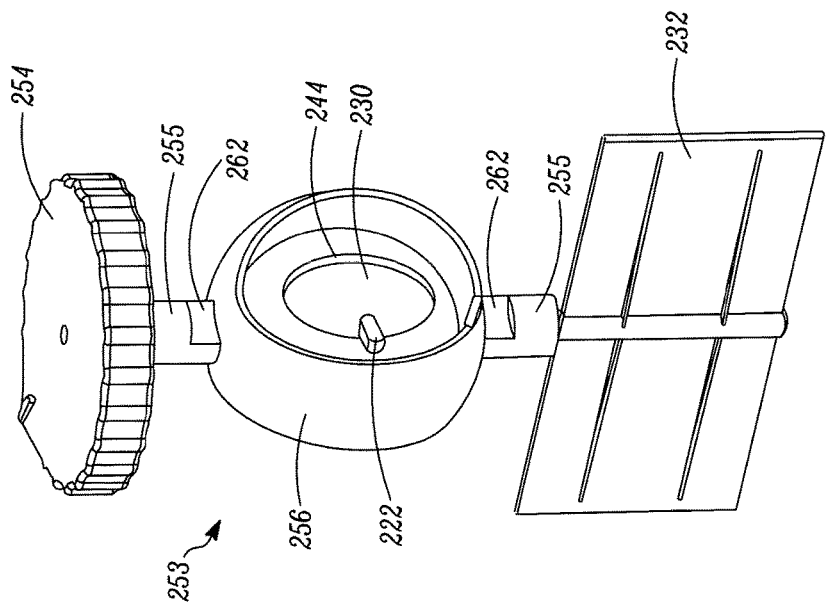
FIG. 27 is a front perspective view of the adjustment mechanism of FIG. 24 assembled with the restrictor member and the vane of FIG. 26.

Turning to FIG. 27, a front perspective view of the adjustment mechanism 253 assembled with the restrictor member 230 and the vane 232 is shown. In this configuration, it can be seen that the restrictor member 230 is positioned such that it is rotatable relative to the frame 256 and the seat 224 between a closed position (as shown), where a flow of exhaled air along the exhalation flow path 210 through the chamber inlet 204 is restricted, and an open position (not shown), where the flow of exhaled air through the chamber inlet 204 is less restricted. As previously mentioned the vane 232 is operatively connected to the restrictor member 230 by the pin 231 extending through shaft 255, and is adapted to move in unison with the restrictor member 230. It can further be seen that the restrictor member 230 and the vane 232 are supported by the adjustment mechanism 253, which itself is rotatable within the housing 202 of the OPEP device 200, as explained below.

Figure 28:
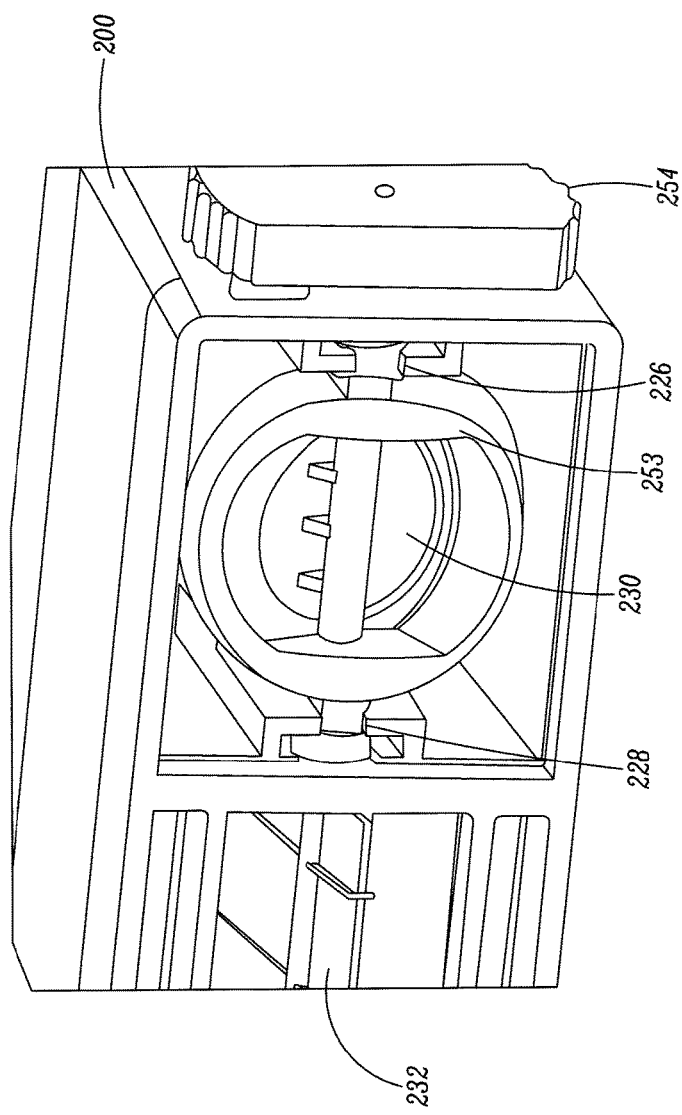
FIG. 28 is a partial cross-sectional view of the assembly of FIG. 27 within the OPEP device of FIG. 18.
Figure 29B:
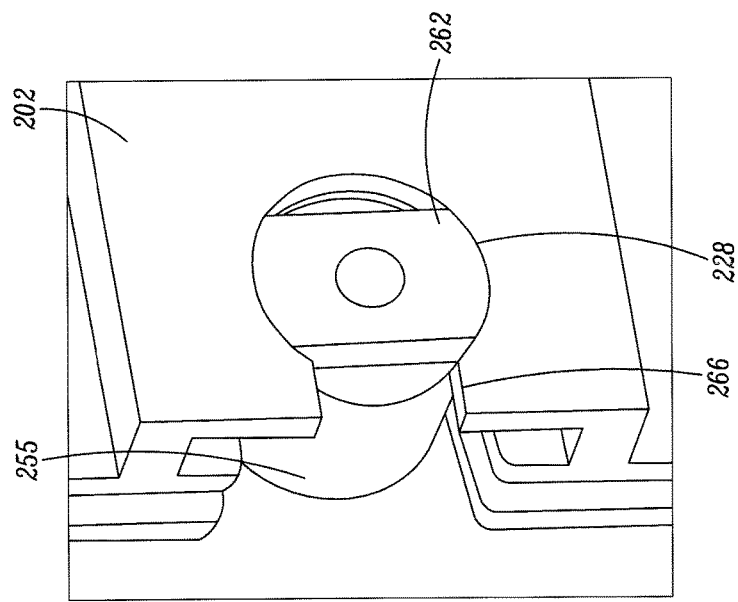
FIGS. 29A-B are partial cross-sectional views illustrating installation of the assembly of FIG. 27 within the OPEP device of FIG. 18.
Figure 29A:
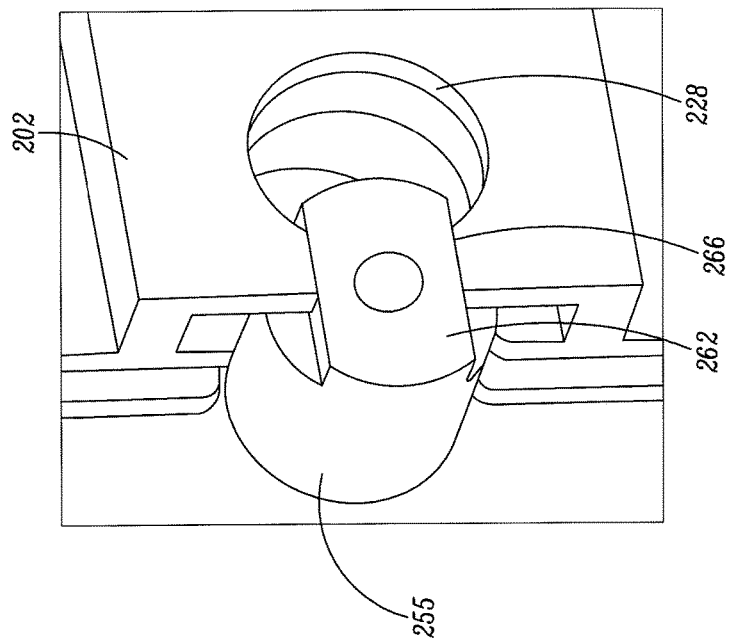

FIGS. 28 and 29A-B are partial cross-sectional views illustrating the adjustment mechanism 253 mounted within the housing 202 of the OPEP device 200. As shown in FIG. 28, the adjustment mechanism 253, as well as the restrictor member 230 and the vane 232, are rotatably mounted within the housing 200 about an upper and lower bearing 226, 228, such that a user is able to rotate the adjustment mechanism 253 using the adjustment dial 254. FIGS. 29A-29B further illustrates the process of mounting and locking the adjustment mechanism 253 within the lower bearing 228 of the housing 202. More specifically, the keyed portion 262 of the shaft 255 is aligned with and inserted through a rotational lock 266 formed in the housing 202, as shown in FIG. 29A. Once the keyed portion 262 of the shaft 255 is inserted through the rotational lock 266, the shaft 255 is rotated 90° to a locked position, but remains free to rotate. The adjustment mechanism 253 is mounted and locked within the upper bearing 226 in the same manner.

Figure 30:
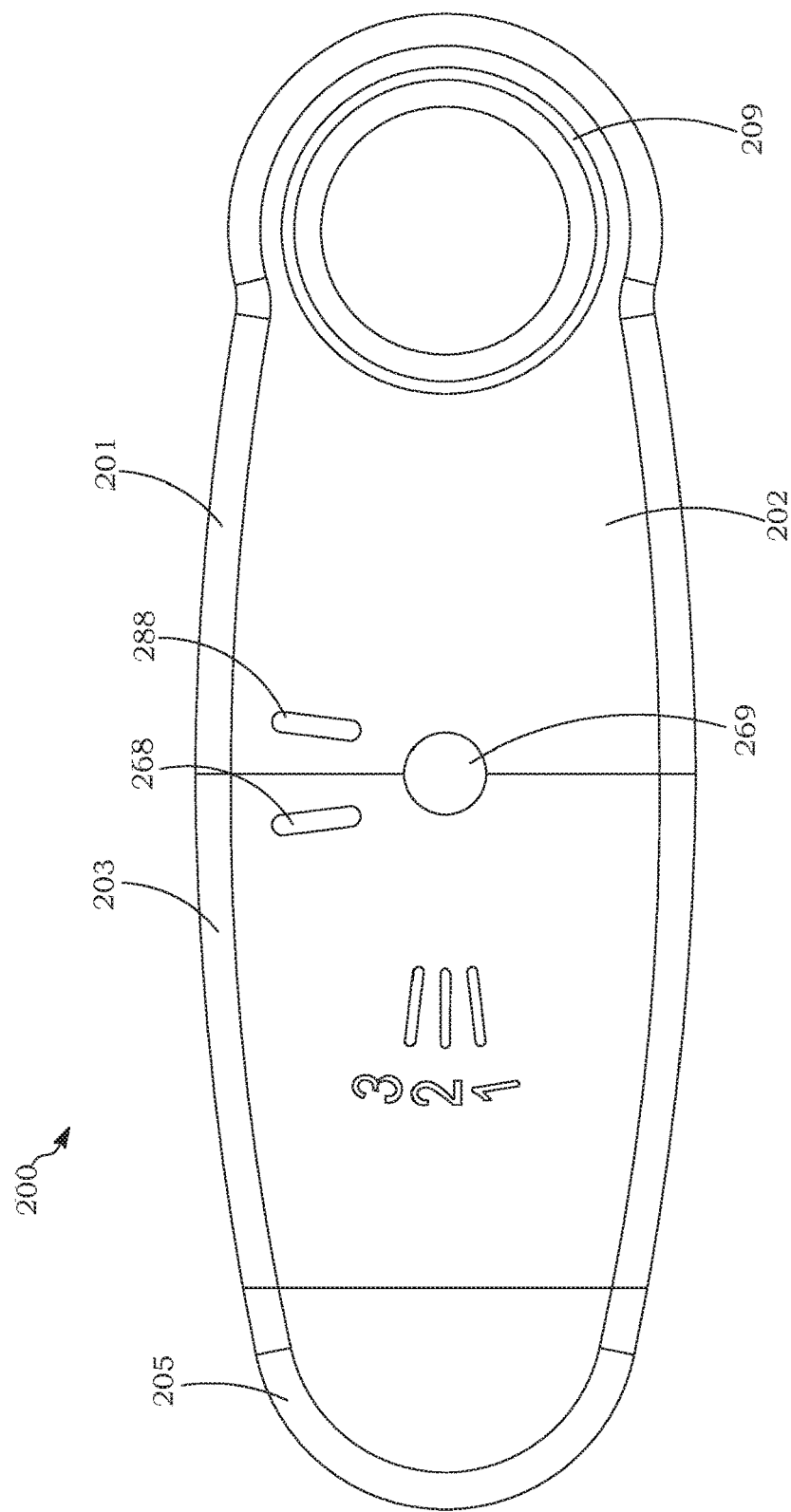
FIG. 30 is a front view of the OPEP device of FIG. 18 illustrating an aspect of the adjustability of the OPEP device.

Once the housing 200 and the internal components of the OPEP device 200 are assembled, the rotation of the shaft 255 is restricted to keep it within a locked position in the rotational lock 266. As shown in a front view of the OPEP device 200 in FIG. 30, two stops 268, 288 are positioned on the housing 202 such that they engage the protrusion 258 formed on the rear face 260 of the adjustment dial 254 when a user rotates the adjustment dial 254 to a predetermined position. For purposes of illustration, the OPEP device 200 is shown in FIG. 30 without the adjustment dial 254 or the adjustment mechanism 253, which would extend from the housing 202 through an opening 269. In this way, rotation of the adjustment dial 254, the adjustment mechanism 253, and the keyed portion 262 of the shaft 255 can be appropriately restricted.

Figure 31:
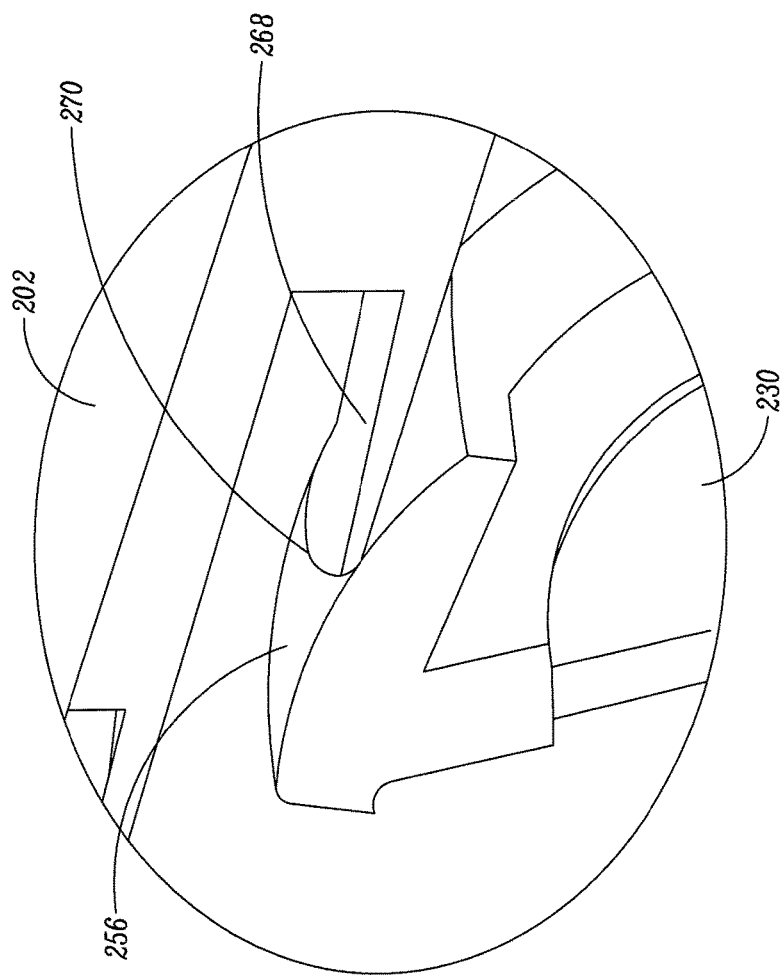
FIG. 31 is a partial cross-sectional view of the assembly of FIG. 27 within the OPEP device of FIG. 18.

Turning to FIG. 31, a partial cross-sectional view of the adjustment mechanism 253 mounted within the housing 200 is shown. As previously mentioned, the frame 256 of the adjustment mechanism 253 is spherical, and is configured to rotate relative to the housing 202, while forming a seal between the housing 202 and the frame 256 sufficient to permit the administration of OPEP therapy. As shown in FIG. 31, a flexible cylinder 271 extending from the housing 202 completely surrounds a portion of the frame 256 to form a sealing edge 270. Like the housing 202 and the restrictor member 230, the flexible cylinder 271 and the frame 256 may be constructed of a low shrink, low friction plastic. One such material is acetal. In this way, the sealing edge 270 contacts the frame 256 for a full 360° and forms a seal throughout the permissible rotation of the adjustment member 253.

Figure 32B:
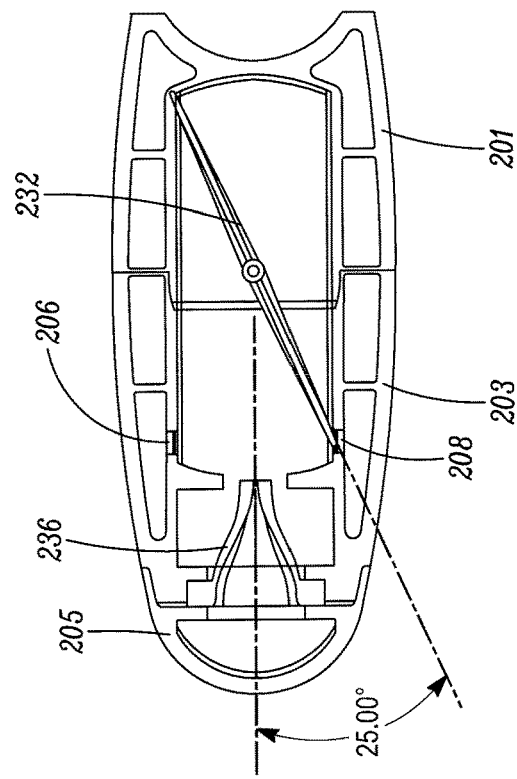
FIGS. 32A-B are partial cross-sectional views taken along line III in FIG. 18 of the OPEP device, illustrating possible configurations of the OPEP device.
Figure 32A:
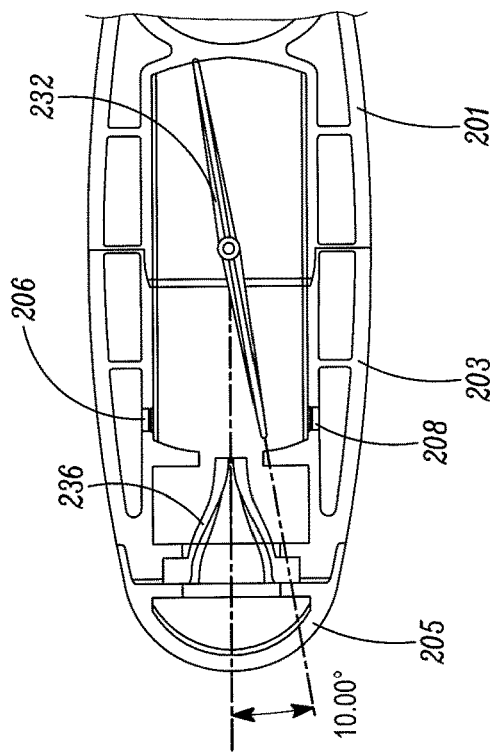
Figure 33B:
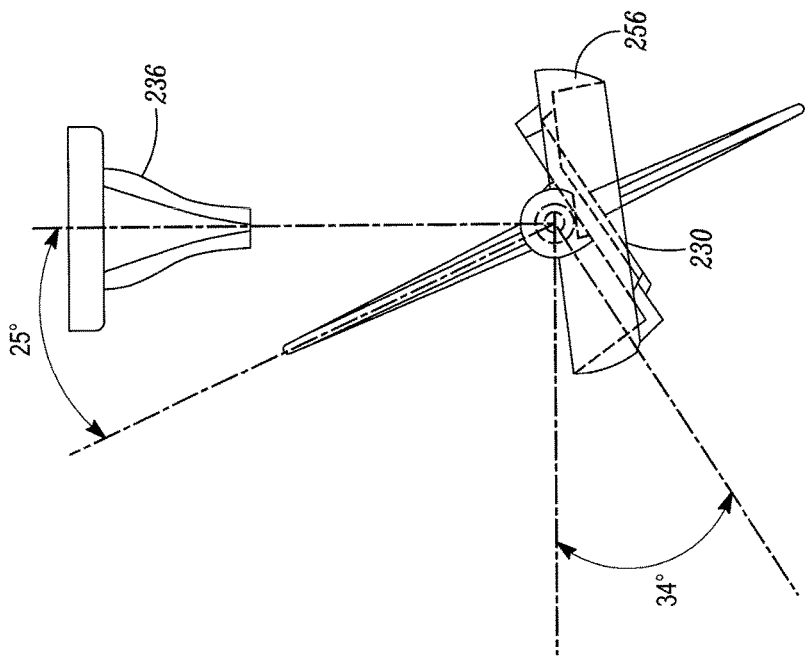
FIGS. 33A-B are top phantom views illustrating the adjustability of the OPEP device of FIG. 18.
Figure 33A:
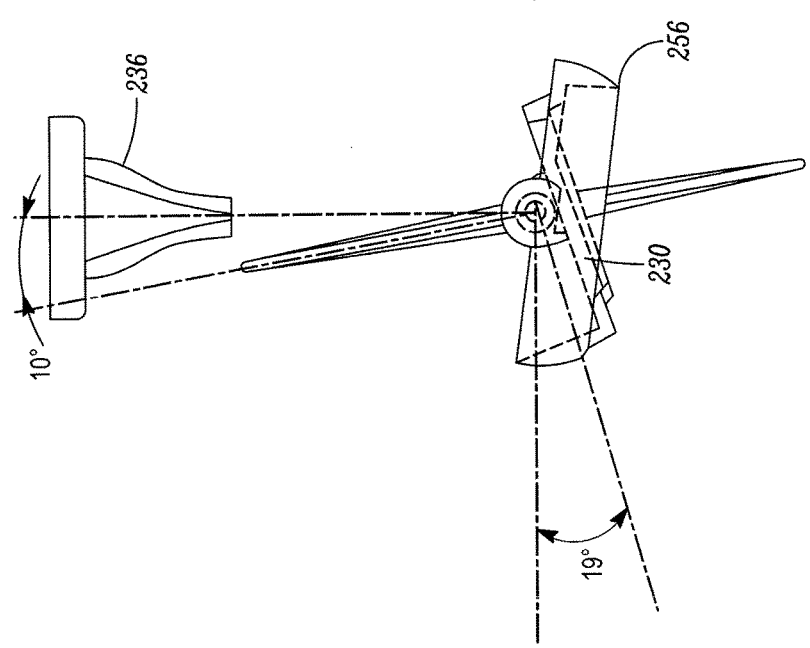

The selective adjustment of the OPEP device 200 will now be described with reference to FIGS. 32A-B, 33A-B, and 34A-B. FIGS. 32A-B are partial cross-sectional views of the OPEP device 200; FIGS. 33A-B are illustrations of the adjustability of the OPEP device 200; and, FIGS. 34A-B are top phantom views of the OPEP device 200. As previously mentioned with regards to the OPEP device 100, it is preferable that the vane 232 and the restrictor member 230 are configured such that when the OPEP device 200 is fully assembled, the angle between a centerline of the variable nozzle 236 and the vane 232 is between 10° and 25° when the restrictor member 230 is in a closed position. However, it should be appreciated that the adjustability of the OPEP device 200 is not limited to the parameters described herein, and that any number of configurations may be selected for purposes of administering OPEP therapy within the ideal operating conditions.

FIG. 32A shows the vane 232 at an angle of 10° from the centerline of the variable nozzle 236, whereas FIG. 32B shows the vane 232 at an angle of 25° from the centerline of the variable nozzle 236. FIG. 33A illustrates the necessary position of the frame 256 (shown in phantom) relative to the variable nozzle 236 such that the angle between a centerline of the variable nozzle 236 and the vane 232 is 10° when the restrictor member 230 is in the closed position. FIG. 33B, on the other hand, illustrates the necessary position of the frame 256 (shown in phantom) relative to the variable nozzle 236 such that the angle between a centerline of the variable nozzle 236 and the vane 232 is 25° when the restrictor member 230 is in the closed position.

Referring to FIGS. 34A-B, side phantom views of the OPEP device 200 are shown. The configuration shown in FIG. 34A corresponds to the illustrations shown in FIGS. 32A and 33A, wherein the angle between a centerline of the variable nozzle 236 and the vane 232 is 10° when the restrictor member 230 is in the closed position. FIG. 34B, on the other hand, corresponds to the illustrations shown in FIGS. 32B and 33B, wherein the angle between a centerline of the variable nozzle 236 and the vane 232 is 25° when the restrictor member 230 is in the closed position. In other words, the frame 256 of the adjustment member 253 has been rotated counter-clockwise 15°, from the position shown in FIG. 34A, to the position shown in FIG. 34B, thereby also increasing the permissible rotation of the vane 232.

In this way, a user is able to rotate the adjustment dial 254 to selectively adjust the orientation of the chamber inlet 204 relative to the restrictor member 230 and the housing 202. For example, a user may increase the frequency and amplitude of the OPEP therapy administered by the OPEP device 200 by rotating the adjustment dial 254, and therefore the frame 256, toward the position shown in FIG. 34A. Alternatively, a user may decrease the frequency and amplitude of the OPEP therapy administered by the OPEP device 200 by rotating the adjustment dial 254, and therefore the frame 256, toward the position shown in FIG. 34B. Furthermore, as shown for example in FIGS. 18 and 30, indicia may be provided to aid the user in the setting of the appropriate configuration of the OPEP device 200.

Operating conditions similar to those described below with reference to the OPEP device 800 may also be achievable for an OPEP device according to the OPEP device 200.

Third OPEP Embodiment

Figure 35:
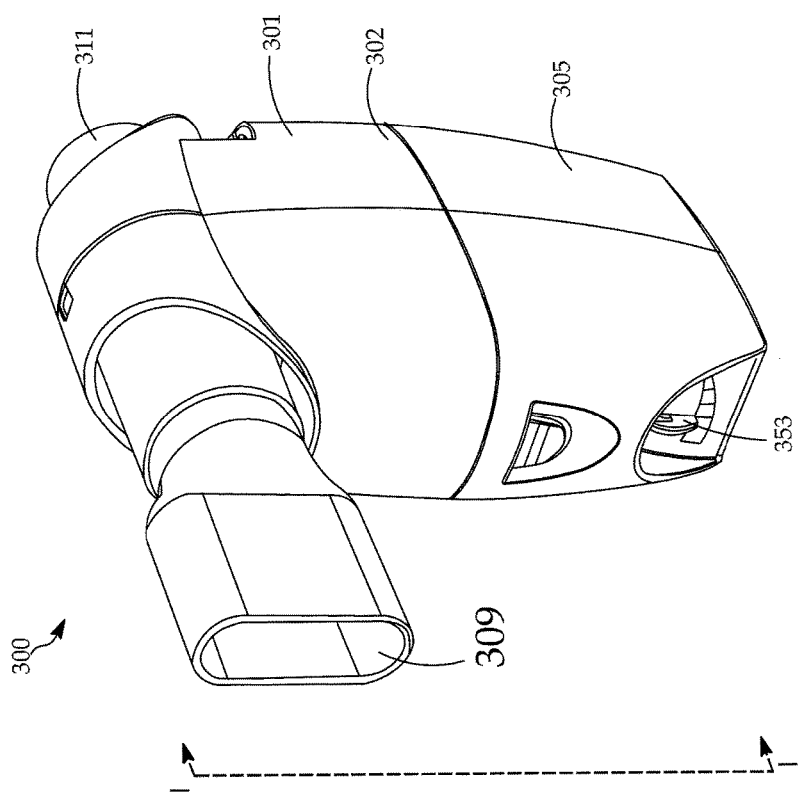
FIG. 35 is a front perspective view of another embodiment of an OPEP device.
Figure 36:
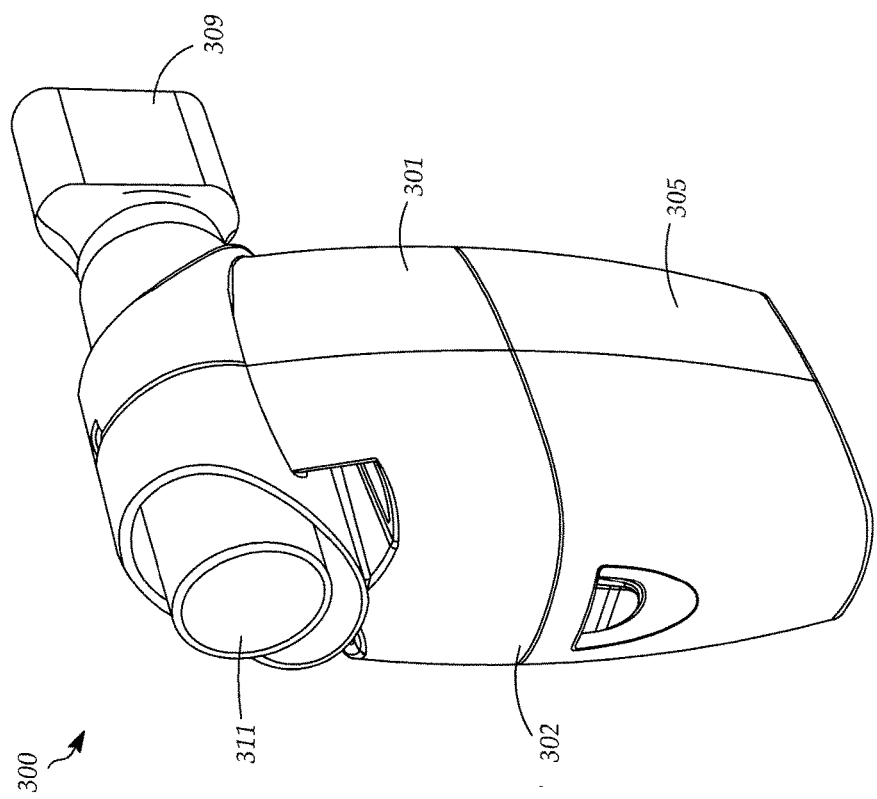
FIG. 36 is a rear perspective view of the OPEP device of FIG. 35.
Figure 37:
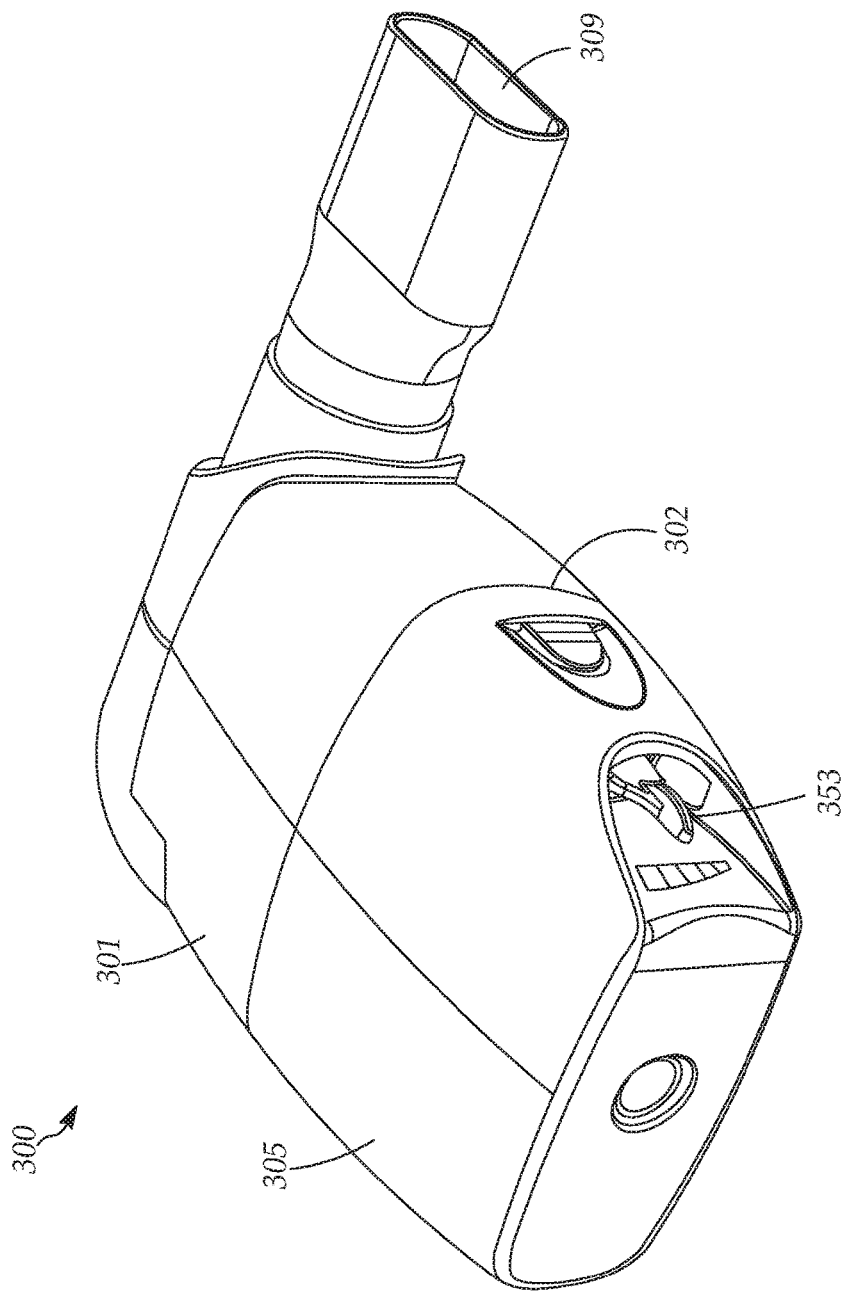
FIG. 37 is a perspective view of the bottom of the OPEP device of FIG. 35.

Turning to FIGS. 35-37, another embodiment of an OPEP device 300 is shown. The OPEP device 300 is similar to that of the OPEP device 200 in that is selectively adjustable. As best seen in FIGS. 35, 37, 40, and 49, the OPEP device 300, like the OPEP device 300, includes an adjustment mechanism 353 adapted to change the relative position of a chamber inlet 304 with respect to a housing 302 and a restrictor member 330, which in turn changes the range of rotation of a vane 332 operatively connected thereto. As previously explained with regards to the OPEP device 200, a user is therefore able to conveniently adjust both the frequency and the amplitude of the OPEP therapy administered by the OPEP device 300 without opening the housing 302 and disassembling the components of the OPEP device 300. The administration of OPEP therapy using the OPEP device 300 is otherwise the same as described above with regards to the OPEP device 100.

The OPEP device 300 comprises a housing 302 having a front section 301, a rear section 305, and an inner casing 303. As with the previously described OPEP devices, the front section 301, the rear section 305, and the inner casing 303 are separable so that the components contained therein can be periodically accessed, cleaned, replaced, or reconfigured, as required to maintain the ideal operating conditions. For example, as shown in FIGS. 35-37, the front section 301 and the rear section 305 of the housing 302 are removably connected via a snap fit engagement.

Figure 38:
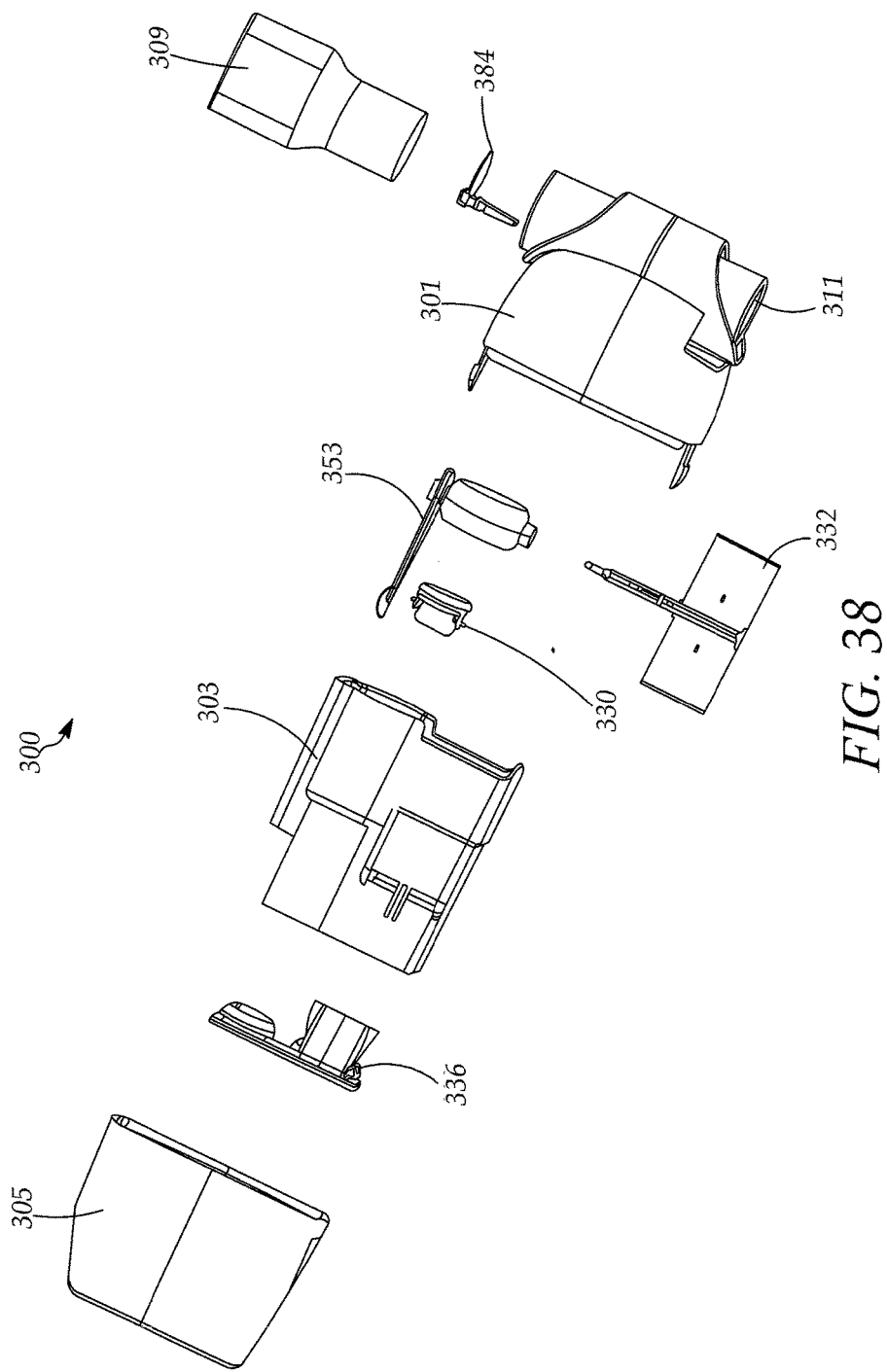
FIG. 38 is an exploded view of the OPEP device of FIG. 35.

The components of the OPEP device 300 are further illustrated in the exploded view of FIG. 38. In general, in addition to the front section 301, the rear section 305, and the inner casing 303, the OPEP device 300 further comprises a mouthpiece 309, an inhalation port 311, a one-way valve 384 disposed therebetween, an adjustment mechanism 353, a restrictor member 330, a vane 332, and a variable nozzle 336.

Figure 39:
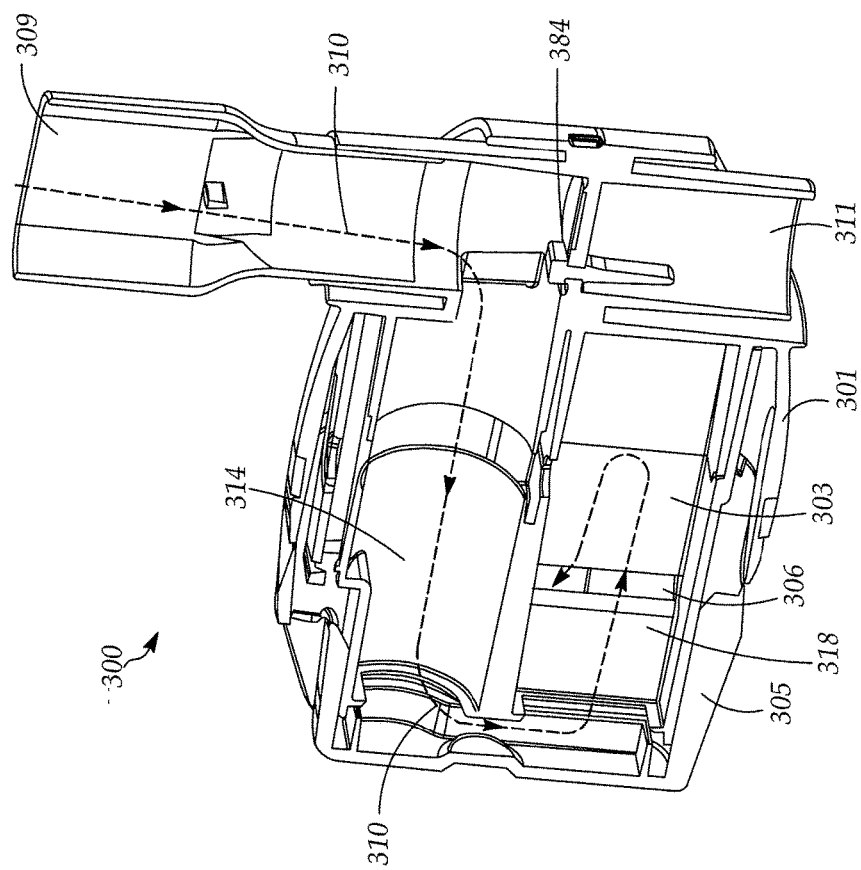
FIG. 39 is a cross-sectional view taken along line I in FIG. 35, shown without the internal components of the OPEP device.
Figure 40:
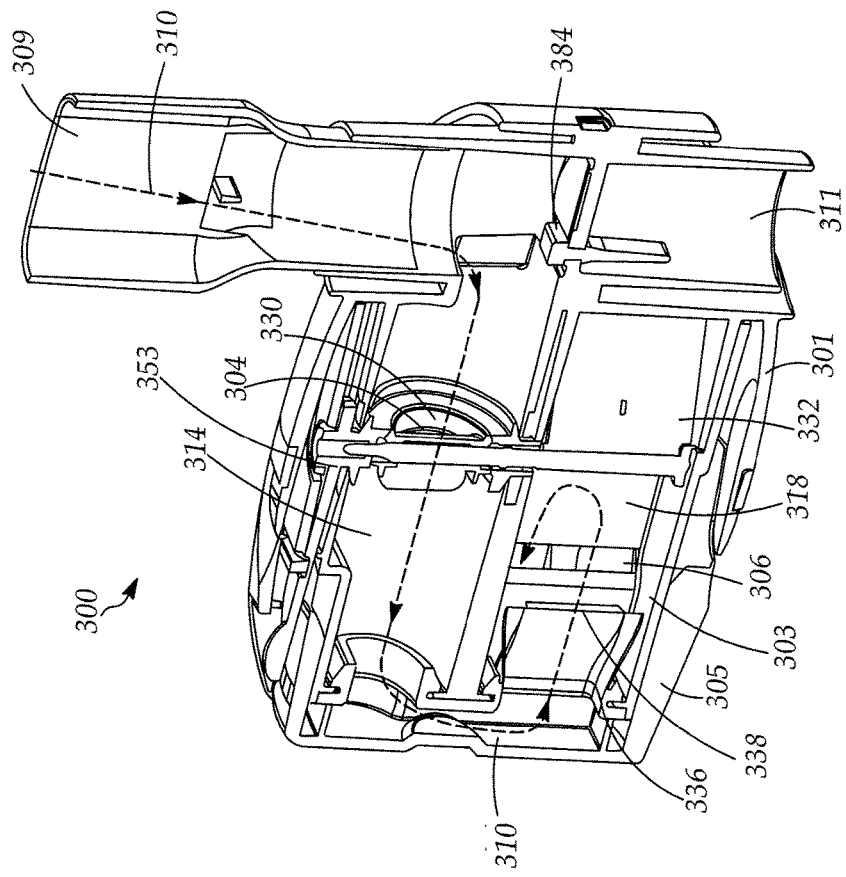
FIG. 40 is a cross-sectional view taken along line I in FIG. 35, shown with the internal components of the OPEP device.
Figure 41:
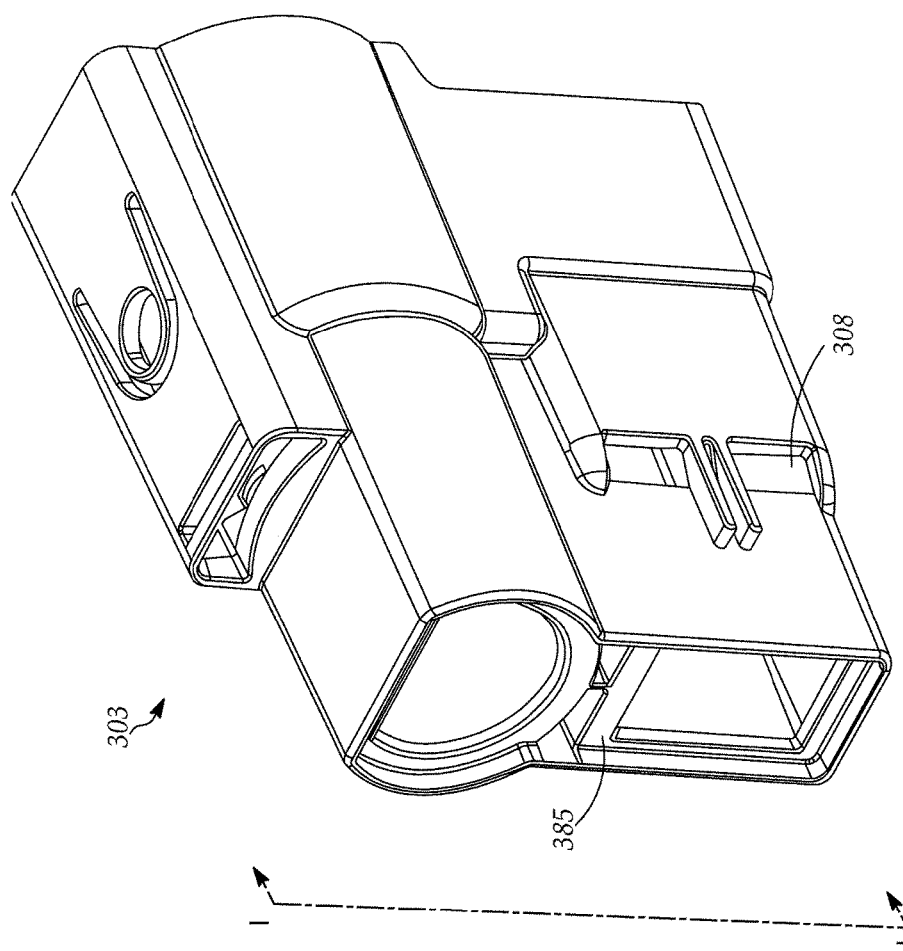
FIG. 41 is a front-perspective view of an inner casing of the OPEP device of FIG. 35.
Figure 42:
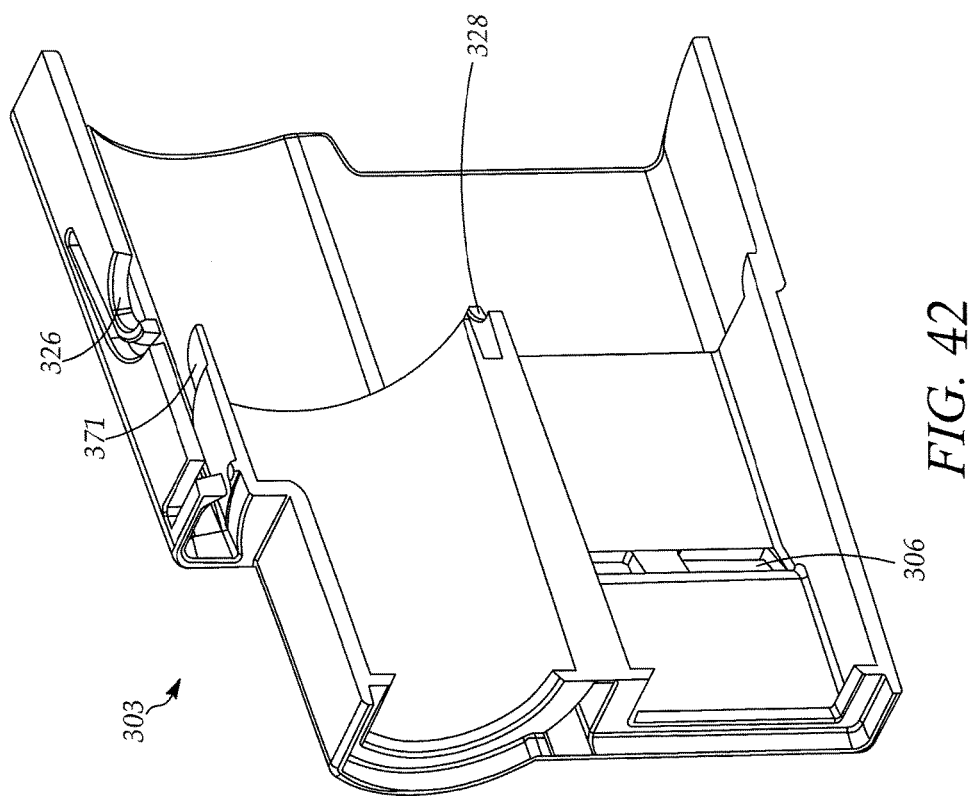
FIG. 42 is a cross-sectional view of the inner casing taken along line I of in FIG. 41.

As seen in FIGS. 39-40, the inner casing 303 is configured to fit within the housing 302 between the front section 301 and the rear section 305, and partially defines a first chamber 314 and a second chamber 318. The inner casing 303 is shown in further detail in the perspective and cross sectional views shown in FIGS. 41-42. A first chamber outlet 306 and a second chamber outlet 308 are formed within the inner casing 303. One end 385 of the inner casing 303 is adapted to receive the variable nozzle 336 and maintain the variable nozzle 336 between the rear section 305 and the inner casing 303. An upper bearing 326 and a lower bearing 328 for supporting the adjustment mechanism 353 is formed, at least in part, within the inner casing 303. Like the flexible cylinder 271 and sealing edge 270 described above with regards to the OPEP device 200, the inner casing 303 also includes a flexible cylinder 371 with a sealing edge 370 for engagement about a frame 356 of the adjustment mechanism 353.

Figure 43:
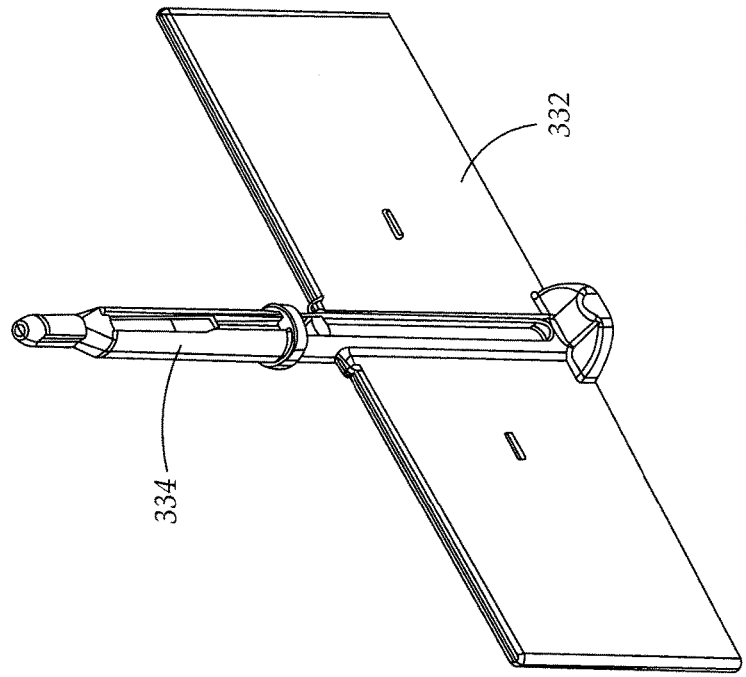
FIG. 43 is a perspective view of a vane of the OPEP device of FIG. 35.

The vane 332 is shown in further detail in the perspective view shown in FIG. 43. A shaft 334 extends from the vane 332 and is keyed to engage a corresponding keyed portion within a bore 365 of the restrictor member 330. In this way, the shaft 334 operatively connects the vane 332 with the restrictor member 330 such that the vane 332 and the restrictor member 330 rotate in unison.

Figure 44:
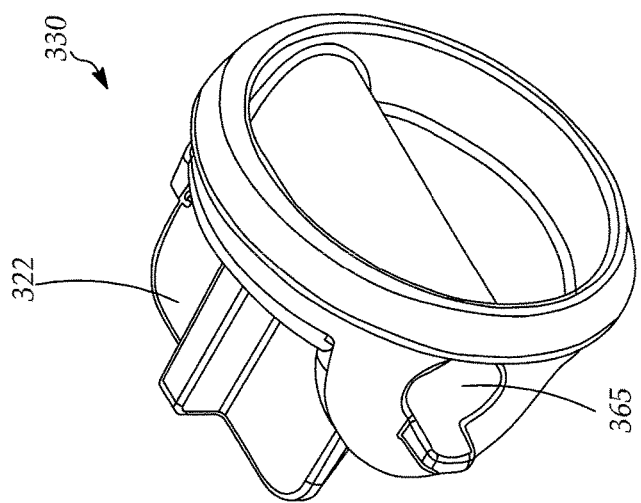
FIG. 44 is a front perspective view of a restrictor member of the OPEP device of FIG. 35.

The restrictor member 330 is shown in further detail in the perspective views shown in FIGS. 44-45. The restrictor member 330 includes a keyed bore 365 for receiving the shaft 334 extending from the vane 332, and further includes a stop 322 that limits permissible rotation of the restrictor member 330 relative to a seat 324 of the adjustment member 353. As shown in the front view of FIG. 46, like the restrictor member 330, the restrictor member 330 further comprises an offset designed to facilitate movement of the restrictor member 330 between a closed position and an open position. More specifically, a greater surface area of the face 340 of the restrictor member 330 is positioned on one side of the bore 365 for receiving the shaft 334 than on the other side of the bore 365. As described above with regards to the restrictor member 130, this offset produces an opening torque about the shaft 334 during periods of exhalation.

Figure 48:
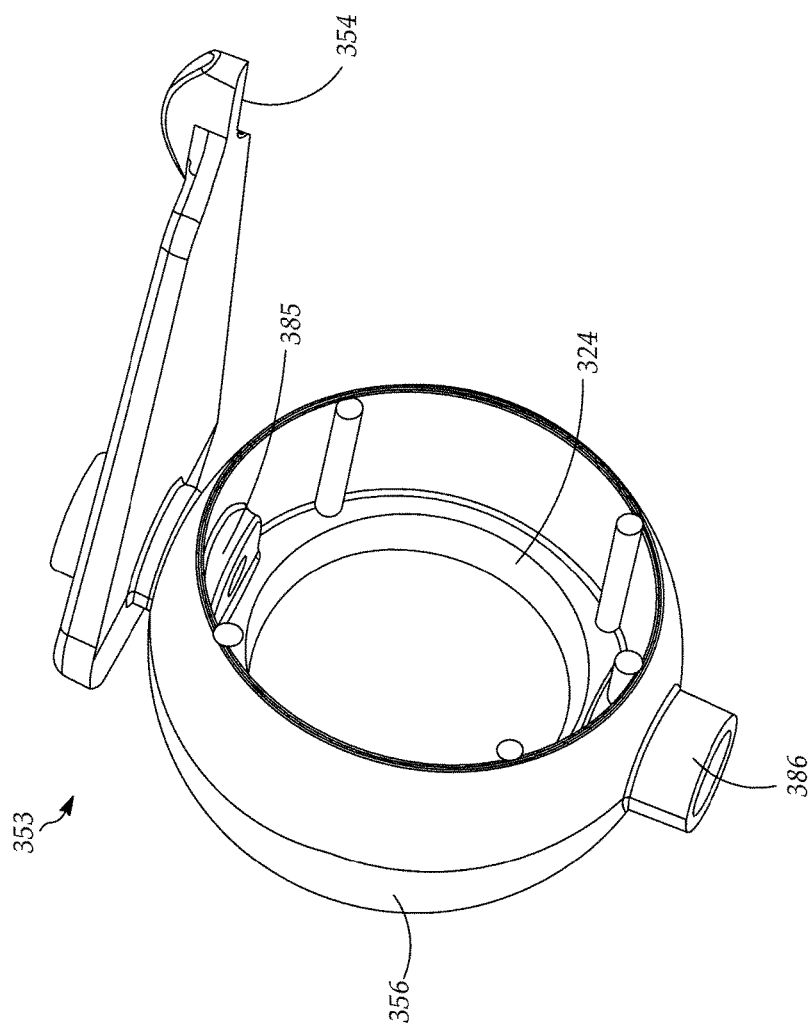
FIG. 48 is a rear perspective view of the adjustment mechanism of FIG. 47.

The adjustment mechanism 353 is shown in further detail in the front and rear perspective views of FIGS. 47 and 48. In general, the adjustment mechanism includes a frame 356 adapted to engage the sealing edge 370 of the flexible cylinder 371 formed on the inner casing 303. A circular opening in the frame 356 forms a seat 324 shaped to accommodate the restrictor member 330. In this embodiment, the seat 324 also defines the chamber inlet 304. The adjustment mechanism 353 further includes an arm 354 configured to extend from the frame 356 to a position beyond the housing 302 in order to permit a user to selectively adjust the orientation of the adjustment mechanism 353, and therefore the chamber inlet 304, when the OPEP device 300 is fully assembled. The adjustment mechanism 353 also includes an upper bearing 385 and a lower bearing 386 for receiving the shaft 334.

Figure 49:
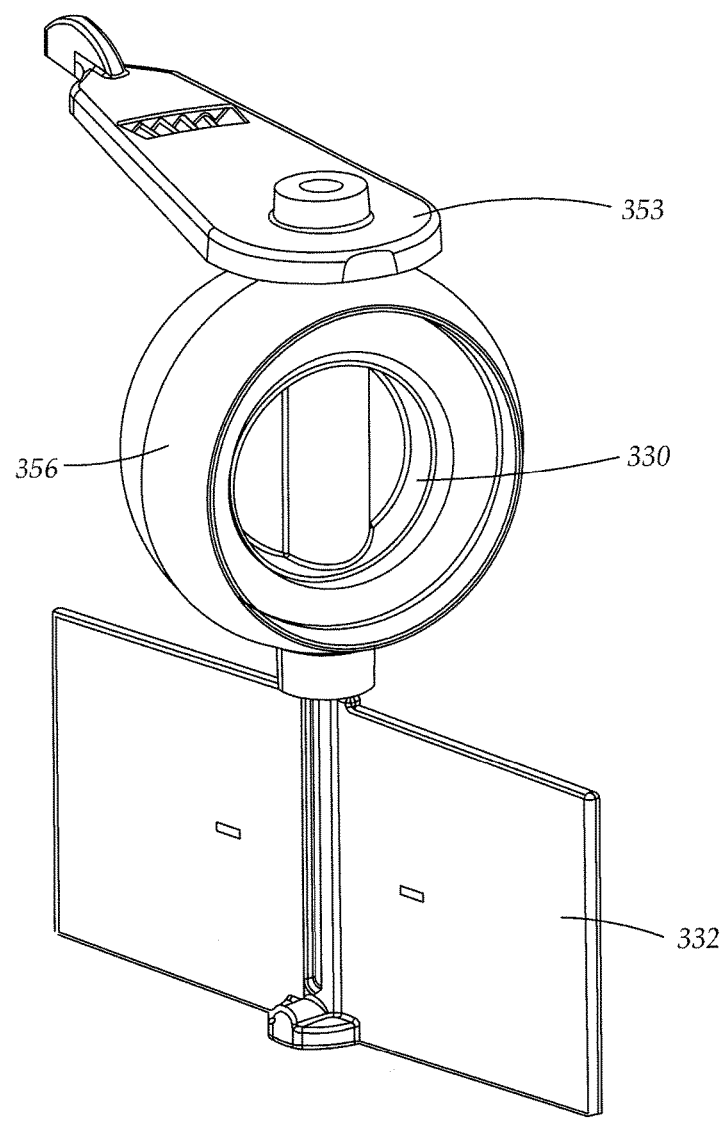
FIG. 49 is a front perspective view of the adjustment mechanism of FIGS. 47-48 assembled with the restrictor member of FIGS. 44-46 and the vane of FIG. 43.
Figure 53:
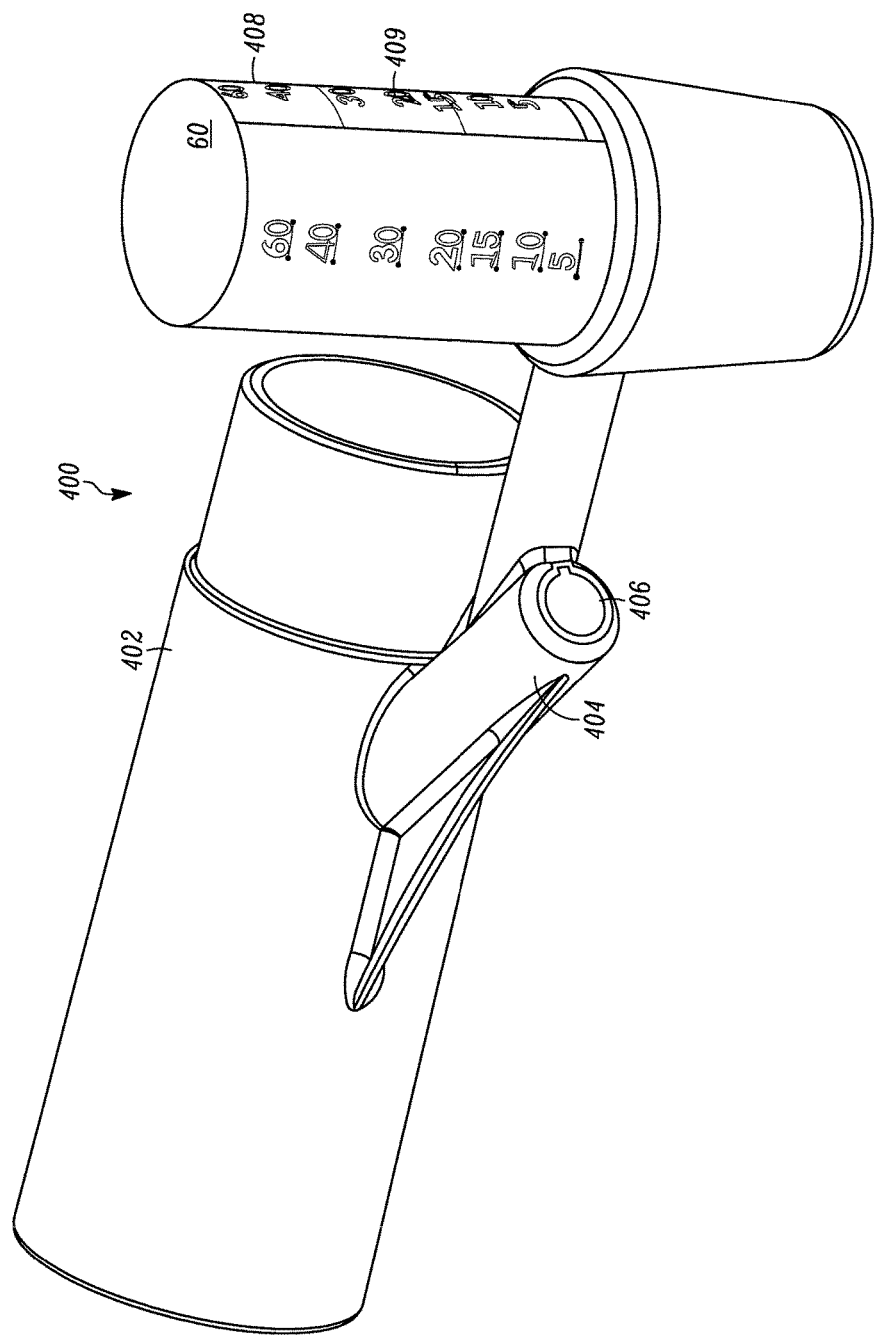
FIG. 53 is a perspective view of a first embodiment of a pressure indicator for an OPEP device.

An assembly of the vane 332, the adjustment mechanism 353, and the restrictor member 330 is shown in the perspective view of FIG. 49. As previously explained, the vane 332 and the restrictor member 330 are operatively connected by the shaft 334 such that rotation of the vane 332 results in rotation of the restrictor member 330, and vice versa. In contrast, the adjustment mechanism 353, and therefore the seat 324 defining the chamber inlet 304, is configured to rotate relative to the vane 332 and the restrictor member 330 about the shaft 334. In this way, a user is able to rotate the arm 354 to selectively adjust the orientation of the chamber inlet 304 relative to the restrictor member 330 and the housing 302. For example, a user may increase the frequency and amplitude of the OPEP therapy administered by the OPEP device 800 by rotating the arm 354, and therefore the frame 356, in a clockwise direction. Alternatively, a user may decrease the frequency and amplitude of the OPEP therapy administered by the OPEP device 300 by rotating the adjustment arm 354, and therefore the frame 356, in a counter-clockwise direction. Furthermore, as shown for example in FIGS. 35 and 37, indicia may be provided on the housing 302 to aid the user in the setting of the appropriate configuration of the OPEP device 300.

The variable nozzle 336 is shown in further detail in the front and rear perspective views of FIGS. 50 and 51. The variable nozzle 336 in the OPEP device 300 is similar to the variable nozzle 236 described above with regards to the OPEP device 200, except that the variable nozzle 336 also includes a base plate 387 configured to fit within one end 385 (see FIGS. 41-42) of the inner casing 303 and maintain the variable nozzle 336 between the rear section 305 and the inner casing 303. Like the variable nozzle 236, the variable nozzle 336 and base plate 387 may be made of silicone.

The one-way valve 384 is shown in further detail in the front perspective view of FIG. 52. In general, the one-way valve 384 comprises a post 388 adapted for mounting in the front section 301 of the housing 302, and a flap 389 adapted to bend or pivot relative to the post 388 in response to a force or a pressure on the flap 389. Those skilled in the art will appreciate that other one-way valves may be used in this and other embodiments described herein without departing from the teachings of the present disclosure. As seen in FIGS. 39-40, the one-way valve 384 may be positioned in the housing 302 between the mouthpiece 309 and the inhalation port 311.

As discussed above in relation to the OPEP device 100, the OPEP device 300 may be adapted for use with other or additional interfaces, such as an aerosol delivery device. In this regard, the OPEP device 300 is equipped with an inhalation port 311 (best seen in FIGS. 35-36 and 38-40) in fluid communication with the mouthpiece 309. As noted above, the inhalation port may include a separate one-way valve 384 (best seen in FIGS. 39-40 and 52) configured to permit a user of the OPEP device 300 both to inhale the surrounding air through the one-way valve 384 and to exhale through the chamber inlet 304, without withdrawing the mouthpiece 309 of the OPEP device 300 between periods of inhalation and exhalation. In addition, the aforementioned commercially available aerosol delivery devices may be connected to the inhalation port 311 for the simultaneous administration of aerosol therapy (upon inhalation) and OPEP therapy (upon exhalation).

The OPEP device 300 and the components described above are further illustrated in the cross-sectional views shown in FIGS. 39-40. For purposes of illustration, the cross-sectional view of FIG. 39 is shown without all the internal components of the OPEP device 300.

The front section 301, the rear section 305, and the inner casing 303 are assembled to form a first chamber 314 and a second chamber 318. As with the OPEP device 100, an exhalation flow path 310, identified by a dashed line, is defined between the mouthpiece 309 and at least one of the first chamber outlet 306 (best seen in FIGS. 39-40 and 42) and the second chamber outlet 308 (best seen in FIG. 41), both of which are formed within the inner casing 303. As a result of the inhalation port 311 and the one-way valve 348, the exhalation flow path 310 begins at the mouthpiece 309 and is directed toward the chamber inlet 304, which in operation may or may not be blocked by the restrictor member 330. After passing through the chamber inlet 304, the exhalation flow path 310 enters the first chamber 314 and makes a 180° turn toward the variable nozzle 336. After passing through an orifice 338 of the variable nozzle 336, the exhalation flow path 310 enters the second chamber 318. In the second chamber 318, the exhalation flow path 310 may exit the second chamber 318, and ultimately the housing 302, through at least one of the first chamber outlet 306 or the second chamber outlet 308. Those skilled in the art will appreciate that the exhalation flow path 310 identified by the dashed line is exemplary, and that air exhaled into the OPEP device 300 may flow in any number of directions or paths as it traverses from the mouthpiece 309 or chamber inlet 304 to the first chamber outlet 306 or the second chamber outlet 308. As previously noted, the administration of OPEP therapy using the OPEP device 300 is otherwise the same as described above with regards to the OPEP device 100.

Solely by way of example, the follow operating conditions, or performance characteristics, may be achieved by an OPEP device according to the OPEP device 300, with the adjustment dial 354 set for increased frequency and amplitude:

| | | |
|---|---|---|
| Flow Rate (lpm) | 10 | 30 |
| Frequency (Hz) | 7 | 20 |
| Upper Pressure (cm H2O) | 13 | 30 |
| Lower Pressure (cm H2O) | 1.5 | 9 |
| Amplitude (cm H2O) | 11.5 | 21 |

The frequency and amplitude may decrease, for example, by approximately 20% with the adjustment dial 354 set for decreased frequency and amplitude. Other frequency and amplitude targets may be achieved by varying the particular configuration or sizing of elements, for example, increasing the length of the vane 332 results in a slower frequency, whereas, decreasing the size of the orifice 338 results in a higher frequency. The above example is merely one possible set of operating conditions for an OPEP device according to the embodiment described above.

Pressure Indicators for OPEP Devices

The medical industry lacks inexpensive, ergonomic, compact, and portable pressure indicator solutions for OPEP devices. For example, most commercially available manometers are large stationary device connectable through tubing, which makes them cumbersome and unattractive. Also, most commercially available manometers are intended to be reusable, which leads to risks of transmitting infectious diseases. Furthermore, existing manometers are not designed or intended to read and provide visual feedback of oscillating pressures, such as those generated in an OPEP device during administration of OPEP therapy. Use of such manometers with OPEP devices leads to excessive fluctuation in the pressure reading output, making it hard for a user of the device, or his or her clinician, to get accurate feedback.

The embodiments described herein provide an ergonomic pressure indicator that is easily integrated with existing OPEP devices, and is suitable for repeated use by a single patient. Furthermore, these embodiments are configured to minimize oscillations in the visual feedback provided to the user, therefore allowing the pressure indicator to display a readable pressure level, and at the same time, provide dynamic visual feedback to the let user know that the OPEP device is working by sensing its oscillating pressures.

While the pressure indicator embodiments described herein are shown and described for use with the OPEP device 300 of FIG. 35, it should be appreciated that the pressure indicators are also suitable for use with other OPEP devices, including for example: other OPEP embodiments described herein; those shown and described in U.S. Pat. Nos. 5,018,517; 6,581,598; 6,776,159; 7,059,324; 8,327,849; 8,539,951; and 8,485,179, the entireties of which are herein incorporated by reference; those shown and described in U.S. patent application Ser. Nos. 13/489,894 and 14/092,091, the entireties of which are herein incorporated by reference; and, any number of commercially available OPEP devices, such as AEROBIKA® from Trudell Medical International of London, Canada, ACAPELLA® from Smiths Medical of St. Paul, Minn., FLUTTER® from Axcan Scandipharm Inc. of Birmingham, Ala., and RC-CORONET® from Curaplex of Dublin, Ohio.

First Embodiment of a Pressure Indicator

Turning to FIGS. 53-56, a first embodiment of a pressure indicator 400 is shown. In general, the pressure indicator 400 includes a body 402, a conduit 404 extending from the body 402, a plug 406 positioned along and inserted into the conduit 404, and an instrument for measuring pressure in the form of a manometer 408 positioned at an outlet of the conduit 404.

The body 402 may be sized and shaped for integration with existing OPEP devices, for example, as shown in FIG. 54, with the mouthpiece 309 of the OPEP device 300. In this example, the body 402 is comprised of 22 mm ISO male/female conical connectors shaped and sized to connect to the mouthpiece 309 of the OPEP device 300.

Extending from the body 402 is a conduit 404 configured to transmit a pressure from within the OPEP device 300 to the manometer 408. An inlet 405 permits a pressure within the body 402 to pass into the conduit 404. As shown, the conduit 404 extends away from the body 402, then angles alongside the OPEP device 300, thereby maintaining the portability and ergonomics of the OPEP device 300, and avoiding the need for lengthy tubing or additional attachments.

The manometer 408 is positioned at an outlet 403 of the conduit 404. It should be appreciated, however, that a portion of the conduit 404 could extend into a passageway in the manometer 408, or other instrument for measuring pressure. The manometer 408 may be a piston-type gauge such as, for example, an AMBU® Disposable Pressure Manometer from Ambu A/S of Copenhagen, Denmark. Other instruments for measuring pressure may also be used in place of the manometer 408. In general, the manometer 408 includes a spring-loaded piston that moves an indicator within the piston in response to a change in pressure. Preferably, the instrument for measuring pressure may comprise one or more of a numerical, color, shape, or other visual indicia, or one or more of a sound or other auditory indicia, or a combination of one or more of each of a visual indicia and an auditory indicia. In one of the exemplary embodiments shown in FIG. 53, the manometer 408 includes a numerical indicia 409 of pressures measured by the manometer 408. Preferably, the instrument for measuring pressure is positioned relative to the respiratory treatment device such that the indicator and indicia are visible to the user during treatment. As shown in the exemplary embodiment in FIG. 54, the manometer 408 is positioned relative to the respiratory treatment device in the form of an OPEP device 300 such that the indicator and indicia 409 are viewable to a user of the OPEP device 300 during treatment.

Figure 56A:
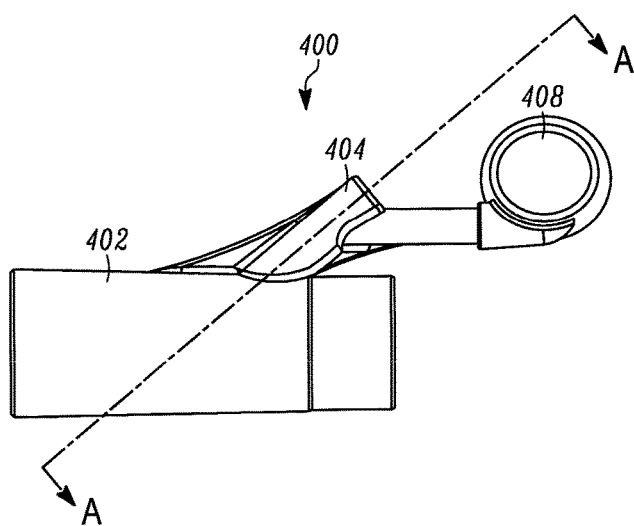
FIGS. 56A-E are top and cross-sectional views of the pressure indicator of FIG. 53.
Figure 56B:
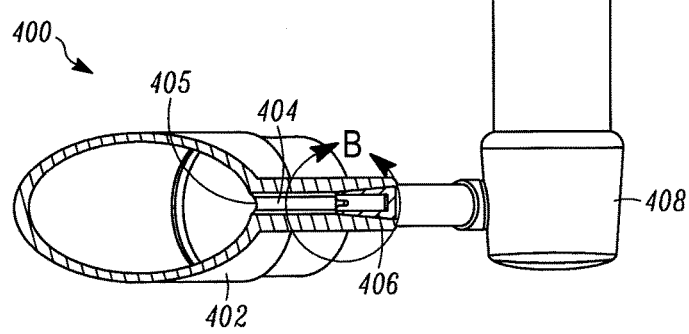
Figure 56C:
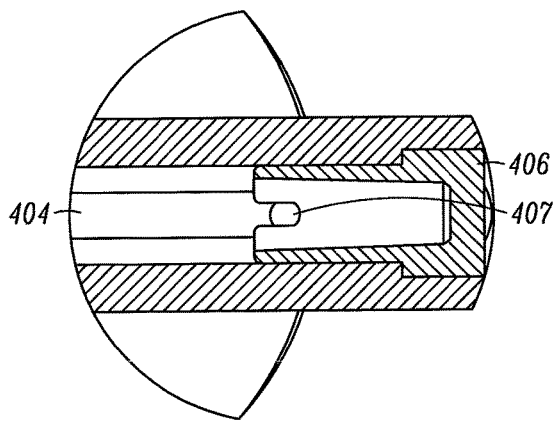
Figure 56D:
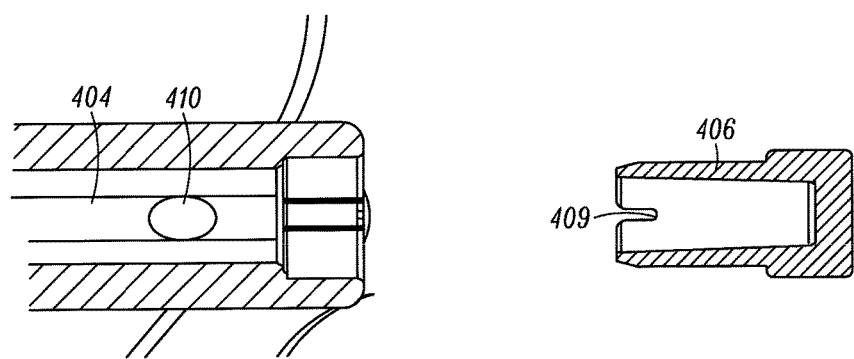
Figure 56E:
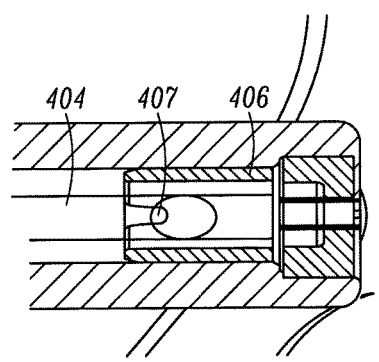

The plug 406 is insertable by press-fitting along the conduit 404 at a point where the conduit 404 angles alongside the OPEP device 300. In one embodiment, the plug may not be removed, but may be made of a self-sealing material, such as a silicone material, allowing a needle or other similar instrument to be inserted and removed for cleaning purposes while maintaining a seal. In another embodiment, the plug may be periodically removed for cleaning of the pressure indicator 400. As best seen in FIGS. 56C-E, the plug 406 includes a cutout 409 that may be aligned with a passage 410 in the conduit 404. When the plug 406 is inserted into the conduit 404 such that the cutout 409 is partially or completely aligned with the passage 410, a pressure stabilizing orifice 407 is formed in the conduit 404. As explained below, the pressure stabilizing orifice 407 is configured to dampen oscillations in the pressures transmitted from the OPEP device 300 to the manometer 408.

Figure 56F:
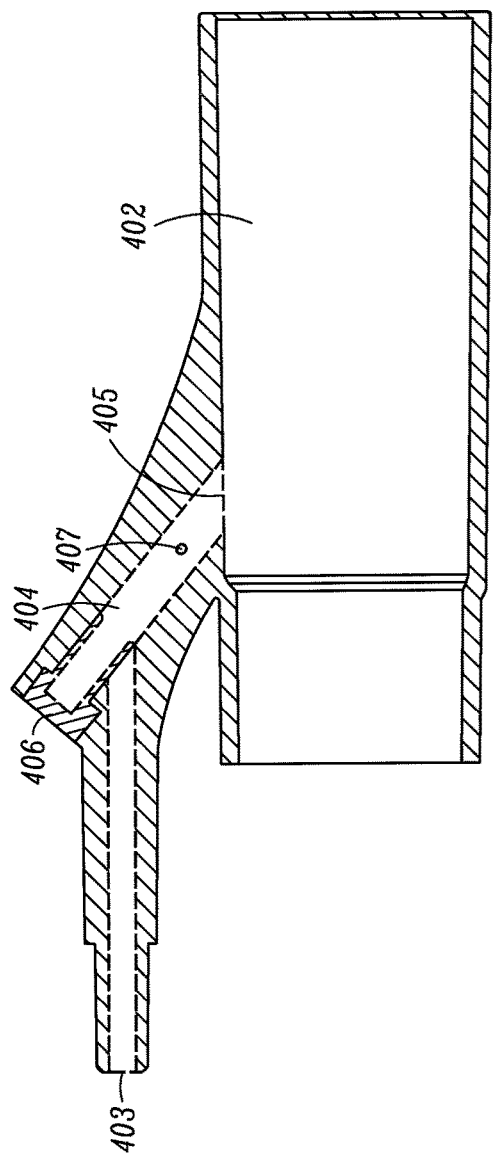

As shown in FIGS. 56C-E, the size and shape of the pressure stabilizing orifice 407 may be selectively adjustable by rotating the plug 406 relative to the passage 410, thereby increasing or decrease the amount of dampening. While the pressure stabilizing orifice 407 is shown as being adjustable, it should be appreciated that the size and shape of the pressure stabilizing orifice 407 may be fixed. Furthermore, it should be appreciated that the pressure stabilizing orifice 407 may be positioned anywhere along the conduit 404 between the body 402 and the manometer 408, for example, as seen in FIG. 56F, or in a portion of the conduit 404 extending into the manometer 408, or in a passageway forming part of the instrument for measuring pressure, for example, as seen in FIG. 56G. However, in order for the pressure stabilizing orifice 407 to effectively dampen oscillations in the pressures transmitted from the OPEP device 300 to the manometer 408, the cross-sectional area of the pressure stabilizer orifice 407 should be less than a cross-sectional area of the conduit 404 along the entire length of the conduit 404. In this embodiment, the pressure stabilizer orifice 407 has a diameter of 0.5 mm to 1.5 mm, or a cross-sectional area between 0.196 mm² and 1.767 mm². Preferably, the pressure stabilizer orifice 507 has a diameter of 0.6 mm to 0.9 mm, or a cross-sectional area between 0.283 mm² and 0.636 mm².

As explained in greater detail above with reference to the various OPEP embodiments, during administration of OPEP therapy, an oscillating back pressure is transmitted to the user of the OPEP device, which is received by the user at the mouthpiece. When the pressure indicator 400 is connected to such an OPEP device, for example the OPEP device 300, the oscillating pressure is transmitted from within the body 402 to the manometer 408 through the conduit 404. The oscillations in the pressure are dampened, however, by the pressure stabilizing orifice 407, as the flow of air along the conduit 404 through the pressure stabilizing orifice 407 is restricted. After the pressure has been dampened by the pressure stabilizing orifice 407, it is received and measured by the manometer 408, which in turn provides the user with a visual indication of the pressure achieved during administration of OPEP therapy. This allows the user or caregiver to monitor the treatment regimen or therapy to ensure that the appropriate pressures are achieved for the prescribed period of time. In some instances, a treatment regimen or therapy alternating between exhalation at a high pressure for a predetermined period of time and exhalation at a low pressure for a predetermined period of time may be desirable. A visual or auditory indication of the pressure achieved during treatment will allow the user or caregiver to determine the level of compliance with the prescribed treatment regimen or therapy.

Figure 56H:
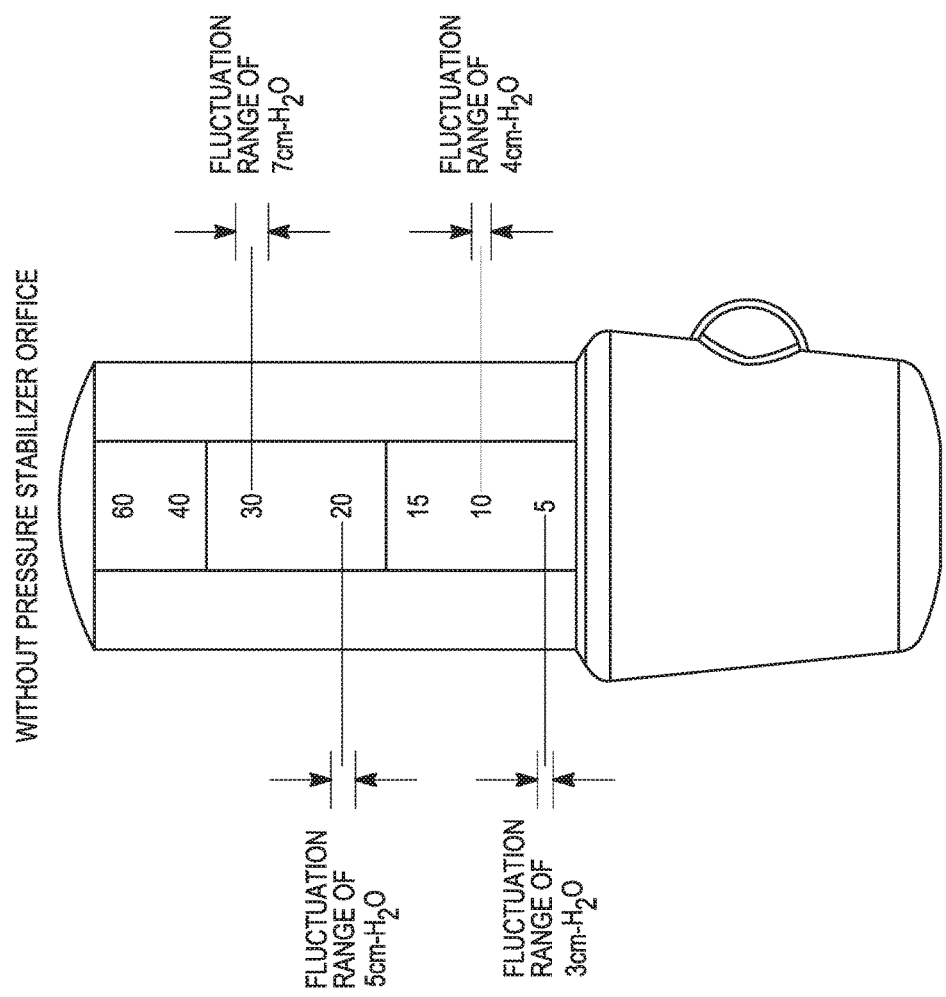
FIGS. 56H-56I provide an illustration comparing the oscillations in pressures observed using the pressure indicator of FIG. 53 without a pressure stabilizing orifice to the pressure indicator of FIG. 53 with a pressure stabilizing orifice.
Figure 56I:
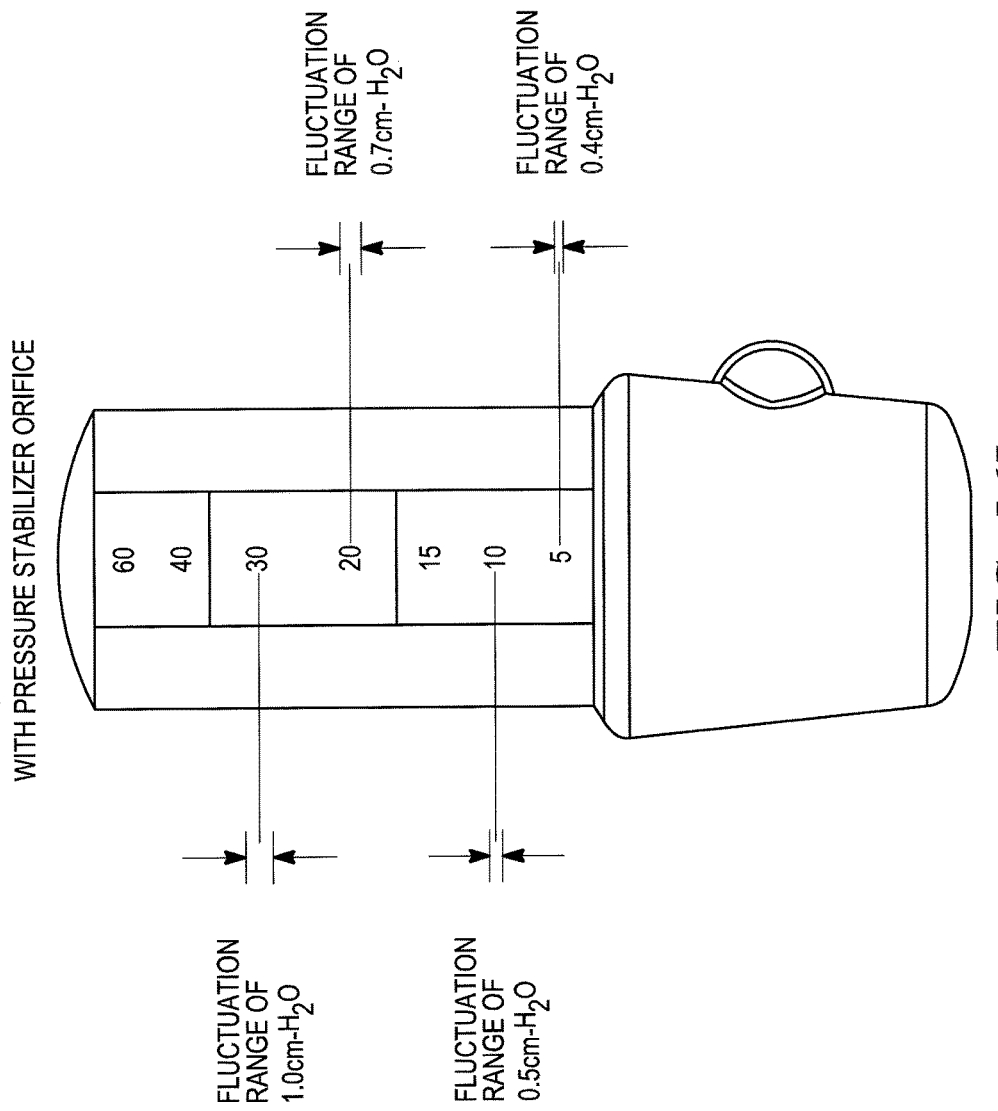

Turning to FIGS. 56H-56I, an illustration is provided comparing the oscillations in pressures observed using a pressure indicator according to the present embodiment without a pressure stabilizing orifice (FIG. 56H) to a pressure indicator according to the present embodiment with a pressure stabilizing orifice (FIG. 56I) when used in conjunction with an AEROBIKA® OPEP device from Trudell Medical International of London, Canada. The observed pressures are also set forth in the following table:

| OPEP Device Pressure (cm-$H_2O$) | Pressure Oscillations Without Stabilizing Orifice (cm-$H_2O$) | Pressure Oscillations With Stabilizing Orifice (cm-$H_2O$) |
|---|---|---|
| 30 | 7 | 1 |
| 20 | 5 | 0.7 |
| 10 | 4 | 0.5 |
| 5 | 3 | 0.4 |

It is further observed that use of the pressure indicator 400 does not adversely affect the performance of the OPEP device to which it is attached, or to the delivery of aerosolized medication from a nebulizer attached to such an OPEP device.

Second Embodiment of a Pressure Indicator

Figure 57:
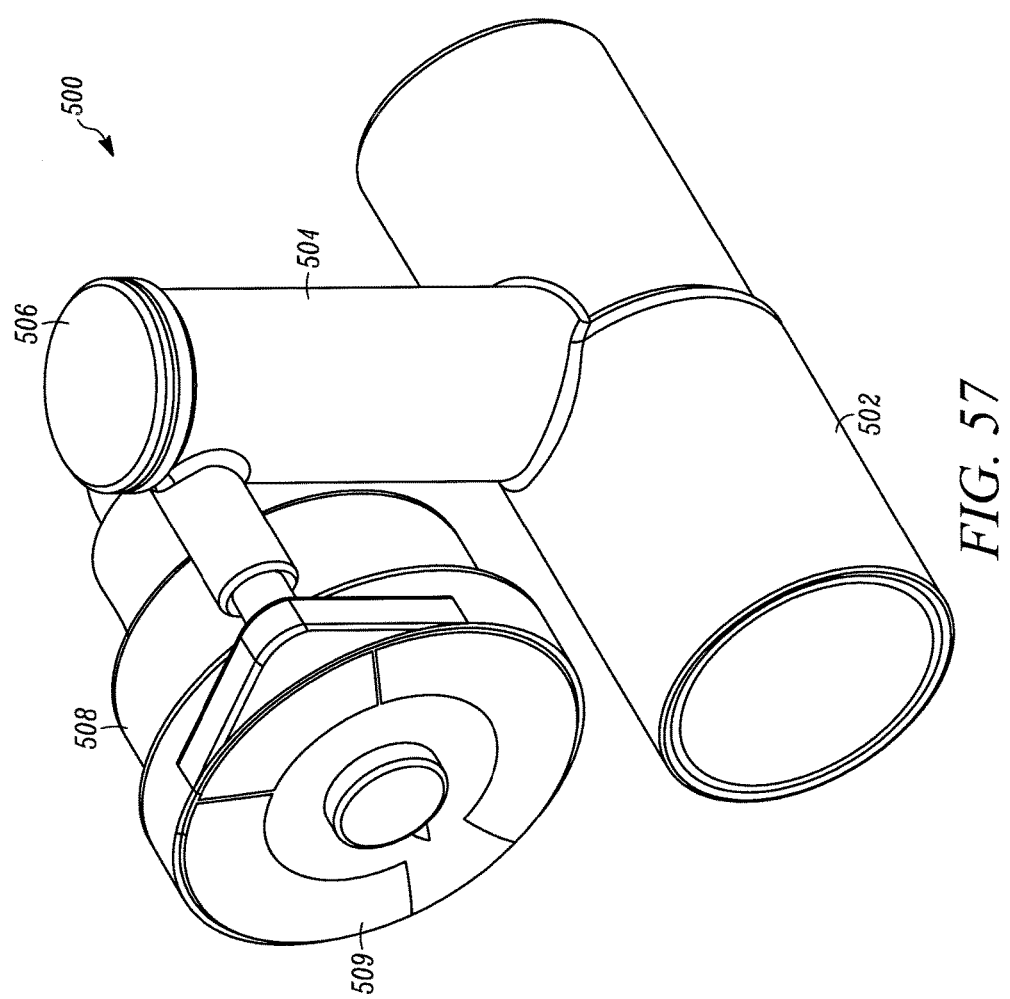
FIG. 57 is a perspective view of a second embodiment of a pressure indicator for an OPEP device.
Figure 58:
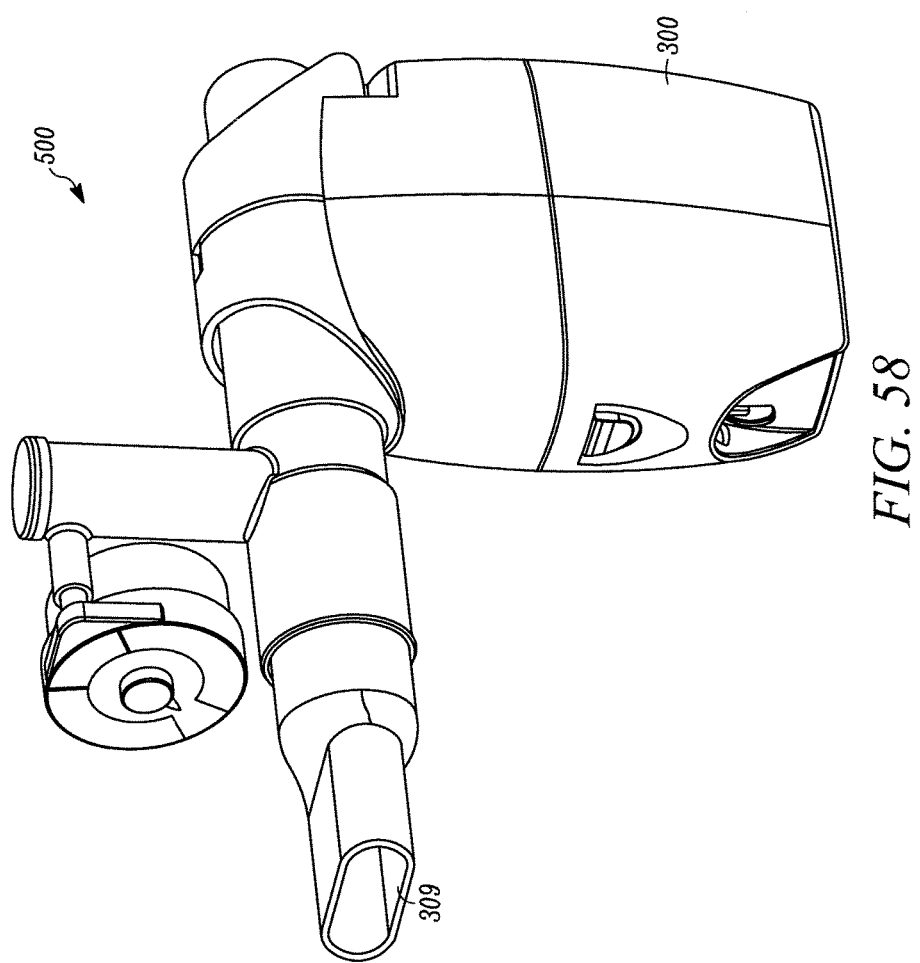
FIG. 58 is a perspective view of the pressure indicator of FIG. 57 connected to the OPEP device of FIG. 35.
Figure 59A:
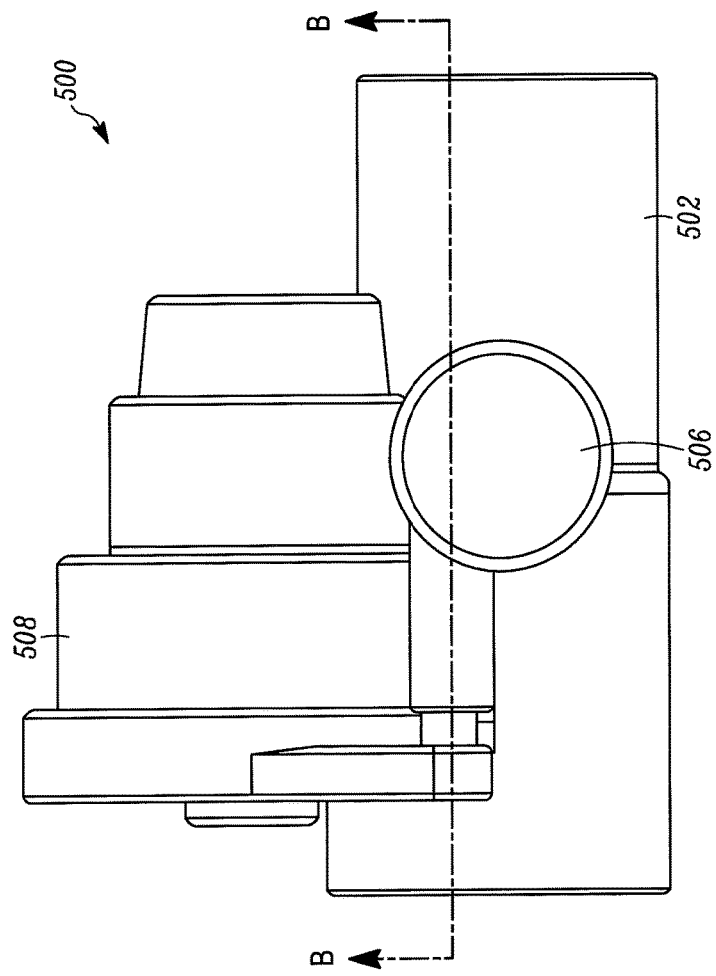

Turning to FIGS. 57-59, a second embodiment of a pressure indicator 500 is shown. In general, the pressure indicator 500 includes a body 502, a conduit 504 extending from the body 502, a cap 506 positioned along the conduit 504, and an instrument for measuring pressure in the form of a manometer 508 positioned at an outlet of the conduit 504.

The body 502 may be sized and shaped for integration with existing OPEP devices, for example, as shown in FIG. 58, with the mouthpiece 309 of the OPEP device 300. In this example, the body 502 is again comprised of 22 mm ISO male/female conical connectors shaped and sized to connect to the mouthpiece 309 of the OPEP device 300.

Extending from the body 502 is a conduit 504 configured to transmit a pressure from within the OPEP device 300 to the manometer 508. An inlet 505 permits a pressure within the body 502 to pass into the conduit 504. As shown, the conduit 504 extends away from the body 502 only a short distance to allow for connection to the manometer 508, thereby maintaining the portability and ergonomics of the OPEP device 300, and avoiding the need for lengthy tubing or additional attachments.

The manometer 508 is positioned at an outlet 503 of the conduit 504. It should be appreciated, however, that a portion of the conduit 504 could extend into the instrument for measuring pressure, such as the manometer 508. The manometer 508 may be a dial-type gauge such as, for example, a MERCURY MEDICAL® Disposable Pressure Manometer from Mercury Medical of Clearwater, Fla. Other instruments suitable for measuring pressure from a respiratory treatment device, such as an OPEP device, may also be used in place of the manometer 508. In general, the manometer 508 includes an indicator that in one embodiment is rotated in response to a change in pressure. Preferably, the manometer 408 includes an indicia 409 of pressures measured by the manometer, e.g., numbers, color coding, etc. As shown, the manometer 508 is positioned relative to the OPEP device 300 such that the indicator and indicia 509 are viewable to a user of the OPEP device 300 during treatment.

A pressure stabilizing orifice 507 is positioned along the conduit 504. However, the pressure stabilizing orifice 507 could also be positioned in a portion of the conduit 504 extending into the manometer 508, or the conduit or other passageway forming part of the instrument for measuring pressure. In this embodiment, the pressure stabilizer orifice 507 has a fixed shape and size, and a diameter of 0.5 mm to 1.5 mm, or a cross-sectional area between 0.196 $mm^2$ and 1.767 $mm^2$. Preferably, the pressure stabilizer orifice 507 has a diameter of 0.6 mm to 0.9 mm, or a cross-sectional area between 0.283 $mm^2$ and 0.636 $mm^2$.

The cap 506 is insertable into the conduit 504 by pressfitting. The cap 506 may be periodically removed for cleaning of the pressure indicator 500. Unlike the plug 406 in the pressure indicator 400, the cap 506 does not align with a passage, and does not form part of the pressure stabilizing orifice 507.

The pressure indicator 500 otherwise operates in the same manner as the pressure indicator 400 described above.

Figure 59D:
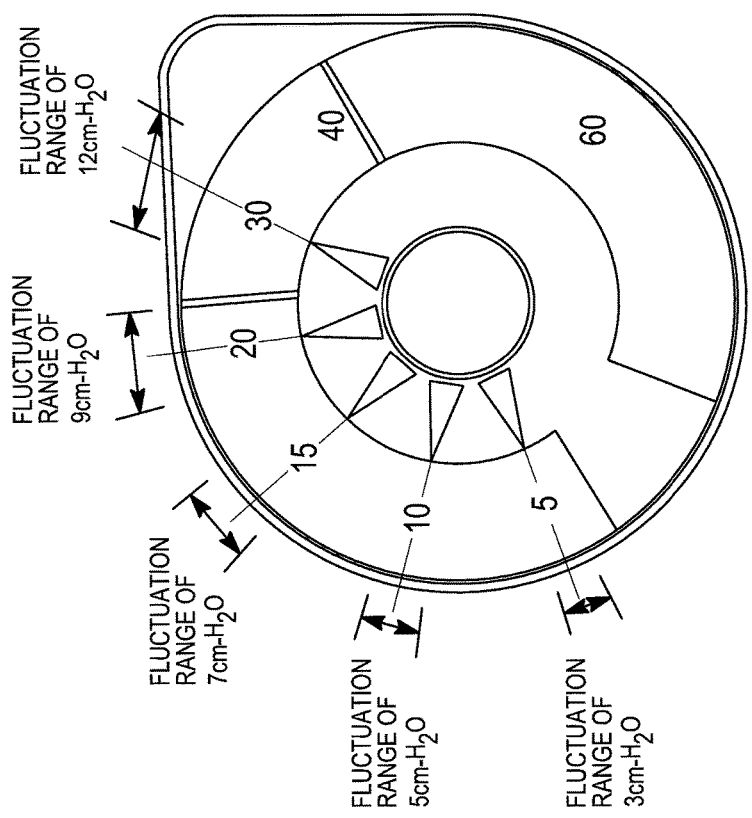
FIGS. 59D-59E provide an illustration comparing the oscillations in pressures observed using the pressure indicator of FIG. 57 without a pressure stabilizing orifice to the pressure indicator of FIG. 57 with a pressure stabilizing orifice.
Figure 59E:
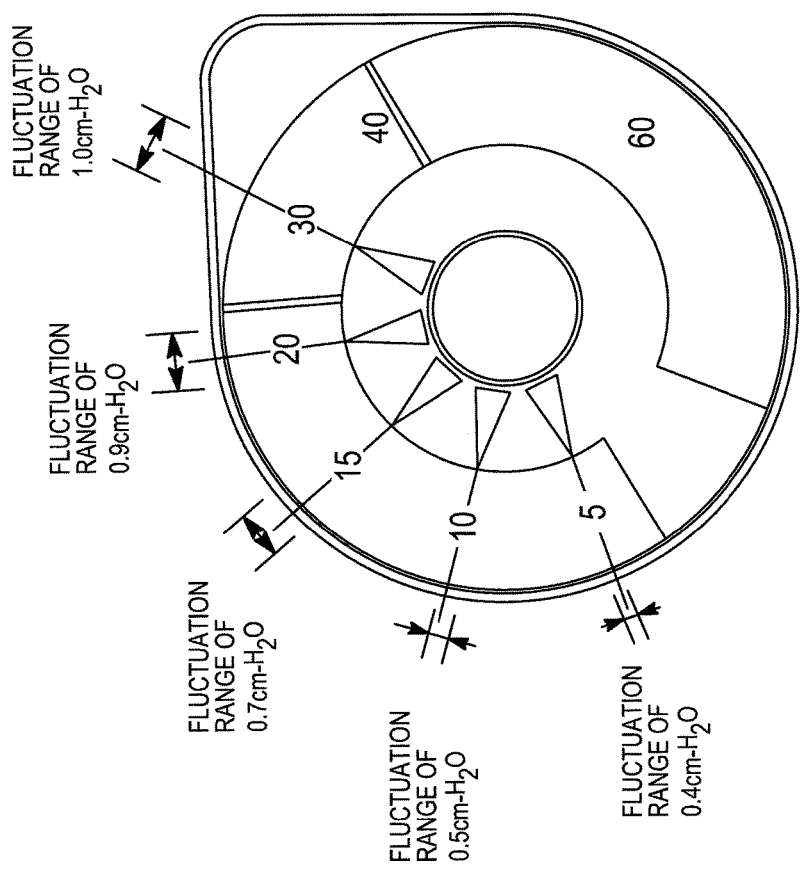

Turning to FIGS. 59D-59E, an illustration is provided comparing the oscillations in pressures observed using a pressure indicator according to the present embodiment without a pressure stabilizing orifice (FIG. 59D) to a pressure indicator according to the present embodiment with a pressure stabilizing orifice (FIG. 59E) when used in conjunction with an AEROBIKA® OPEP device from Trudell Medical International of London, Canada. The observed pressures are also set forth in the following table:

| OPEP Device Pressure (cm-$H_2O$) | Pressure Oscillations Without Stabilizing Orifice (cm-$H_2O$) | Pressure Oscillations With Stabilizing Orifice (cm-$H_2O$) |
|---|---|---|
| 30 | 12 | 1 |
| 20 | 9 | 0.9 |
| 15 | 7 | 0.7 |
| 10 | 5 | 0.5 |
| 5 | 3 | 0.4 |

It is further observed that use of the pressure indicator 500 does not adversely affect the performance of the OPEP device to which it is attached, or to the delivery of aerosolized medication from a nebulizer attached to such an OPEP device.

Third Embodiment of a Pressure Indicator

Turning to FIGS. 60-61, a third embodiment of a pressure indicator 600 is shown connected to the OPEP device 300. The pressure indicator 600 differs from the pressure indicator 500 in that the pressure indicator 600 is sized and shaped for integration with existing OPEP devices, for example, as shown in FIG. 60, with the inhalation port 311 of the OPEP device 300 (see also, FIGS. 35-35 and 40).

As with the pressure indicator 500, the pressure indicator 600 includes a body 602, a conduit 604 extending from the body 602, an inlet 605 and an outlet 603 to the conduit 604, a cap 606 positioned along the conduit 604, a dial-type manometer 608 positioned at an end of the conduit 604, and a pressure stabilizer orifice 607. As shown, the manometer 608 is positioned relative to the OPEP device 300 such that the indicator and indicia are viewable to a caregiver and/or a user of the OPEP device 300 during treatment.

The pressure indicator 600 further includes a one-way valve 684 positioned within the body 602, and a prong 612 that extends from within the body 602 into the inhalation port 311 of the OPEP device 300. The one-way valve 684 is configured to open upon inhalation at the mouthpiece 309 of the OPEP device 300, and close upon exhalation. The prong 612 is configured to hold the one-way valve 384 in an open positioned, thereby placing the body 602 in fluid communication with the mouthpiece 309.

In operation, the pressure indicator 600 is configured to operate in the same manner as the pressure indicator 500 described above, and provide the same visual feedback as the pressure indicator 500 connected to the mouthpiece 309 of the OPEP device 300.

Fourth Embodiment of a Pressure Indicator

Figure 62:
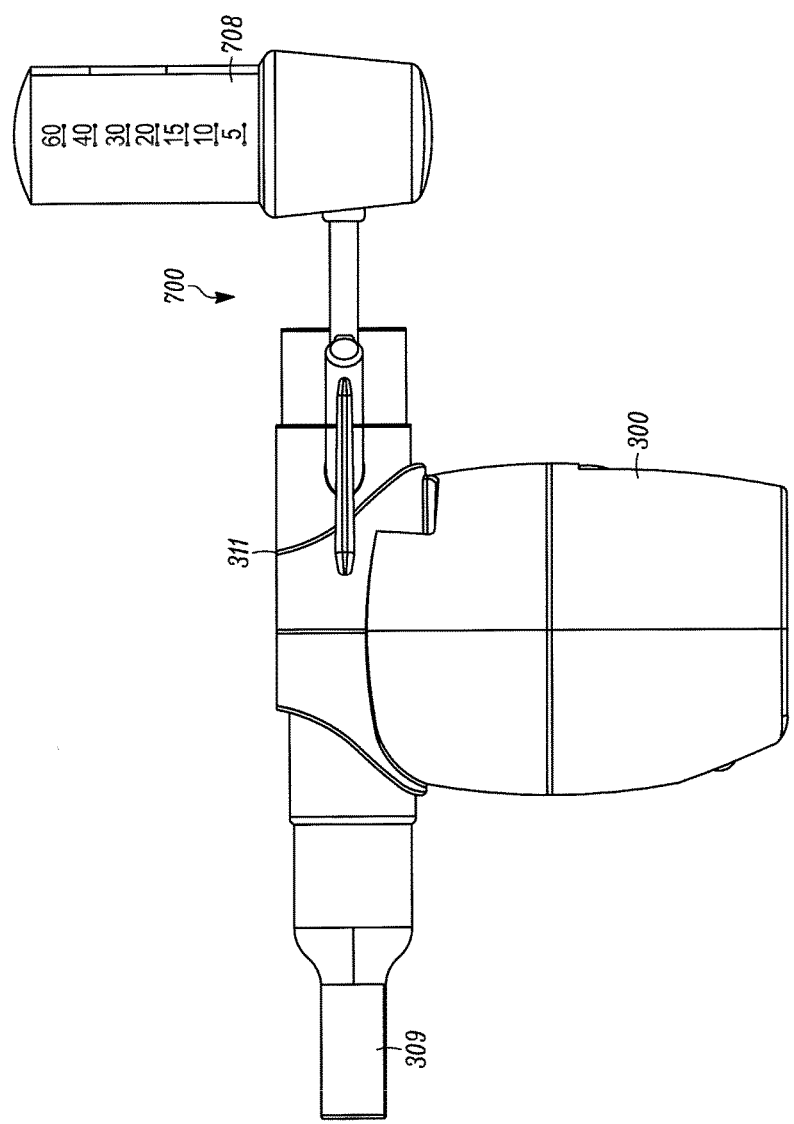
FIG. 62 is a side view of a fourth embodiment of a pressure indicator connected to the OPEP device of FIG. 35.

Turning to FIGS. 62-63, a fourth embodiment of a pressure indicator 700 is shown connected to the OPEP device 300. The pressure indicator 700 differs from the pressure indicator 400 in that the pressure indicator 700 is sized and shaped for integration with existing OPEP devices, for example, as shown in FIG. 62, with the inhalation port 311 of the OPEP device 300 (see also, FIGS. 35-35 and 40).

As with the pressure indicator 400, the pressure indicator 700 includes a body 702, a conduit 704 extending from the body 702, an inlet 705 and an outlet 703 to the conduit 704, a plug 706 positioned along the conduit 704, a piston-type manometer 708 positioned at an end of the conduit 704, and a pressure stabilizer orifice 707. As shown, the manometer 708 is positioned relative to the OPEP device 300 such that the indicator and indicia are viewable to a user of the OPEP device 300 during treatment.

Like the pressure indicator 600, the pressure indicator 700 further includes a one-way valve 784 positioned within the body 702, and a prong 712 that extends from within the body 702 into the inhalation port 711 of the OPEP device 300. The one-way valve 784 is configured to open upon inhalation at the mouthpiece 309 of the OPEP device 300, and close upon exhalation. The prong 712 is configured to hold the one-way valve 384 in an open positioned, thereby placing the body 702 in fluid communication with the mouthpiece 709.

In operation, the pressure indicator 700 is configured to operate in the same manner as the pressure indicator 400 described above, and provide the same visual feedback as the pressure indicator 400 connected to the mouthpiece 309 of the OPEP device 300.

Fifth Embodiment

As noted above with respect to pressure indicator 400, the pressure stabilizing orifice may be positioned anywhere along the conduit between the body and the manometer, for example, as seen in FIG. 56F, or in a portion of the conduit extending into the manometer, or in a passageway forming part of the instrument for measuring pressure, for example, as seen in FIG. 56G. It should further be appreciated that one or more pressure stabilizing orifices may be positioned within the manometer, for example, at an inlet to the manometer, at a vent for the manometer, or at both the inlet and the vent, to dampen the oscillations in the pressure measured by the manometer.

Figure 64A:
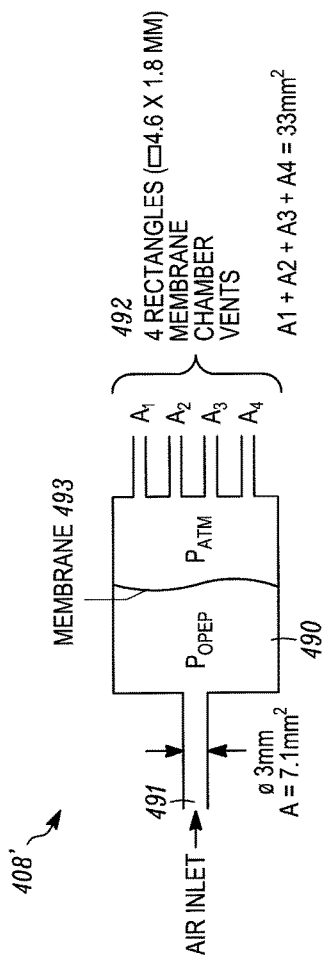
FIGS. 64A-B are illustrations of a manometer configured with a pressure stabilizing orifice.

Turning to FIG. 64A, an illustration is provided showing a manometer 408', for example an AMBU® Disposable Pressure Manometer from Ambu A/S of Copenhagen, Denmark. In general, the manometer 408' includes a chamber 490, an air inlet 491, one or more openings forming a vent 492, and a membrane 493 disposed therebetween. The membrane 493 divides the chamber 490 in two, creating a side exposed to the pressures obtained in the OPEP device, and a side exposed to atmospheric pressure. As air flows from the OPEP device into the chamber through the inlet 491, the pressure increases in the chamber 490 on the OPEP side, causing the membrane 493 to expand and expel the air on the side of the chamber 490 exposed to atmospheric pressure through the vent 492. As shown in FIG. 64A, the inlet 491 has a diameter of 3 mm and a cross-sectional area of 7.1 mm$^2$, while the vent 492 is comprised of four rectangular openings (4.6 mm by 1.8 mm) having a combined cross-sectional area of 33 mm$^2$.

Figure 64B:
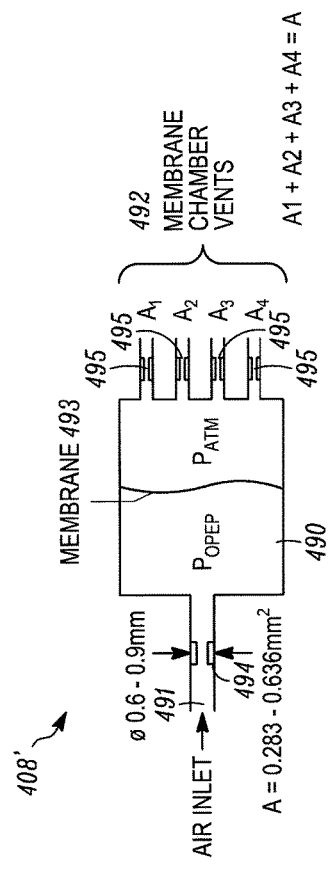

As shown in FIG. 64B, one or more pressure stabilizing orifices may be positioned within the manometer 408', at the inlet 491 to the manometer 408', at the vent 492 for the manometer 408', or at both the inlet 491 and the vent 492. For example, a pressure stabilizing orifice 494 positioned at the inlet 491 may have a diameter of 0.6 mm to 0.9 mm, or a cross-sectional area of 0.283 mm$^2$ to 0.636 mm$^2$. A pressure stabilizing orifice 495 may also be positioned at the vent 492, which as shown in FIG. 64B includes four rectangular openings. Like the cross-sectional area of the pressure stabilizing orifice 494 positioned at the inlet 491, the combined cross-sectional area of the openings forming the pressure stabilizing orifice 495 positioned at the vent 492 ranges from 0.283 mm$^2$ to 0.636 mm$^2$. As noted above, a pressure stabilizing orifice could be positioned at the inlet 491, at the vent 492, or at both the inlet 491 and the vent 492. By restricting the flow of air into the manometer 408' through the inlet, or out of the manometer 408' through the vent 492, the pressure stabilizing orifice dampens oscillations in the pressures measured by the manometer 408', thereby allowing the pressure indicator to display a readable pressure level, and at the same time, provide dynamic visual feedback to let the user know that the OPEP device is working.

Figure 65A:
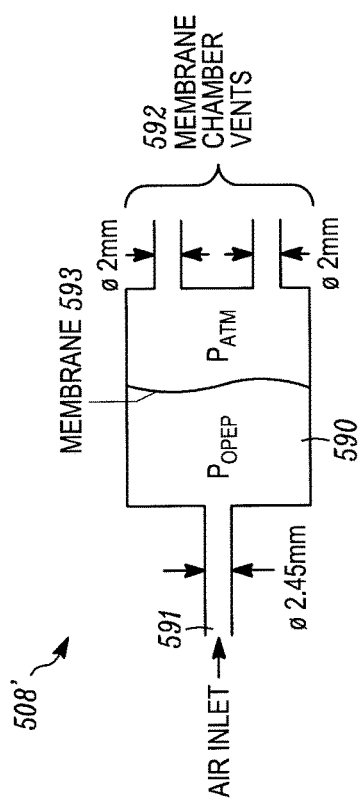
FIGS. 65A-B are illustrations of another manometer configured with a pressure stabilizing orifice.

Similarly, turning to FIG. 65A, an illustration is provided showing a manometer 508', for example a MERCURY MEDICAL® Disposable Pressure Manometer from Mercury Medical of Clearwater, Fla. In general, the manometer 508' includes a chamber 590, an air inlet 591, one or more openings forming a vent 592, and a membrane 593 disposed therebetween. The membrane 593 divides the chamber 590 in two, creating a side exposed to the pressures obtained in the OPEP device, and a side exposed to atmospheric pressure. As air flows from the OPEP device into the chamber through the inlet 591, the pressure increases in the chamber 590 on the OPEP side, causing the membrane 593 to expand and expel the air on the side of the chamber 590 exposed to atmospheric pressure through the vent 592. As shown in FIG. 65A, the inlet 591 has a diameter of 2.45 mm, while the vent 492 is comprised of two openings each having a diameter of 2 mm.

Figure 65B:
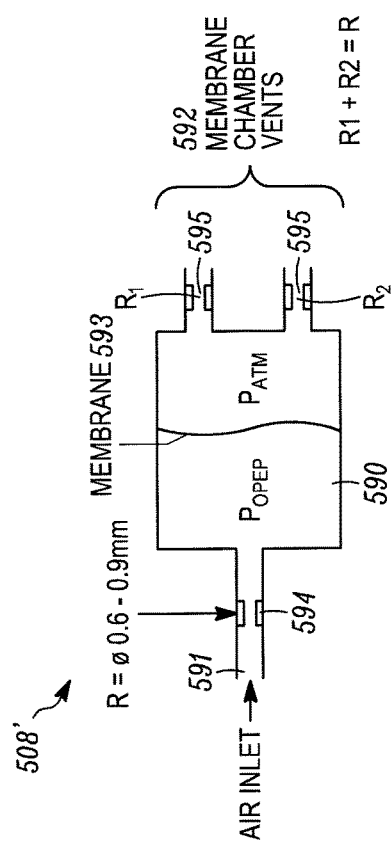

As shown in FIG. 65B, one or more pressure stabilizing orifices may be positioned within the manometer 508', at the inlet 591 to the manometer 508', at the vent 592 for the manometer 508', or at both the inlet 591 and the vent 592. For example, a pressure stabilizing orifice 594 positioned at the inlet 591 may have a diameter of 0.6 mm to 0.9 mm, or a cross-sectional area of 0.283 mm$^2$ to 0.636 mm$^2$. A pressure stabilizing orifice 595 may also be positioned at the vent 592, which as shown in FIG. 65B includes two openings. Like the cross-sectional area of the pressure stabilizing orifice 594 positioned at the inlet 591, the combined cross-sectional area of the openings forming the pressure stabilizing orifice 595 positioned at the vent 592 ranges from 0.283 mm$^2$ to 0.636 mm$^2$. As noted above, a pressure stabilizing orifice could be positioned at the inlet 591, at the vent 592, or at both the inlet 591 and the vent 592. By restricting the flow of air into the manometer 508' through the inlet, or out of the manometer 58' through the vent 4592, the pressure stabilizing orifice dampens oscillations in the pressures measured by the manometer 508', thereby allowing the pressure indicator to display a readable pressure level, and at the same time, provide dynamic visual feedback to the let user know that the OPEP device is working.

Additional Implementations

Figure 66:
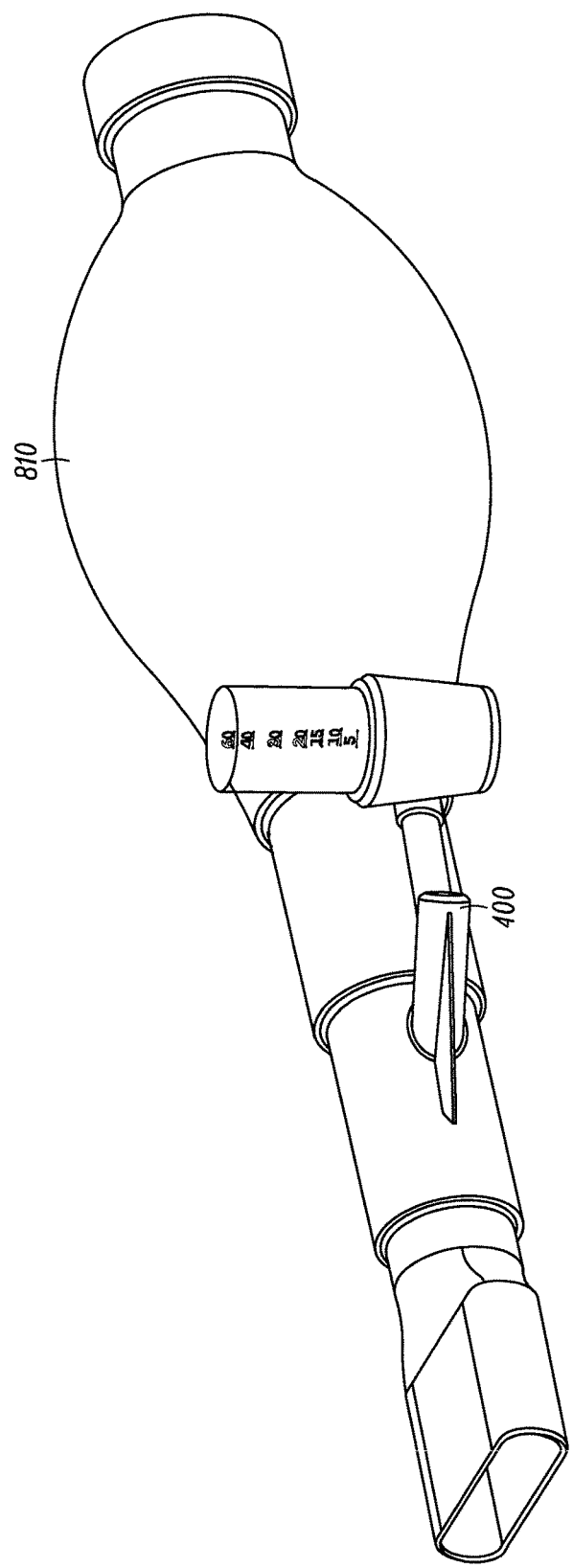
FIGS. 66-67 are perspective views of the pressure indicators of FIGS. 53 and 57 connected to a commercially available OPEP device.
Figure 67:
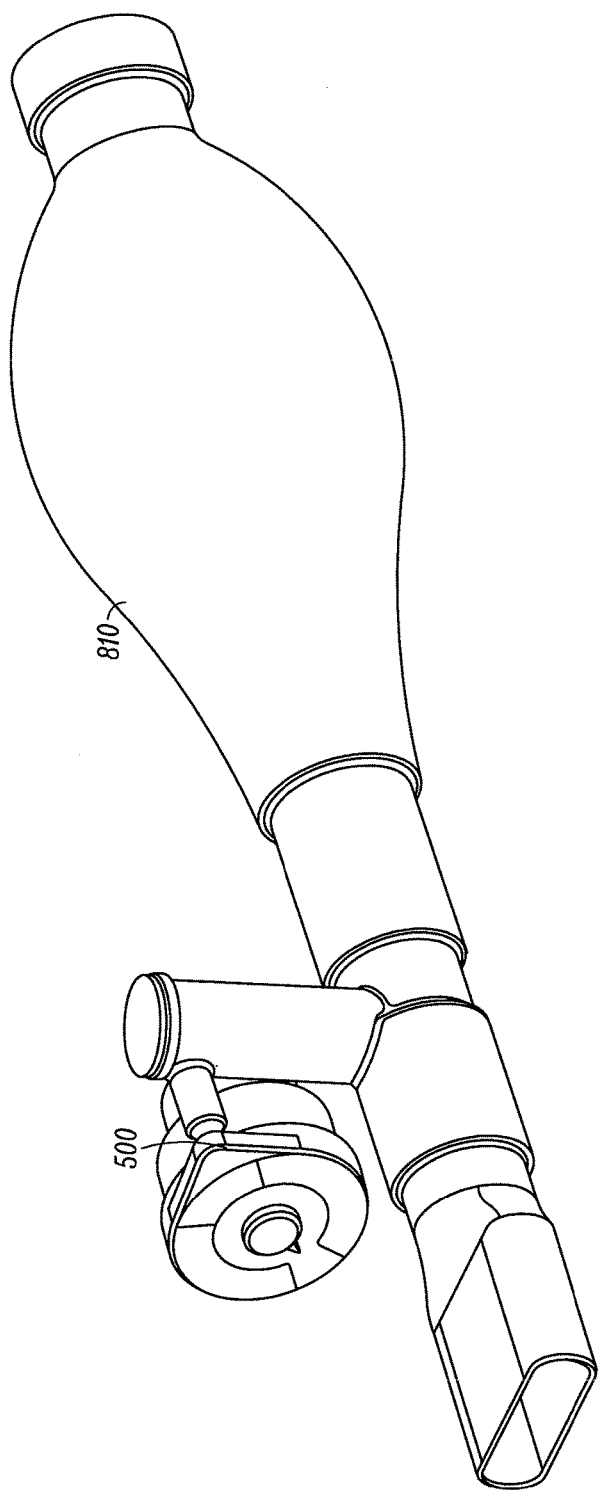
Figure 68:
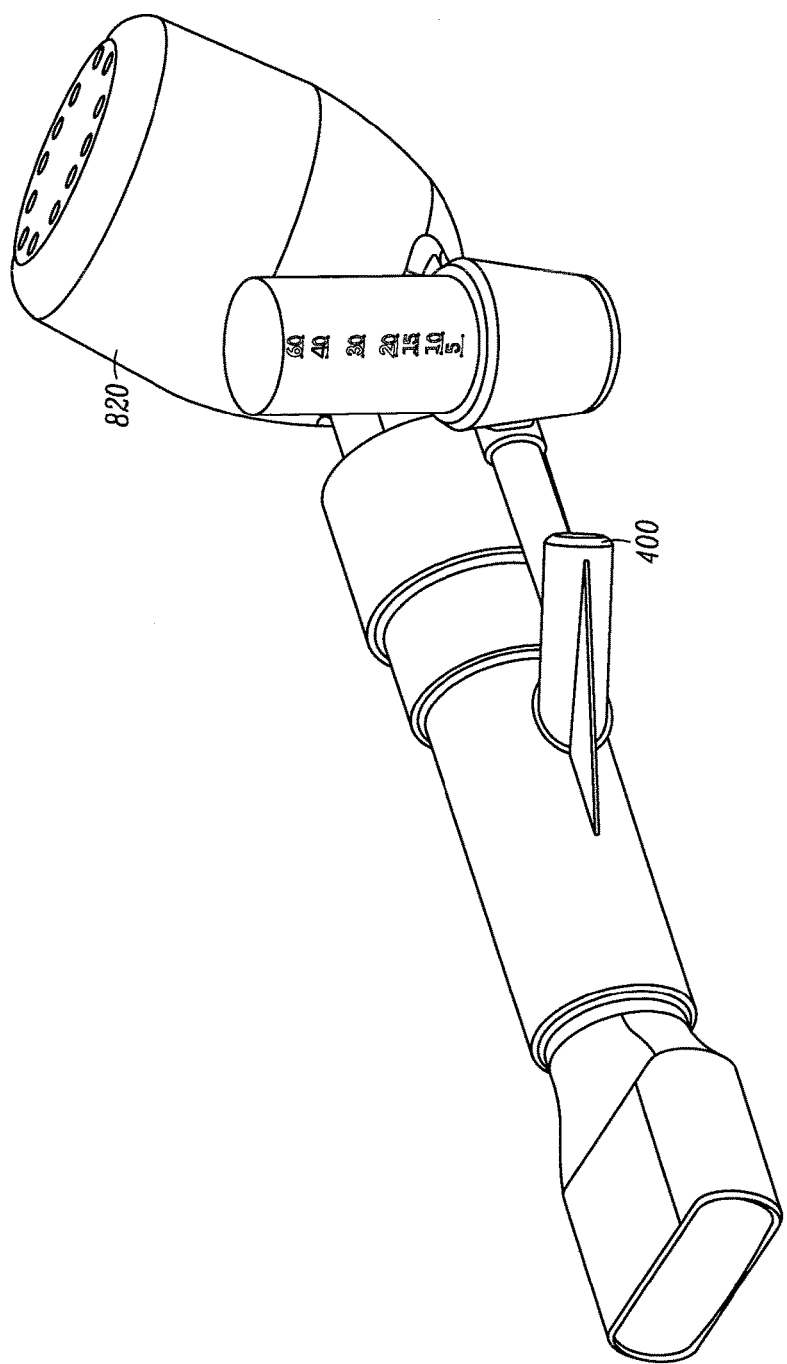
FIGS. 68-69 are perspective views of the pressure indicators of FIGS. 53 and 57 connected to another commercially available OPEP device.
Figure 69:
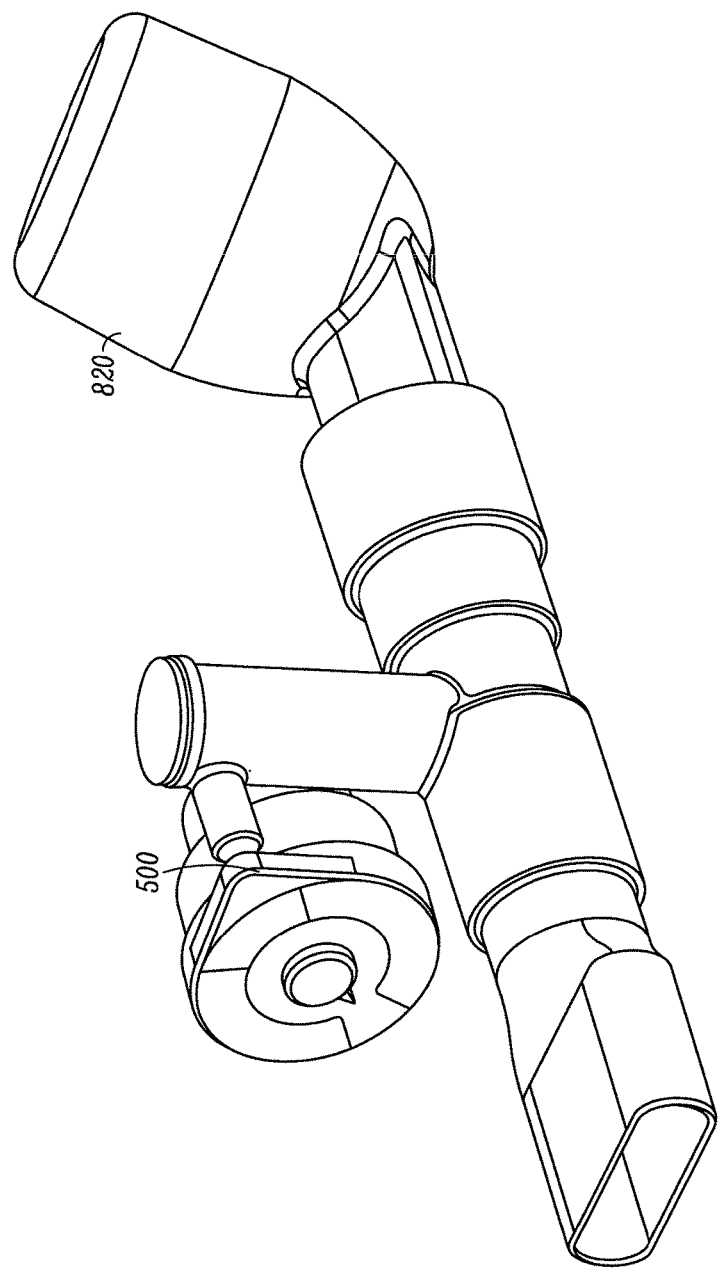
Figure 70:
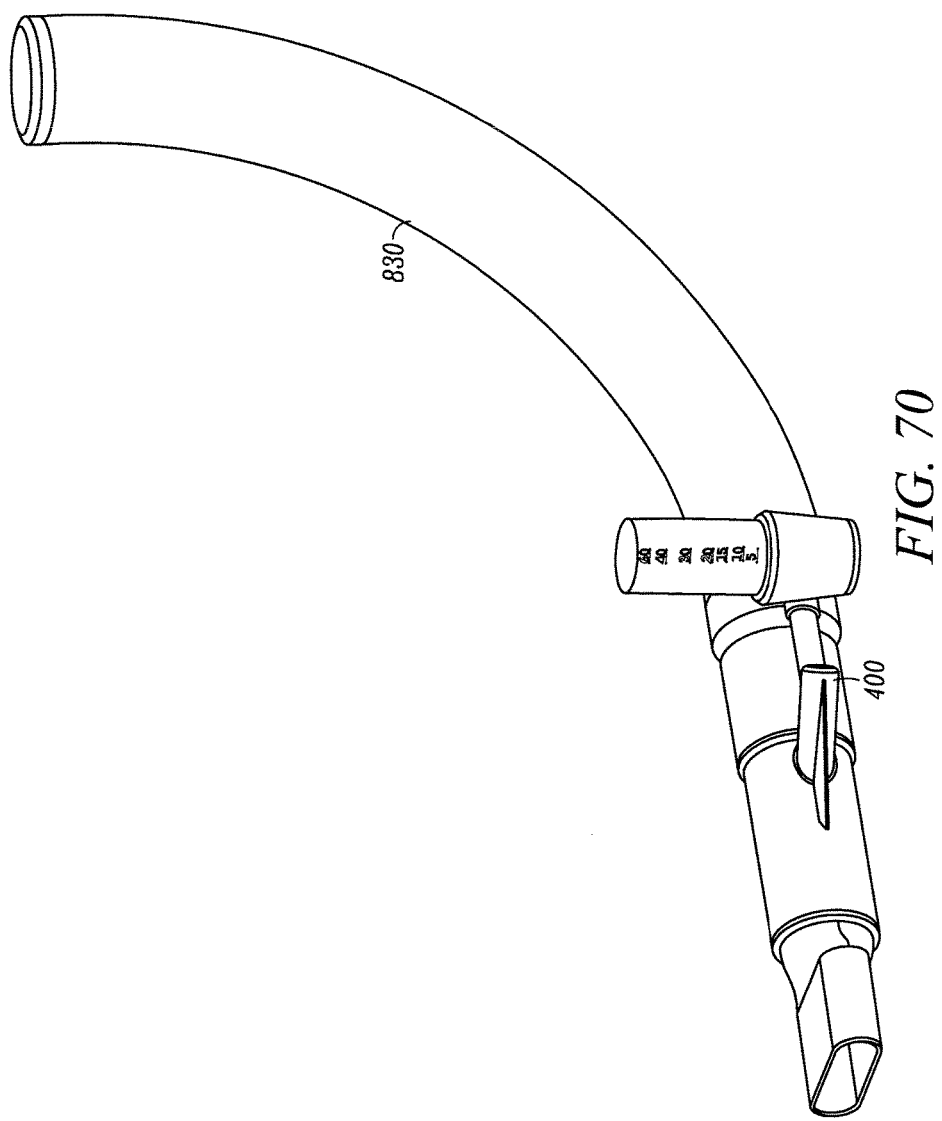
FIGS. 70-71 are perspective views of the pressure indicators of FIGS. 53 and 57 connected to another commercially available OPEP device.
Figure 71:
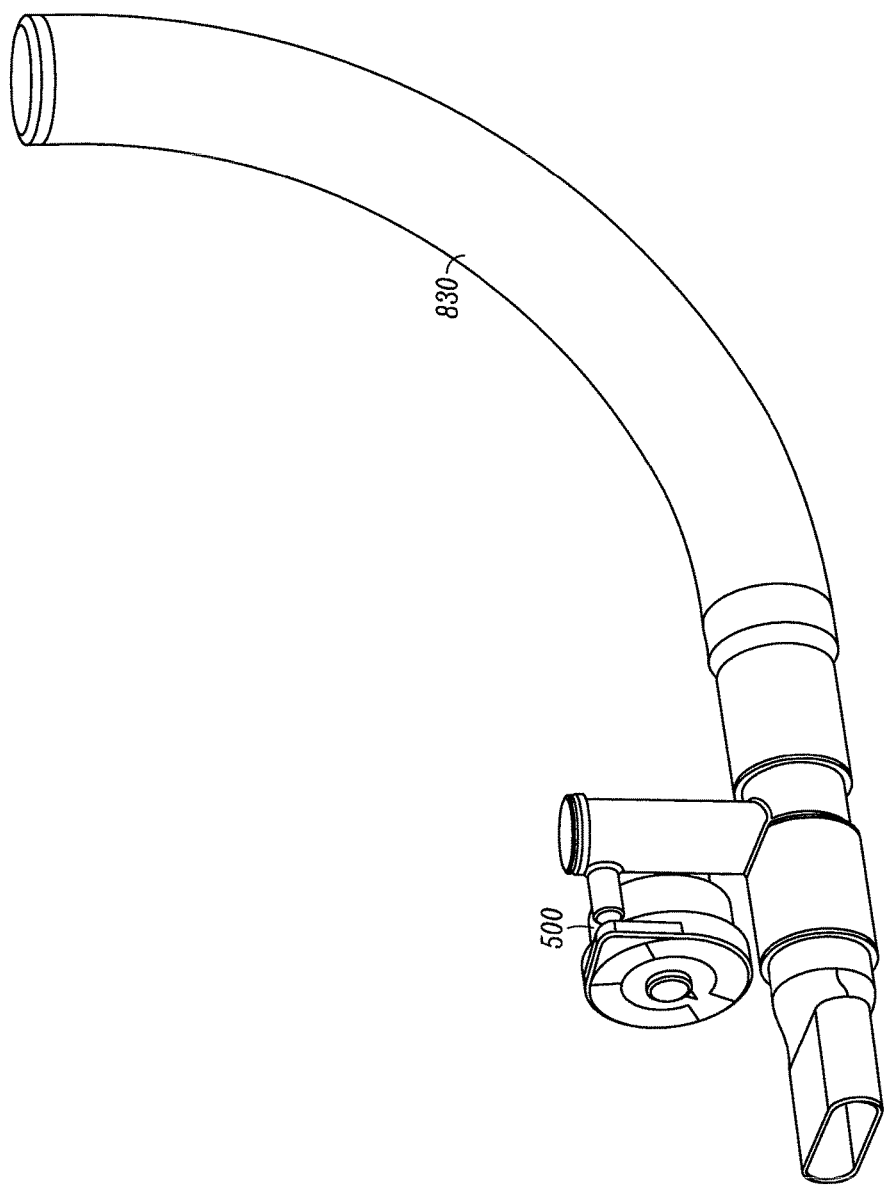

As previously noted, the pressure indicator embodiments described herein may be used with other OPEP devices, including for example: an ACAPELLA® OPEP device 810 from Smiths Medical of St. Paul, Minn., as shown in FIGS. 66-67; a FLUTTER® OPEP device 820 from Axcan Scandipharm Inc. of Birmingham, Ala., as shown in FIGS. 68-69; and, an RC-CORONET® OPEP device 830 from Curaplex of Dublin, Ohio, as shown in FIG. 70-71.

Installation and Use Restriction Features

Figure 72:
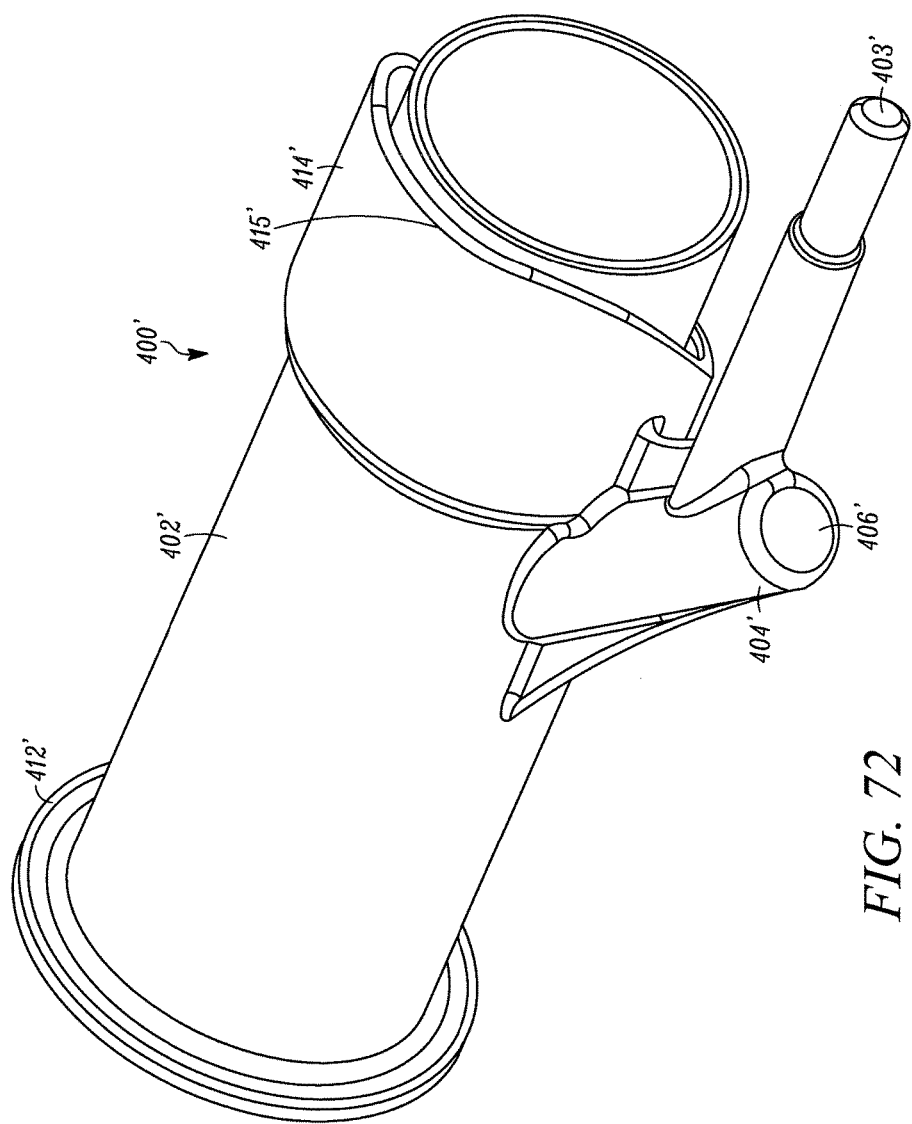
FIG. 72 is a perspective view of an alternative embodiment of a pressure indicator, shown without a manometer, which includes features that prevent unintended installations and restrict use to an approved respiratory treatment device.
Figure 73:
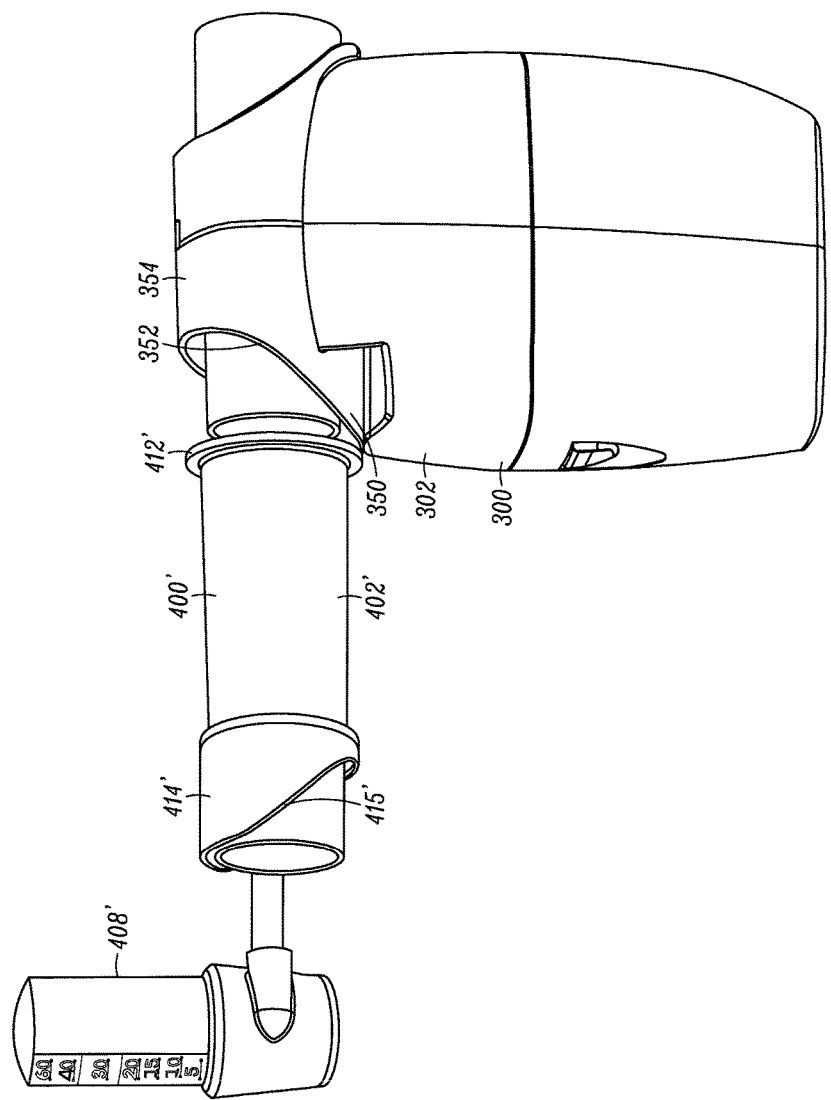
FIG. 73 is a different perspective view of the pressure indicator of FIG. 72, shown with a manometer, during an unintended installation on the OPEP device of FIG. 35; and, FIG. 74 is a side view of the pressure indicator of FIG. 72, shown with a manometer, after installation on an approved respiratory treatment device, in this case the OPEP device of FIG. 35.
Figure 74:
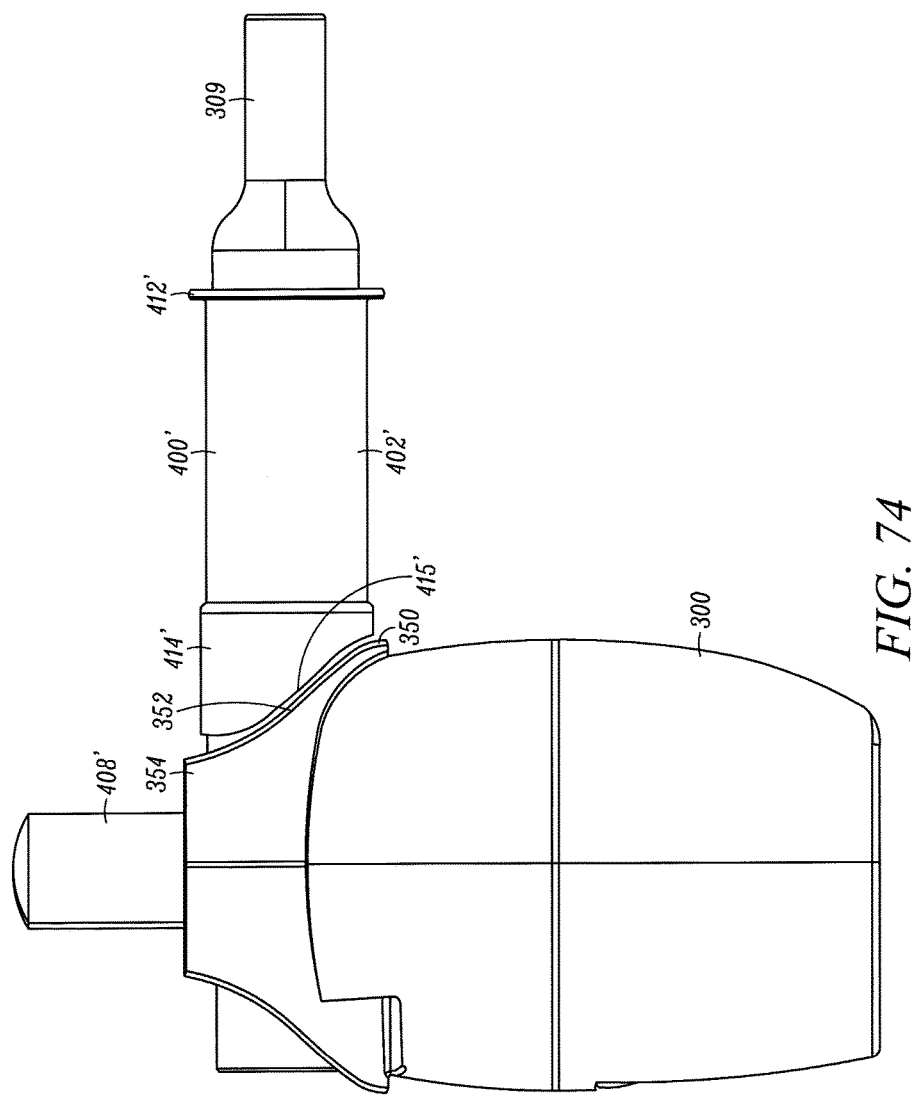

Turning to FIGS. 72-74, another embodiment of a pressure indicator 400' is shown. Except as noted below, the pressure indicator 400' is otherwise the same as the pressure indicator 400 described above, and is configured to operate in the same manner as the pressure indicator 400, and provide the same visual feedback as the pressure indicator 400.

FIG. 72 is a perspective view of the alternative embodiment of a pressure indicator 400', shown without a manometer, which includes features that prevent unintended installations and restrict use to an approved respiratory treatment device. FIG. 73 is a different perspective view of the pressure indicator 400', shown with a manometer 408', during an unintended installation on the OPEP device 300 of FIG. 35. FIG. 74 is a side-view of the pressure indicator 400', after installation on an approved respiratory treatment device, such as the OPEP device 300.

In general, as with the pressure indicator 400, and as seen in FIG. 72, the pressure indicator 400' includes a body 402', a conduit 404' extending from the body 402', and a plug 406' positioned along and inserted into the conduit 404'. Although not shown in FIG. 72, the pressure indicator 400' also includes an instrument for measuring pressure in the form of a manometer 408' positioned at an outlet 403' of the conduit 404', as seen in FIGS. 73-74. The body 402' may be sized and shaped for integration with existing OPEP devices, for example, as shown in FIG. 74, with the mouthpiece 309 of the OPEP device 300. In this embodiment, the body 402' is comprised of 22 mm ISO male/female conical connectors shaped and sized to connect to the mouthpiece 309 of the OPEP device 300, and the OPEP device 300 itself.

As shown in FIGS. 72-73, the pressure indicator 400' includes an annual ring or flange 412' disposed at one end of the housing 402' that prevents unintended installations, such as seen in FIG. 73. Specifically, when a user attempts to install the pressure indicator 400' on an OPEP device 300 in a backwards or reversed orientation, the flange 412' contacts an extension 350 extending from the housing 302 of the OPEP device 300, such that the corresponding 22 mm ISO male/female conical connectors on the pressure indicator 400' and the OPEP device 300 are prevented from connecting. As seen in FIG. 74, the flange 402' does not prevent the 22 mm ISO male/female conical connectors on the pressure indicator 400' and the mouthpiece 309 of the OPEP device 300 from connecting. In this way, a user is prevented from installing the pressure indicator 400' on an OPEP device 300 in a backwards or reversed orientation.

As shown in FIGS. 72 and 74, the pressure indicator 400' also includes a collar 414' disposed at an end of the housing 402' opposite the flange 412' that restricts use of the pressure indicator 400' to an approved respiratory treatment device. As shown in FIG. 74, the approved respiratory treatment device may be the OPEP device 300. Specifically, when a user attempts to install the pressure indicator 400' on the OPEP device 300 in the intended orientation, a specific contour 415' of the collar 414' on the pressure indicator 400' aligns with a corresponding specific contour 352 of a collar 354 on the OPEP device 300, such that the 22 mm ISO male/female conical connectors on the pressure indicator 400' and the OPEP device 300 may fully engage and complete a connection. However, if a user attempts to install the pressure indicator 400' on a respiratory treatment device that does not have a specific contour intended to correspond to and receive the specific contour 415' of the collar 414' on the pressure indicator 400', the collar 414 will likely contact with the respiratory treatment device in a manner that prevents connection of the 22 mm ISO/male/female connector on the pressure indicator 400' with the respiratory treatment device. If should be appreciated that the specific contour 415' of the collar 414' and the corresponding specific contour 352 of the collar 354 on the OPEP device are merely exemplary, and that any number of other contours or keyed patterns may be used. In this way, use of the pressure indicator 400' may be restricted to an approved respiratory treatment device like the OPEP device 300.

Although the foregoing description is provided in the context of OPEP devices, it will also be apparent to those skilled in the art that other respiratory treatment devices may benefit from various teachings contained herein. The foregoing description has been presented for purposes of illustration and description, and is not intended to be exhaustive or to limit the inventions to the precise forms disclosed. It will be apparent to those skilled in the art that the present inventions are susceptible of many variations and modifications coming within the scope of the following claims.

What is claimed is:

1. A pressure indicator for an oscillating positive expiratory pressure ("OPEP") device, the pressure indicator comprising:
   a manometer;
   a conduit configured to transmit a pressure from the OPEP device to the manometer, the pressure having an oscillation frequency exceeding 10 Hz; and,
   a pressure stabilizing orifice positioned within the conduit, the pressure stabilizing orifice being configured to dampen oscillations in the pressure transmitted from the OPEP device to the manometer;
   wherein the pressure stabilizing orifice has a cross-sectional area between 0.196 mm$^2$ and 1.767 mm$^2$.

2. The pressure indicator of claim 1, wherein the pressure stabilizing orifice has a diameter between 0.5 mm and 1.5 mm.

3. The pressure indicator of claim 1, wherein the manometer is configured to measure pressure exceeding 5 cm H$_2$O.

4. The pressure indicator of claim 1, wherein a cross-sectional area of the pressure stabilizing orifice is less than a cross-sectional area of the conduit along an entire length of the conduit.

5. The pressure indicator of claim 1, further comprising a membrane configured to block a flow of air through the manometer to a surrounding atmosphere.

6. The pressure indicator of claim 1, wherein an entire length of the conduit does not exceed a combined length of the pressure indicator and the OPEP device, when the pressure indicator is connected to the OPEP device, as measured from a mouthpiece of the OPEP device to an opposite end of the OPEP device.

7. The pressure indicator of claim 1, wherein when the pressure indicator is connected to a mouthpiece of the OPEP device, a first portion of the conduit is angled outward from mouthpiece, and a second portion of the conduit extends parallel to the mouthpiece.

8. The pressure indicator of claim 7, wherein when the pressure indicator is connected to the mouthpiece of the OPEP device, the manometer is spaced from the OPEP device by a length less than a length of the first portion of the conduit.

9. The pressure indicator of claim 7, wherein when the pressure indicator is connected to the mouthpiece of the OPEP device, an entire length of the conduit does not exceed a combined length of the pressure indicator and the OPEP device, as measured from the mouthpiece to an opposite end of the OPEP device.

10. The pressure indicator of claim 1, wherein a cross-sectional area of the pressure stabilizing orifice is selectively adjustable to increase or decrease an amount of dampening.

11. A system comprising:
the pressure indicator of claim 1; and
an oscillating positive expiratory pressure device.

12. A method of providing visual feedback during administration of oscillating positive expiratory pressure ("OPEP") therapy, the method comprising:
receiving a flow of air from an OPEP device into a pressure indicator connected to the OPEP device, a pressure of the air from the OPEP device oscillating at a frequency exceeding 10 Hz;
dampening oscillations in the pressure of the air from the OPEP device by passing the flow of air through a pressure stabilizing orifice positioned in the pressure indicator, the pressure stabilizing orifice having a cross-sectional area between 0.196 mm$^2$ and 1.767 mm$^2$;
measuring the pressure of the air after the flow of air has passed through the pressure stabilizing orifice; and,
providing an indication of the measured pressure.

13. The method of claim 12, wherein the pressure of the air from the OPEP device exceeds 5 cm H$_2$O.

14. The method of claim 12, wherein a manometer measures the pressure of the air after the flow of air has passed through the pressure stabilizing orifice and provides the indication.

15. The method of claim 12, wherein the indication comprises auditory feedback.

16. The method of claim 12, further comprising blocking the flow of air through the pressure indicator to a surrounding atmosphere.

17. The method of claim 12, further comprising transmitting the flow of air from the OPEP device through a conduit, wherein the pressure stabilizing orifice is positioned in the conduit, and wherein an entire length of the conduit does not exceed a combined length of the pressure indicator and the OPEP device, when the pressure indicator is connected to the OPEP device, as measured from a mouthpiece to an opposite end of the OPEP device.

18. The method of claim 17, wherein a first portion of the conduit is angled outward from the OPEP device, and a second portion of the conduit is parallel to the OPEP device.

19. The method of claim 18, wherein the second portion of the conduit is spaced from the OPEP device by a length less than a length of the first portion of the conduit.

20. The method of claim 12, further comprising adjusting an amount of dampening by increasing or decreasing a size of the pressure stabilizing orifice.

21. A pressure indicator for an oscillating positive expiratory pressure ("OPEP") device, the pressure indicator comprising:
a manometer;
a conduit configured to transmit a pressure from a mouthpiece of the OPEP device to the manometer, the conduit having a first portion angled outward from the mouthpiece and a second portion extending parallel to the mouthpiece; and,
a pressure stabilizing orifice positioned within the conduit, the pressure stabilizing orifice being configured to dampen oscillations in the pressure transmitted from the OPEP device to the manometer;
wherein an entire length of the conduit does not exceed a combined length of the pressure indicator and the OPEP device, when the pressure indicator is connected to the OPEP device, as measured from the mouthpiece to an opposite end of the OPEP device.

22. A system comprising:
the pressure indicator of claim 21; and
an oscillating positive expiratory pressure device.

* * * * *